(12) United States Patent
Yoshida et al.

(10) Patent No.: US 10,741,824 B2
(45) Date of Patent: Aug. 11, 2020

(54) BATTERY AND ELECTRONIC DEVICE

(71) Applicant: TOHOKU UNIVERSITY, Sendai-shi, Miyagi (JP)

(72) Inventors: Shinya Yoshida, Sendai (JP); Tsutomu Nakamura, Sendai (JP); Hiroshi Hyodo, Sendai (JP); Itaru Honma, Sendai (JP)

(73) Assignee: TOHOKU UNIVERSITY, Sendai-shi, Miyagi (JP)

( * ) Notice: Subject to any disclaimer, the term of this patent is extended or adjusted under 35 U.S.C. 154(b) by 83 days.

(21) Appl. No.: 16/020,500

(22) Filed: Jun. 27, 2018

(65) Prior Publication Data

US 2018/0315989 A1    Nov. 1, 2018

Related U.S. Application Data

(63) Continuation of application No. PCT/JP2016/057496, filed on Mar. 10, 2016.

(30) Foreign Application Priority Data

Dec. 28, 2015   (JP) .................................. 2015-255668

(51) Int. Cl.
*H01M 2/36* (2006.01)
*H01M 6/32* (2006.01)
*A61B 5/00* (2006.01)

(52) U.S. Cl.
CPC ........... *H01M 2/365* (2013.01); *A61B 5/6861* (2013.01); *H01M 2/36* (2013.01); *H01M 2/368* (2013.01); *H01M 6/32* (2013.01)

(58) Field of Classification Search
CPC ........ H01M 2/36; H01M 2/365; H01M 2/368; H01M 6/32; A61B 5/6861
See application file for complete search history.

(56) References Cited

U.S. PATENT DOCUMENTS

| | | |
|---|---|---|
| 2006/0289640 A1 | 12/2006 | Mercure et al. |
| 2010/0239616 A1 | 9/2010 | Hafezi et al. |
| 2011/0105864 A1 | 5/2011 | Robertson et al. |
| 2012/0289775 A1 | 11/2012 | Murata |
| 2015/0051465 A1 | 2/2015 | Robertson et al. |

FOREIGN PATENT DOCUMENTS

| | | |
|---|---|---|
| JP | 59-181583 | * 12/1984 |
| JP | 59-181583 U | 12/1984 |
| JP | 2005-294222 A | 10/2005 |
| JP | 2014-529378 A | 11/2014 |

(Continued)

OTHER PUBLICATIONS

International Search Report issued for corresponding International Patent Application No. PCT/JP2016/057496, dated Jun. 14, 2016.

(Continued)

*Primary Examiner* — Brittany L Raymond
(74) *Attorney, Agent, or Firm* — Myers Wolin, LLC

(57) ABSTRACT

A battery includes a main body having a space therein, and including a channel communicating between an outside and the space; a pair of electrodes adjoining the space; and a valve that closes the channel responsive to pH.

11 Claims, 36 Drawing Sheets

(56) References Cited

FOREIGN PATENT DOCUMENTS

WO 2011/092936 A1 8/2011

OTHER PUBLICATIONS

The extended European search report (EESR) with supplementary European search report and European search opinion issued for corresponding European Patent Application No. 16881451.5, dated Jul. 10, 2019.
International Preliminary Report on Patentability with Written Opinion of the International Searching Authority issued for corresponding International Patent Application No. PCT/JP2016/057496, dated Jul. 12, 2018, with English translation.

* cited by examiner

US 10,741,824 B2

BATTERY AND ELECTRONIC DEVICE

CROSS-REFERENCE TO RELATED APPLICATION

This application is a continuation application of International Application PCT/JP2016/057496, filed on Mar. 10, 2016 and designated the U.S., which claims priority to Japanese Patent Application No. 2015-255668, filed on Dec. 28, 2015. The contents of these applications are incorporated herein by reference.

FIELD

The embodiments discussed herein are related to a battery and an electronic device.

BACKGROUND

Batteries are known, which are introduced to the digestive tract of a living body where a fluid in the digestive tract functions as an electrolyte, to generate electric power. For example, the battery disclosed in Patent Document 1 includes a space to which a fluid is to enter, and a channel communicating between the space and the outside of the battery. The gastric fluid are used as a fluid acting as an electrolyte.

LIST OF RELATED ART DOCUMENT

[Patent Document 1] Japanese Laid-open Patent Publication No. 2010-508293

In the meantime, matters other than gastric fluid, such as fluids with a higher pH than that of the gastric fluid (e.g., pancreatic fluid, bile, and intestinal fluids) and solid matters (e.g., foods and feces), are present in the digestive tract downstream to the stomach.

Thus, in the digestive tract downstream to the stomach, such matters other than the gastric fluid may accidentally enter the space inside the battery. For example, if a fluid with a higher pH than that of the gastric fluid enters the space inside the battery, the pH of the fluid in the space may exceed that of the gastric fluid. Or, a solid matter may enter the space inside the battery, and the solid matter may attach to an electrode, for example. There have been issues where the entry or adhesion sometimes leads to a reduction in the output of electric power (in other words, the power output) generated by the battery in the digestive tract downstream to the stomach.

Such issues may also arise when a fluid other than gastric fluid is used as an electrolyte-acting fluid.

SUMMARY

In one aspect, a battery includes: a main body having a space therein, and having a channel communicating between an outside and the space; a pair of electrodes adjoining the space; and a valve that closes the channel responsive to pH.

In another aspect, an electronic device includes: a battery that generates electric power; and a circuit that is energized by the generated electric power, the battery including: a main body having a space therein, and having a channel communicating between an outside and the space; a pair of electrodes adjoining the space; and a valve that closes the channel responsive to pH.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Hereinafter, embodiments of a battery and an electronic device of the present invention will be described with reference to FIGS. 1-36.

First Embodiment (Structure)

Figure 1:
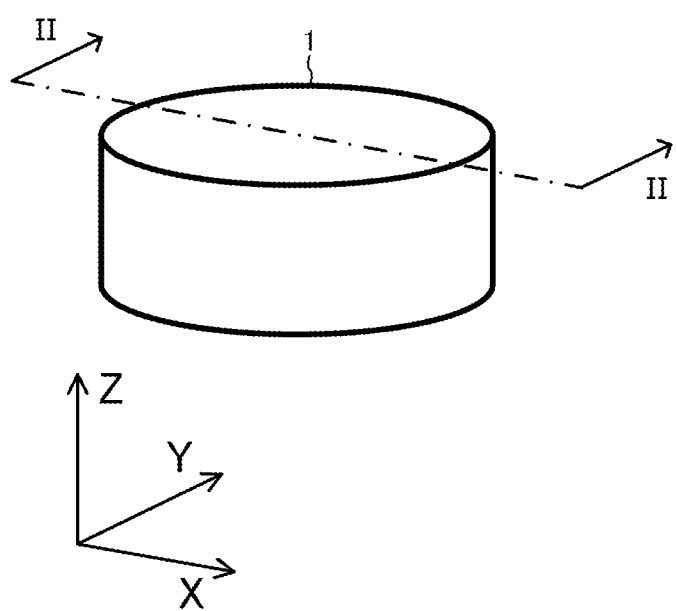
FIG. 1 is a perspective view of an electronic device of a first embodiment.

Referring to in FIG. 1, an electronic device 1 of a first embodiment is in a cylindrical shape. The electronic device 1 may be in any shape other than the cylindrical shape, such as spherical, disc, lenticular shape, or a columnar shape with the bottom in any shape other than the circular shape (e.g., oval, polygonal, or any other shape). Alternatively, the electronic device 1 may be in a rounded square columnar shape.

In this example, the electronic device 1 is an ingestible sensor. The electronic device 1 may be attached to a pharmaceutical preparation (in other words, dosage form), such as an encapsulated formulation or a tablet. Alternatively, the electronic device 1 may define at least a part of a pharmaceutical preparation, such as an encapsulated formulation or a tablet.

The electronic device 1 has a length (in other words, a height of the electronic device 1) between 1 mm and 20 mm, in the direction along the central axis, for example. The bottom of the electronic device 1 has a diameter between 1 mm and 20 mm, for example.

The electronic device 1 will be described using the right-hand Cartesian coordinates system defined by the X, Y, and Z axes, as illustrated in FIGS. 1-5. The same Cartesian coordinates system as that in FIGS. 1-5 will be used in FIGS. 6-36 described later.

The Z axis extends along the direction of the height of the electronic device 1 (in other words, the central axis of the electronic device 1). The X and Y axes extend along the directions parallel to the bottom of the electronic device 1, respectively.

Figure 2:
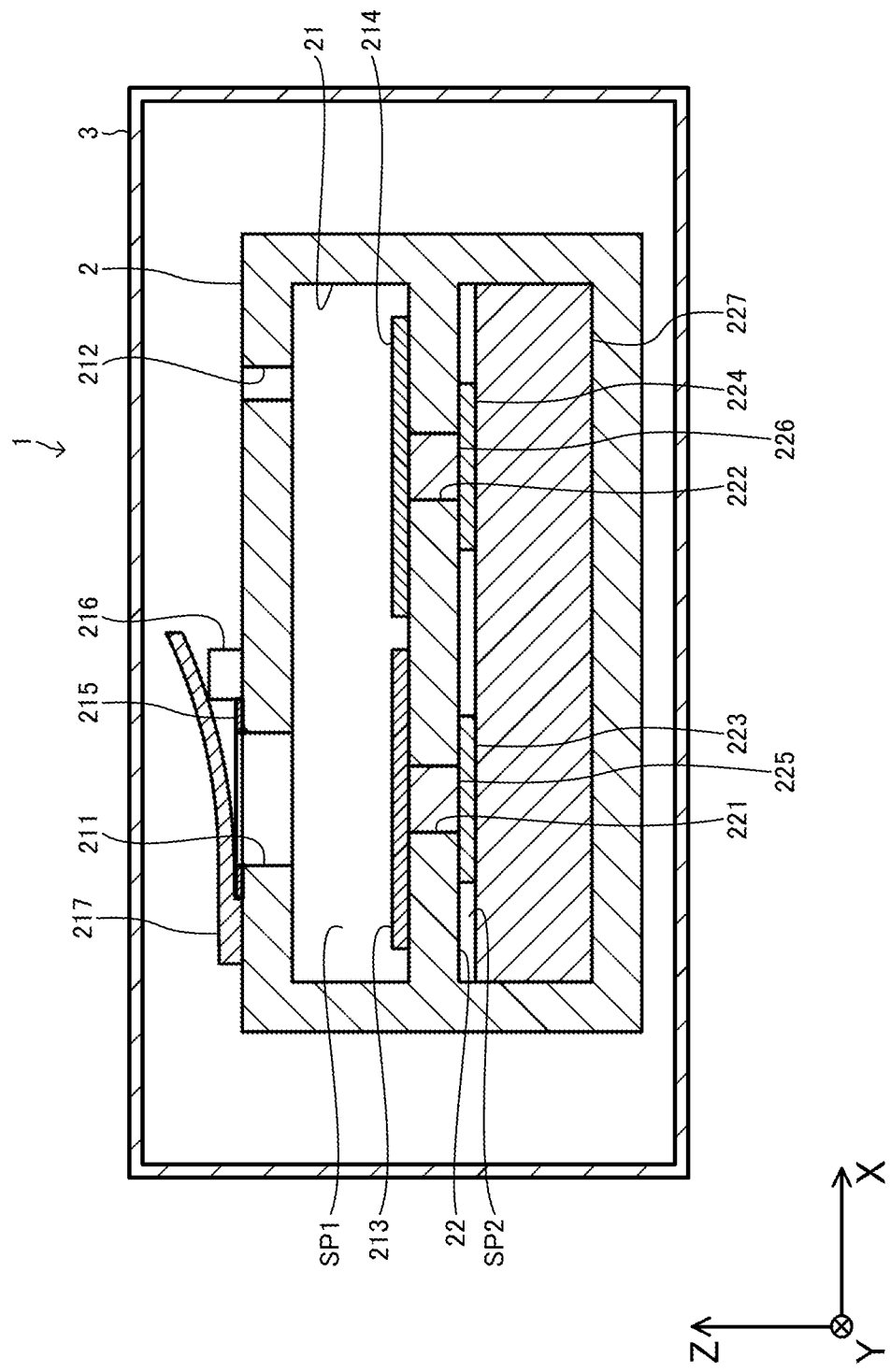
FIG. 2 is a cross-sectional view of the electronic device of the first embodiment.

FIG. 2 illustrates the cross-section of the electronic device 1 on the plane passing Line II-II in FIG. 1, which passes through the central axis of the electronic device 1 and is perpendicular to the Y axis. The plane perpendicular to the Y axis may also be referred to as the ZX plane. As illustrated in FIG. 2, the electronic device 1 includes a main body 2 and a film 3.

In this example, the main body 2 is made from silicon (Si). At least a part of the main body 2 may be made from glass.

In this example, the main body 2 is in a pillar shape extending along the Z axis. In this example, the bottom of the main body 2 is in a square shape. The bottom of the main body 2 may be in any shape other than the square shape (e.g., circular, oval, rectangular, polygonal, or any other shape).

The film 3 coats the main body 2. The film 3 constitutes the surface of the electronic device 1. The film 3 is made from material that is to be dissolved responsive to pH. In this example, the film 3 is made from material that is to be dissolved upon contacting a fluid with pH lower than a predetermined threshold (e.g., pH of 5). The film 3 is made from material that is to be dissolved upon contacting a gastric fluid (in other words, gastrosoluble material), for example. At least a part of the film 3 may constitute a sugar coating. In this case, the sugar coating may contain sucrose, gelatin, hydroxypropylcellulose, or hydroxypropyl methylcellulose phthalate, as a main component.

For example, the gastrosoluble material has the main component selected from at least one of: calcium carbonate, magnesium carbonate, calcium phosphate, magnesium hydroxide, magnesium phosphate, gastrosoluble polyvinyl derivatives such as polyvinyl acetal diethylaminoacetate, methyl methacrylate-butyl methacrylate-dimethylaminoethyl methacrylate copolymer, methyl methacrylate-diethylaminoethyl methacrylate copolymer, and the like.

The electronic device 1 may include a padding member (not illustrated) between the main body 2 and the film 3 on the plane perpendicular to the Z axis (in other words, the XY plane). In this case, the padding member may be made from resin.

As illustrated in FIG. 2, the main body 2 includes a first space defining part 21 defining a first space SP1 inside the main body 2, and a second space defining part 22 defining a second space SP2 inside the main body 2. In this example, the part of the main body 2 where the first space defining part 21 is located constitutes a first layer. In this example, the part of the main body 2 where the second space defining part 22 is located constitutes a second layer different from the first layer.

The first space SP1 and the second space SP2 are in pillar shapes extending along the Z axis. In this example, the bottoms of the first space SP1 and the second space SP2 are in square shapes. The respective bottoms of the first space SP1 and the second space SP2 may be in any shapes other than the square shapes (e.g., circular, oval, rectangular, polygonal, or any other shapes). In this example, the bottom of the first space SP1 is in the same shape as that of the bottom of the second space SP2. The bottom of the first space SP1 may be in any shape other than the shape of the bottom of the second space SP2.

In this example, the central axis of the first space SP1 coincides with the central axis of the second space SP2. The first space SP1 is on the positive direction side of the Z axis relative to the second space SP2.

The electronic device 1 may include a retaining member made from porous material in the first space SP1. In this case, the porous material is preferably hydrophilic.

Figure 3:
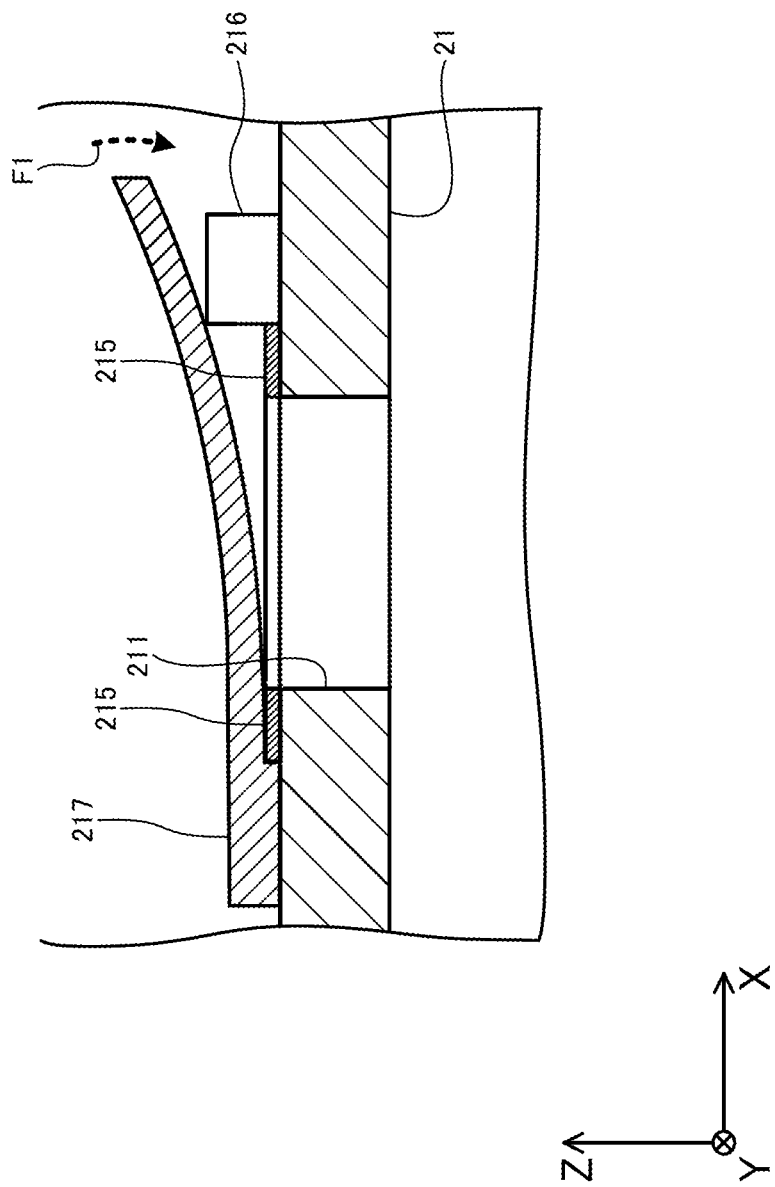
FIG. 3 is a partial cross-sectional view of the electronic device of the first embodiment, in an enlarged view of a valve member.
Figure 4:
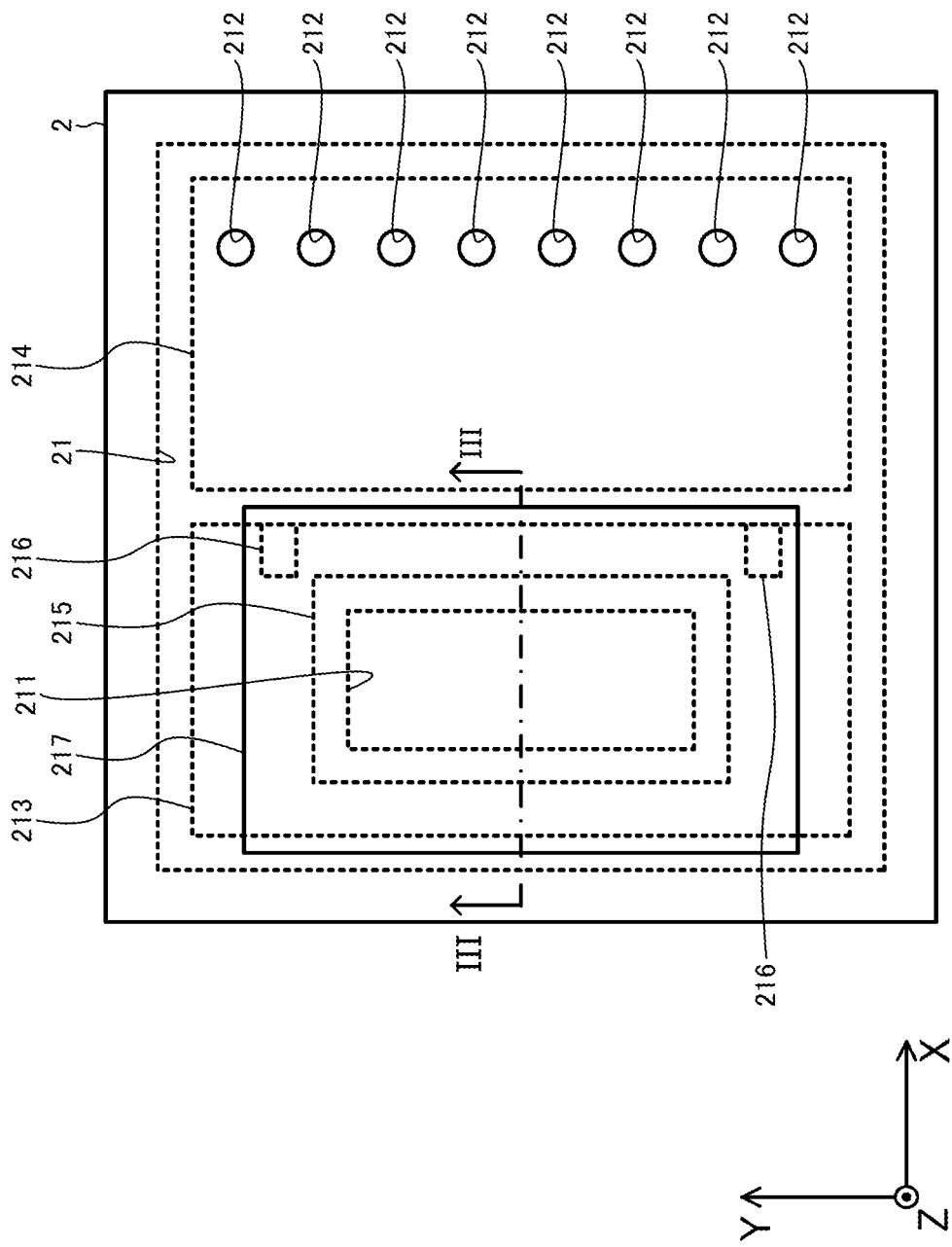
FIG. 4 is a top view of the main body of the first embodiment.

The main body 2 further includes a channel defining part 211 and multiple (eight in this example) through-hole parts 212, as illustrated in FIGS. 2-4. The electronic device 1 further includes a first electrode 213, a second electrode 214, a valve seat 215, multiple (two in this example) supports 216, and valve member 217. In this example, the main body 2, the film 3, the first electrode 213, the second electrode 214, the valve seat 215, the multiple supports 216, and the valve member 217 of the electronic device 1, constitute a battery (in other words, cell). In this example, the first electrode 213 and the second electrode 214 may also be referred to as the pair of electrodes.

FIG. 3 is a partial cross-sectional view of the electronic device 1 on the plane passing Line III-III in FIG. 4, in an enlarged view of the valve member 217 in FIG. 2. FIG. 4 is a diagram of the main body 2 when viewed toward the negative direction of the Z axis (in other words, a diagram viewing the top of the main body 2).

The channel defining part 211 defines a hole that passes through the wall, which defines the end face of the first space defining part 21 on the positive direction side of the Z axis, of the main body 2 in the Z-axis direction, and that is in a pillar shape extending along the Z axis. In other words, the hole defined by the channel defining part 211 communicates between the first space SP1 and the outside of the main body 2. In this example, the hole defined by the channel defining part 211 corresponds to a channel.

In this example, the bottom of the hole defined by the channel defining part 211 is in a rectangular shape. The bottom of the hole defined by the channel defining part 211 may be in any shape other than the rectangular shape (e.g., circular, oval, square, polygonal, or other shape). The hole defined by the channel defining part 211 may be shaped to be a part of a cone.

The long sides of the bottom of the hole defined by the channel defining part 211 have a length between 200 μm and 20 mm, for example. The short sides of the bottom of the hole defined by the channel defining part 211 have a length between 100 μm and 10 mm, for example.

In this example, the channel defining part 211 is located near the end part of the first space defining part 21 on the negative direction side of the X axis. The long sides and the short sides of the bottom of the hole defined by the channel defining part 211 extend along the Y axis and the X axis, respectively.

In this example, the channel defining part 211 and the first space defining part 21 are coated with hydrophilic films. The hydrophilic films are made from silicon dioxide, for example.

Each through-hole part 212 defines a hole that passes through the wall, which defines the end face of the first space defining part 21 on the positive direction side of the Z axis, of the main body 2 in the Z-axis direction, and that is in a pillar shape extending along the Z axis. In other words, the hole defined by each through-hole part 212 communicates between the first space SP1 and the outside of the main body 2.

In this example, the bottom of the hole defined by each through-hole part 212 is in a circular shape. The bottom of the hole defined by each through-hole part 212 may be in any shape other than the circular shape (e.g., oval, square, rectangular, polygonal, or other shape). The hole defined by each through-hole part 212 may be shaped to be a part of a cone.

In this example, the area of the bottom of the hole defined by each through-hole part 212 is smaller than the area of the bottom of the hole defined by the channel defining part 211. The bottom of the hole defined by each through-hole part 212 has a diameter between 2 μm and 200 μm, for example.

In this example, each through-hole part 212 is located near the end part of the first space defining part 21 on the positive direction side of the X axis. The multiple through-hole parts 212 are spaced apart at regular intervals along the Y axis. The number of the through-hole parts 212 may be any number other than eight.

In this example, each through-hole part 212 is coated with a water-repellent film. The water-repellent film is made from fluorocarbon resin (e.g., resin containing polytetrafluoroethylene as the main component), for example.

In this example, the first electrode 213 is made from magnesium. The first electrode 213 may be made from any material other than magnesium (e.g., zinc, alloy, or the like). Alternatively, the first electrode 213 may be a film stack where multiple layers respectively made from different materials are stacked.

The first electrode 213 is in a planer shape that is parallel to the XY plane. The first electrode 213 has a thickness between 100 nm and 2 mm, for example. In this example, the first electrode 213 is in a rectangular shape. The first electrode 213 may be in any shape other than the rectangular shape (e.g., circular, oval, square, polygonal, or other shape).

The first electrode 213 contacts the end face of the first space defining part 21 on the negative direction side of the Z axis.

In this example, the area of the first electrode 213 is slightly smaller than the half of the area of the end face of the first space defining part 21 on the negative direction side of the Z axis. In this example, the long sides and the short sides of the first electrode 213 extend along the Y axis and the X axis, respectively.

In this example, the second electrode 214 is made from platinum. The second electrode 214 may be made from any material other than platinum (e.g., copper chloride (CuCl), silver chloride (AgCl), alloy, or the like). Alternatively, the second electrode 214 may be a film stack where multiple layers respectively made from different materials are stacked.

The second electrode 214 is in a planer shape that is parallel to the XY plane. The second electrode 214 has a thickness between 10 nm and 2 mm, for example. In this example, the second electrode 214 is in a rectangular shape. The second electrode 214 may be in any shape other than the rectangular shape (e.g., circular, oval, square, polygonal, or other shape).

The second electrode 214 contacts the end face of the first space defining part 21 on the negative direction side of the Z axis.

In this example, the area of the second electrode 214 is slightly smaller than the half of the area of the end face of the first space defining part 21 on the negative direction side of the Z axis. In this example, the long sides and the short sides of the second electrode 214 extend along the Y axis and the X axis, respectively.

In this example, the first electrode 213 is on the negative direction side of the X axis, relative to the center in the X-axis direction of the end face of the first space defining part 21 on the negative direction side of the Z axis. In this example, the second electrode 214 is on the positive direction side of the X axis, relative to the center in the X-axis direction in the end face of the first space defining part 21 on the negative direction side of the Z axis. In other words, the first electrode 213 and the second electrode 214 are separated from each other.

In this example, the materials of the first electrode 213 and the second electrode 214 are selected such that electric power is generated with a gastric fluid functioning as an electrolyte once a gastric fluid has been introduced to the first space SP1.

In this example, the valve seat 215 is made from metal. The valve seat 215 may be made from material other than metal (e.g., resin containing polyimide as a main component and the like).

The valve seat 215 is in a planer shape that is parallel to the XY plane. The valve seat 215 has a thickness between 10 nm and 10 μm, for example. The valve seat 215 contacts the end face of the surfaces of the main body 2 on the positive direction side of the Z axis.

The valve seat 215 has a predetermined width, and extends along the edge of the channel defining part 211 on the positive direction side of the Z axis. The edge of the channel defining part 211 on the positive direction side of the Z axis may also be referred to as the outer edge of the end face of the hole defined by the channel defining part 211 on the positive direction side of the Z axis. Further, the edge of the channel defining part 211 on the positive direction side of the Z axis may also be referred to as the outer edge of the opening of the hole defined by the channel defining part 211 in the end face of the surfaces of the main body 2 on the positive direction side of the Z axis.

In other words, the valve seat 215 has a hole that has an shape on the XY plane coinciding with the shape of the hole defined by the channel defining part 211 on the XY plane, and passes through in the Z-axis direction.

Each support 216 is made from material that is to be dissolved responsive to pH. In this example, each support 216 is made from material that is to be dissolved upon contacting a fluid with a pH lower than a predetermined threshold (e.g., pH of 5). Each support 216 is made from material that is to be dissolved upon contacting a gastric fluid (in other words, gastrosoluble material), for example.

Each support 216 is in a pillar shape extending along the Z axis. In this example, the bottom of each support 216 is in a rectangular shape. The bottom of each support 216 may be in any shape other than the rectangular shape (e.g., circular, oval, square, polygonal, or other shape).

For example, each support 216 has a length (in other words, the height of the support 216) between 10 μm and 1 mm in the Z-axis direction. In this example, the height of each support 216 is greater than the thickness of the valve seat 215.

Each support 216 contacts the end face of the surfaces of the main body 2 on the positive direction side of the Z axis. In this example, the long sides and the short sides of each support 216 extend along the X axis and the Y axis, respectively.

Each support 216 is on the positive direction side of the X axis relative to the channel defining part 211. One of the two supports 216 is on the positive direction side of the Y axis relative to the channel defining part 211, and the other is on the negative direction side of the Y axis relative to the channel defining part 211. In other words, the two supports 216 are separated from each other.

The supports 216 may have positions and sizes different from the position and the size illustrated in FIG. 4. The supports 216 may be located in predetermined regions of the outer periphery of the valve seat 215, for example.

The number of the supports 216 may be any number other than two.

In this example, the supports 216 are configured such that the supports 216 are dissolved completely once a fluid has been introduced to the first space SP1 through the hole defined by the channel defining part 211, when the pH external to the first space SP1 is lower than the above-described threshold.

The valve member 217 is made from silicon (Si). The valve member 217 may be made from any material (e.g., metal, resin, or the like) other than silicon.

The valve member 217 is in a planer shape that is parallel to the XY plane while not being elastically deformed. The valve member 217 has a thickness between 100 nm and 200 μm, for example.

In this example, the valve member 217 is in a rectangular shape while not being elastically deformed. The valve member 217 may be in any shape other than the rectangular shape (e.g., circular, oval, square, polygonal, or other shape) while not being elastically deformed. In this example, the long sides and the short sides of the valve member 217 extend along the Y axis and the X axis, respectively, while the valve member 217 is not elastically deformed.

In the X-axis direction, the valve member 217 extends from the negative direction side of the X axis relative to the valve seat 215, to the positive direction side of the X axis relative to the valve seat 215 (in this example, the positive direction side of the X axis relative to the supports 216).

In the Y-axis direction, the valve member 217 extends from the negative direction side of the Y axis relative to the valve seat 215, to the positive direction side of the Y axis relative to the valve seat 215. In this example, in the Y-axis direction, the valve member 217 extends from the negative direction side of the Y axis relative to the support 216 on the negative direction side of the Y axis from among the two supports 216, to the positive direction side of the Y axis relative to the support 216 on the positive direction side of the Y axis from among the two supports 216.

In other words, when the main body 2 is viewed toward the negative direction of the Z axis, the valve member 217 covers the hole defined by the channel defining part 211, the valve seat 215, and the supports 216.

The part of the valve member 217 on the negative direction side of the X axis relative to the valve seat 215 contacts the end face of the surfaces of the main body 2 on the positive direction side of the Z axis. In this example, the part of the valve member 217 on the negative direction side of the X axis relative to the valve seat 215 is secured to the end face of the surfaces of the main body 2 on the positive direction side of the Z axis.

As illustrated in FIGS. 2 and 3, the valve member 217 is supported by the supports 216, with being curved by an elastic deformation such that a portion of the valve member 217 is displaced further to the positive direction side of the Z axis as the portion approaches, in the X-axis direction, the end of the valve member 217 on the positive direction side of the X axis.

In other words, as illustrated in FIG. 3, the valve member 217 undergoes the resiliency (in other words, restoring force) F1 generated against the elastic deformation. In this example, the resiliency F1 can be interpreted as the force to restore the valve member 217 to its unbent state (in other words, the force to restore the valve member 217 to be parallel to the XY plane). In this example, the resiliency F1 can also be interpreted as the force to displace the end of the valve member 217 on the positive direction side of the X axis to the negative direction of the Z axis.

In the manner as described above, the valve member 217 is biased toward the valve seat 215, and is supported by the supports 216 at the position away from the valve seat 215.

Figure 5:
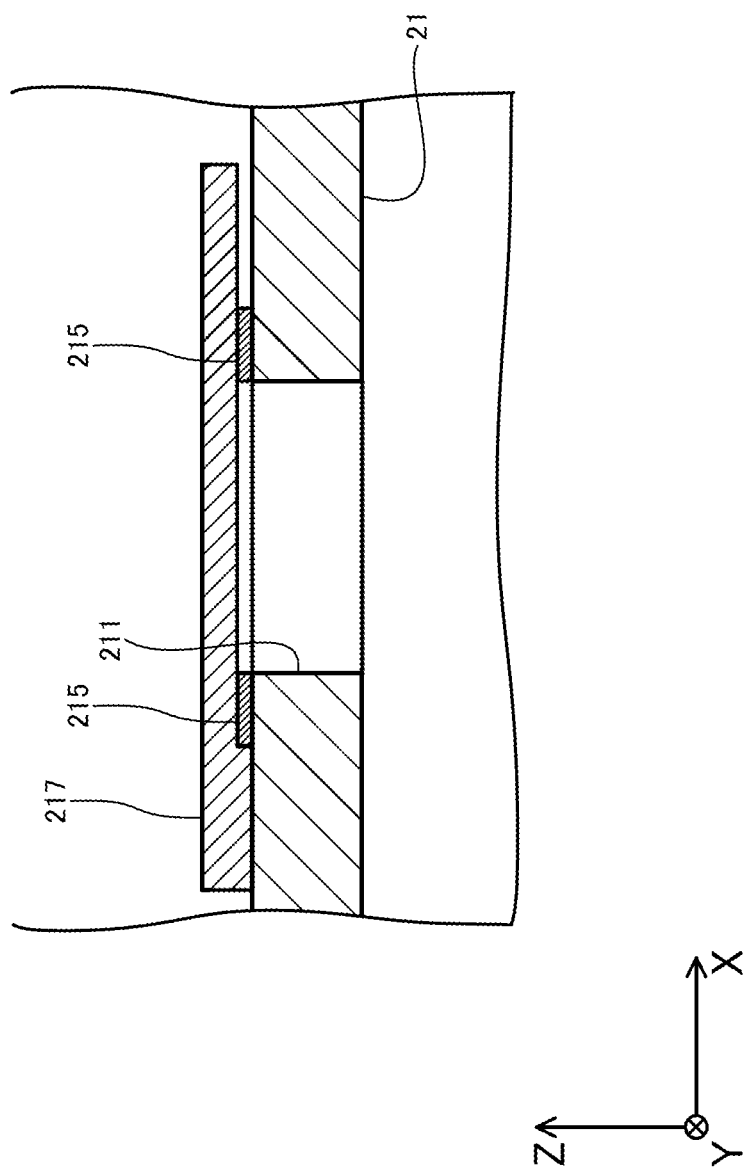
FIG. 5 is a partial cross-sectional view of the electronic device once a support has been dissolved, in an enlarged view of a valve member of the first embodiment.

As illustrated in FIG. 5, once the supports 216 have been dissolved, the valve member 217 is restored to be parallel to the XY plane by the resiliency F1. As a result, the valve member 217 contacts the valve seat 215. In this example, the valve member 217 is pressed against the valve seat 215. As a result, the valve member 217 closes the channel communicating between the first space SP1 and the outside of the main body 2. The term "closing the channel" may also be referred to as "blocking the channel".

In this example, the valve seat 215, the supports 216, and the valve member 217 correspond to a valve that closes the channel communicating between the first space SP1 and the outside of the main body 2 responsive to pH. In this example, the valve closes the channel communicating between the first space SP1 and the outside of the main body 2 once a fluid has been introduced to the first space SP1 through the hole defined by the channel defining part 211, when the pH external to the first space SP1 is lower than the above-described threshold.

Additionally, as illustrated in FIG. 2, the electronic device 1 includes a first through-hole part 221, a second through-hole part 222, a first terminal 223, a second terminal 224, a first conductor 225, a second conductor 226, and a circuit 227.

The first through-hole part 221 defines a hole that passes through the wall, which defines the end face of the first space defining part 21 on the negative direction side of the Z axis and defines the end face of the second space defining part 22 on the positive direction side of the Z axis, of the main body 2 in the Z-axis direction, and is in a pillar shape extending along the Z axis.

In this example, the bottom of the hole defined by the first through-hole part 221 is in a circular shape. The bottom of the hole defined by the first through-hole part 221 may be in any shape other than the circular shape (e.g., oval, square, rectangular, polygonal, or other shape). The hole defined by the first through-hole part 221 may be shaped to be a part of a cone.

The outer edge of the first through-hole part 221 on the XY plane is located inside the outer edge of the first electrode 213 on the XY plane. In this example, the first through-hole part 221 is located at the center part of the first electrode 213 on the XY plane.

The second through-hole part 222 defines a hole that passes through the wall, which defines the end face of the first space defining part 21 on the negative direction side of the Z axis and defines the end face of the second space defining part 22 on the positive direction side of the Z axis, of the main body 2 in the Z-axis direction, and is in a pillar shape extending along the Z axis.

In this example, the bottom of the hole defined by the second through-hole part 222 is in a circular shape. The bottom of the hole defined by the second through-hole part 222 may be in any shape other than the circular shape (e.g., oval, square, rectangular, polygonal, or other shape). The hole defined by the second through-hole part 222 may be shaped to be a part of a cone.

The outer edge of the second through-hole part 222 on the XY plane is located inside the outer edge of the second electrode 214 on the XY plane. In this example, the second through-hole part 222 is located at the center part of the second electrode 214 on the XY plane.

In this example, the first terminal 223 is made from metal. The first terminal 223 is in a planer shape that is parallel to the XY plane. The first terminal 223 contacts the end face of the second space defining part 22 on the positive direction side of the Z axis.

The outer edge of the first terminal 223 on the XY plane is located outside the outer edge of the first through-hole part 221 on the XY plane. In this example, the first terminal 223 is located such that the first through-hole part 221 is located at the center part of the first terminal 223 on the XY plane.

In this example, the second terminal 224 is made from metal. The second terminal 224 is in a planer shape that is parallel to the XY plane. The second terminal 224 contacts the end face of the second space defining part 22 on the positive direction side of the Z axis.

The outer edge of the second terminal 224 on the XY plane is located outside the outer edge of the second through-hole part 222 on the XY plane. In this example, the second terminal 224 is located such that the second through-hole part 222 is located at the center part of the second terminal 224 on the XY plane.

In this example, the first conductor 225 is made from metal. The first conductor 225 is filled in the hole defined by the first through-hole part 221, thereby connecting the first electrode 213 and the first terminal 223.

In this example, the second conductor 226 is made from metal. The second conductor 226 is filled in the hole defined by the second through-hole part 222, thereby connecting the second electrode 214 and the second terminal 224.

The circuit 227 is connected to the first terminal 223 and the second terminal 224. The circuit 227 is energized by the potential difference induced between the first electrode 213 and the second electrode 214 when a fluid acting as an electrolyte enters the first space SP1. In this example, inducing the potential difference between the first electrode 213 and the second electrode 214 corresponds to generating electric power.

For example, the circuit 227 includes at least one of a sensing circuit and a communication circuit.

The sensing circuit senses a physical quantity. The physical quantity is temperature, pH, or concentration of a target, for example. The target is a digestive fluid (e.g., gastric fluid, intestinal fluid, pancreatic fluid, or the like), blood, indigenous bacteria, or infectious material (e.g., bacteria, virus, or the like), for example. The concentration of the target equal to or greater than a predetermined threshold can be interpreted that the target is present.

The communication circuit wirelessly communicates with an apparatus external to the electronic device 1. For example, when the circuit 227 includes the sensing circuit and the communication circuit, the communication circuit sends a signal indicative of a physical quantity sensed by the sensing circuit.

(Operations)

Next, operations of the electronic device 1 will be described.

First, the electronic device 1 is introduced to the mouth of a living body (e.g., human body). The electronic device 1 is then swallowed by the living body and reaches the esophagus. Since the film 3 is not dissolved in saliva, no fluid enters the first space SP1 in the mouth and the esophagus.

Thereafter, the electronic device 1 reaches the stomach. As a result, the pH external to the electronic device 1 declines below the above-described threshold. This causes the film 3 to be dissolved. As a result, gastric fluid enters the first space SP1 through the hole defined by the channel defining part 211. Any gas remaining in the first space SP1 is exhausted through the through-hole parts 212.

As a result, the gastric fluid introduced to the first space SP1 functions as an electrolyte, and hence the battery in the electronic device 1 generates electric power. The circuit 227 is energized by the generated electric power.

Once the gastric fluid has been introduced to the first space SP1, the supports 216 are dissolved completely.

The valve member 217 is then restored to be parallel to the XY plane by the resiliency. This causes the valve member 217 to be pressed against the valve seat 215. As a result, the valve member 217 closes the channel communicating between the first space SP1 and the outside of the main body 2.

This can prevent any matters other than the gastric fluid (e.g., fluid with pH different from that of gastric fluid, solid matter, or the like) from entering the first space SP1. As a result, a decline in the power output can be suppressed.

Thereafter, the electronic device 1 reaches the intestines. Since the channel communicating between the first space SP1 and the outside of the main body 2 is closed, an entry of any matters other than the gastric fluid to the first space SP1 is prevented in the digestive tract downstream to the stomach. As a result, a decline in the power output can be suppressed in the digestive tract downstream to the stomach.

Thereafter, the electronic device 1 is excreted from the living body.

As set forth above, the electronic device 1 of the first embodiment has the main body 2 including the first space SP1 defined therein and the channel communicating between the outside and the first space SP1, and includes the pair of electrodes 213, 214 adjoining the first space SP1 and the valve that closes the channel responsive to pH.

In accordance with the above configuration, once the electronic device 1 has been introduced into the digestive tract in a living body, a fluid in the digestive tract enters the first space SP1 through the channel. The fluid introduced to the first space SP1 functions as an electrolyte, and the battery in the electronic device 1 generates electric power. The valve closes the channel responsive to pH. This prevents matters with a pH different from that of the electrolyte-acting fluid (e.g., fluid, solid matter, or the like with a pH different from that of the electrolyte-acting fluid), from entering the first space SP1. As a result, a decline in the power output can be suppressed.

Furthermore, in the electronic device 1 of the first embodiment, the valve includes the valve seat 215, the supports 216 that are dissolved responsive to pH, and the valve member 217 that is biased toward the valve seat 215, supported by the supports 216 at the location distant from the valve seat 215, and contacts the valve seat 215 after dissolution of the supports 216, thereby closing the channel.

In accordance with the above configuration, the supports 216 are dissolved in response to the change in pH. This causes the valve member 217 to contact the valve seat 215, thereby closing the channel.

Further, in the electronic device 1 of the first embodiment, when the pH external to the first space SP1 is lower than the predetermined threshold, the valve closes the channel once the fluid has been introduced to the first space SP1 through the channel.

In the meantime, once the electronic device 1 has been introduced to the stomach, the pH external to the first space SP1 declines below the above-described threshold. In this case, gastric fluid enters the first space SP1 through the channel. The gastric fluid introduced to the first space SP1 functions as an electrolyte, and the battery in the electronic device 1 generates electric power. The valve then closes the channel. Therefore, an entry of any matters other than the gastric fluid to the first space SP1 is prevented in the digestive tract downstream to the stomach. As a result, a decline in the power output can be suppressed in the digestive tract downstream to the stomach.

Furthermore, the electronic device 1 of the first embodiment includes the film 3 that coats the main body 2 and, is dissolved responsive to pH.

In accordance with the above configuration, it is possible to prevent any fluid with a pH different from that of the fluid used as an electrolyte (e.g., liquid, such as water, that is introduced to the digestive tract together with the electronic device 1, saliva, or the like), from entering the first space SP1 prior to the fluid used as an electrolyte (gastric fluid, in this example). This ensures that the fluid used as an electrolyte enters the first space SP1, which in turn ensures that the battery generates electric power in a reliable manner.

Furthermore, in the electronic device 1 of the first embodiment, the battery is disposed at the first layer, whereas the circuit 227 is disposed at the second layer different from the first layer.

In accordance with the above configuration, it is possible to increase the areas of the electrodes 213, 214, as compared to the configuration where the battery and the circuit 227 are disposed at the same layer. This increases the power output.

The film 3 may coat only a portion of the main body 2. In this case, the film 3 may coat a portion of the main body 2 so as to cover the gap between the valve member 217 and the main body 2. Also in such a configuration, the film 3 may also coat a portion of the main body 2 so as to obstruct the through-hole parts 212.

Alternatively, the electronic device 1 may have no film 3. In this case, the electronic device 1 may use a fluid (e.g., a liquid swallowed with the electronic device 1) entering the digestive tract together with the electronic device 1, as an electrolyte. In this case, the supports 216 may be configured to facilitate quick completion of the dissolution of the supports 216, when the pH external to the first space SP1 is lower than the above-described threshold.

The supports 216 may be made from material that is dissolved upon contacting a fluid with a pH higher than a predetermined threshold (e.g., pH of 4). In this case, the supports 216 may be made from material that is dissolved upon contacting the pancreatic fluid, for example. Alternatively, in such a configuration, for example, each support 216 may be made from material (in other words, enteric material) that is dissolved upon contacting an intestinal fluid, for example.

The enteric material contains at least one of: hydroxypropyl methylcellulose phthalate, cellulose acetate phthalate, polyvinyl acetate phthalate, styrene-maleic anhydride copolymer, methacrylate-methyl methacrylate copolymer, carboxymethyl ethyl cellulose, and the like, as a main component, for example.

For example, once the electronic device 1 reaches the duodenum or the small intestine, the pH external to the electronic device 1 exceeds the above-described threshold. In this case, therefore, once the electronic device 1 reaches the duodenum or the small intestine, the supports 216 are dissolved completely. As a result, the valve member 217 closes the channel communicating between the first space SP1 and the outside of the main body 2.

First Modification to First Embodiment

Next, an electronic device of a first modification to the first embodiment will be described. The electronic device of the first modification to the first embodiment is different from the electronic device of the first embodiment in that multiple batteries are provided. Descriptions will be given focusing on that difference. In the descriptions of the first modification to the first embodiment, elements denoted by like reference symbols denote the same or substantially similar elements used in the first embodiment.

Figure 6:
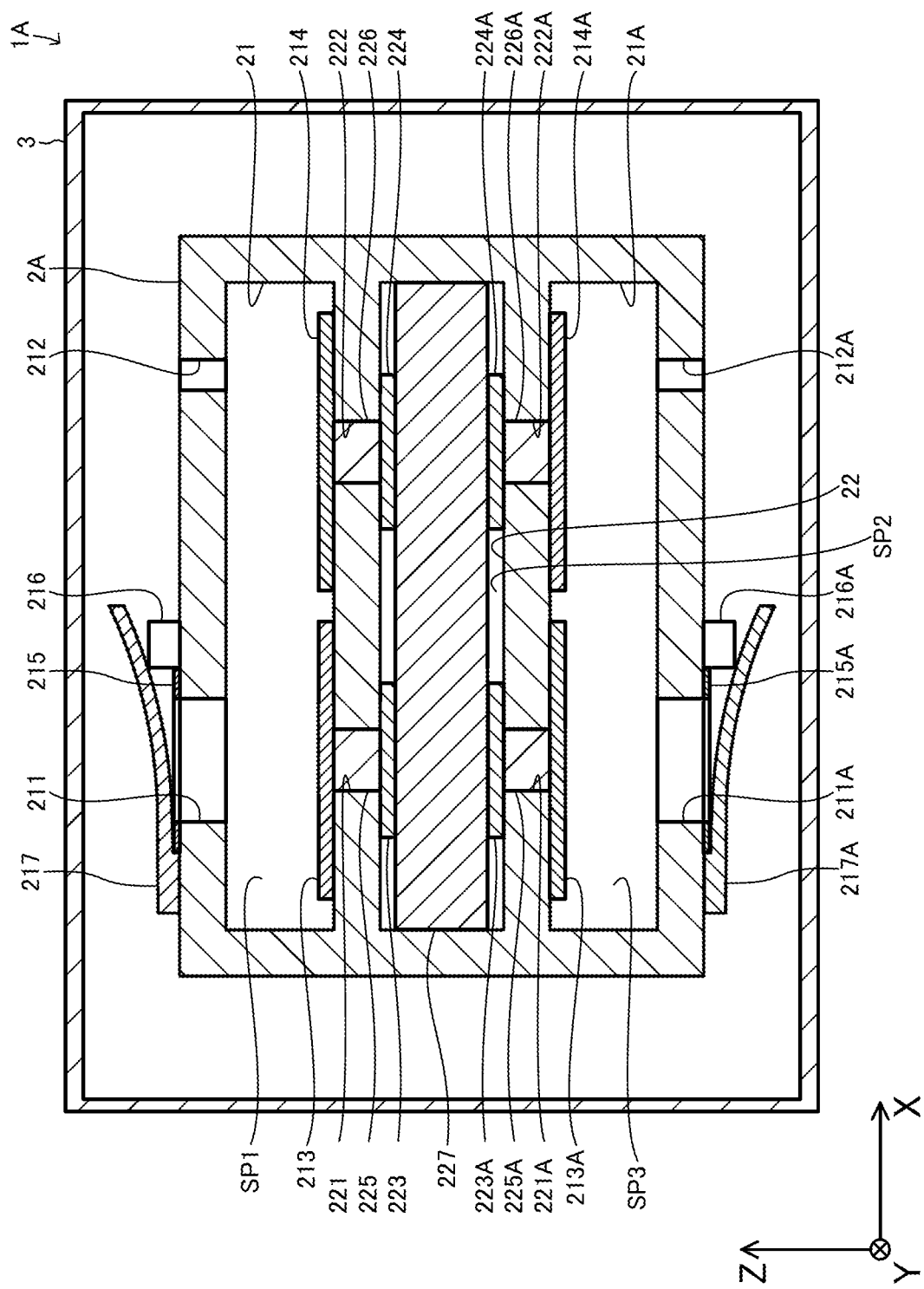
FIG. 6 is a cross-sectional view of the electronic device of a first modification to the first embodiment.

Referring to FIG. 6, an electronic device 1A of the first modification to the first embodiment includes a main body 2A, in place of the main body 2 of the first embodiment.

The main body 2A includes a third space defining part 21A defining a third space SP3 inside the main body 2A, in addition to a first space defining part 21 and a second space defining part 22. In this example, the part of the main body 2A where the third space defining part 21A is disposed defines a third layer. In other words, the third layer is a layer that is disposed opposite to the first layer relative to the second layer, and is different from the first layer and the second layer.

The third space SP3 is in a pillar shape extending along the Z axis. In this example, the bottom of the third space SP3 is in a square shape. The bottom of the third space SP3 may be in any shape other than the square shape (e.g., circular, oval, rectangular, polygonal, or any other shape). In this example, the bottom of the third space SP3 is in the same shape as that of the bottom of the first space SP1. The bottom of the third space SP3 may be in any shape other than that of the bottom of the first space SP1.

In this example, the central axis of the third space SP3 coincides with the central axis of the first space SP1 and the central axis of the second space SP2. In addition, the third space SP3 is on the negative direction side of the Z axis relative to the second space SP2.

The electronic device 1A may include a retaining member made from porous material in the third space SP3. In this case, the porous material is preferably hydrophilic.

In addition to the elements provided in the main body 2, the main body 2A further includes a channel defining part 211A and multiple (eight in this example) through-hole parts 212A. In addition to the elements provided in the electronic device 1, the electronic device 1A further includes a third electrode 213A, a fourth electrode 214A, a valve seat 215A, multiple (two in this example) supports 216A, a valve member 217A, a third through-hole part 221A, a fourth through-hole part 222A, a third terminal 223A, a fourth terminal 224A, a third conductor 225A, and a fourth conductor 226A.

In this example, the main body 2A, the film 3, the first electrode 213, the second electrode 214, the valve seat 215, the multiple supports 216, and the valve member 217 of the electronic device 1A constitute a first battery. In this example, the main body 2A, the film 3, the third electrode 213A, the fourth electrode 214A, the valve seat 215A, the multiple supports 216A, and the valve member 217A of the electronic device 1A constitute a second battery. In this example, the third electrode 213A and the fourth electrode 214A may also be referred to as the pair of electrodes.

The second battery is configured similarly to the first battery, except for the fact that they are disposed plane symmetrically relative to the XY plane (in other words, the reference plane) passing through the center of the main body 2A in the Z-axis direction.

Furthermore, the third through-hole part 221A, the fourth through-hole part 222A, the third terminal 223A, the fourth terminal 224A, the third conductor 225A, and the fourth conductor 226A are configured similarly to the first through-hole part 221, the second through-hole part 222, the first terminal 223, the second terminal 224, the first conductor 225, and the second conductor 226, respectively, except for the fact that they are disposed plane symmetrically relative to the reference plane.

In this example, the circuit 227 is connected to the first terminal 223 and the second terminal 224, and is also connected to the third terminal 223A and the fourth terminal 224A. The circuit 227 is energized by both the potential difference induced between the first electrode 213 and the second electrode 214 when an electrolyte-acting fluid enters the first space SP1, and the potential difference induced between the third electrode 213A and the fourth electrode 214A when the electrolyte-acting fluid enters the third space SP3. In this example, the first terminal 223 and the second terminal 224, and the third terminal 223A and the fourth terminal 224A are connected to the circuit 227 in series.

As set forth above, in accordance with the electronic device 1A of the first modification to the first embodiment, effects and advantages similar to those of the electronic device 1 of the first embodiment are achieved.

Further, the electronic device 1A of the first modification to the first embodiment includes the first battery and the second battery. Additionally, the second battery is disposed at the third layer that is different from the first layer and the second layer, opposite to the first layer relative to the second layer.

In accordance with the above configuration, it is possible to increase the areas of the electrodes 213, 214, 213A, 214A, as compared to the configuration where the second battery is disposed at the same layer as the first battery or the circuit 227. This increases the power output.

Further, in accordance with the electronic device 1A, the first battery and the second battery contain the electrolyte in the respective spaces. Therefore, it is possible to connect the first battery and the second battery in series. As a result, voltage supplied to the circuit 227 is increased.

Second Embodiment

Next, an electronic device of a second embodiment will be described. The electronic device of the second embodiment is different from the electronic device of the first embodiment in terms of the valve member and the supports. Descriptions will be given focusing on that difference. In the descriptions of the second embodiment, elements denoted by like reference symbols denote the same or substantially similar elements used in the first embodiment.

Figure 7:
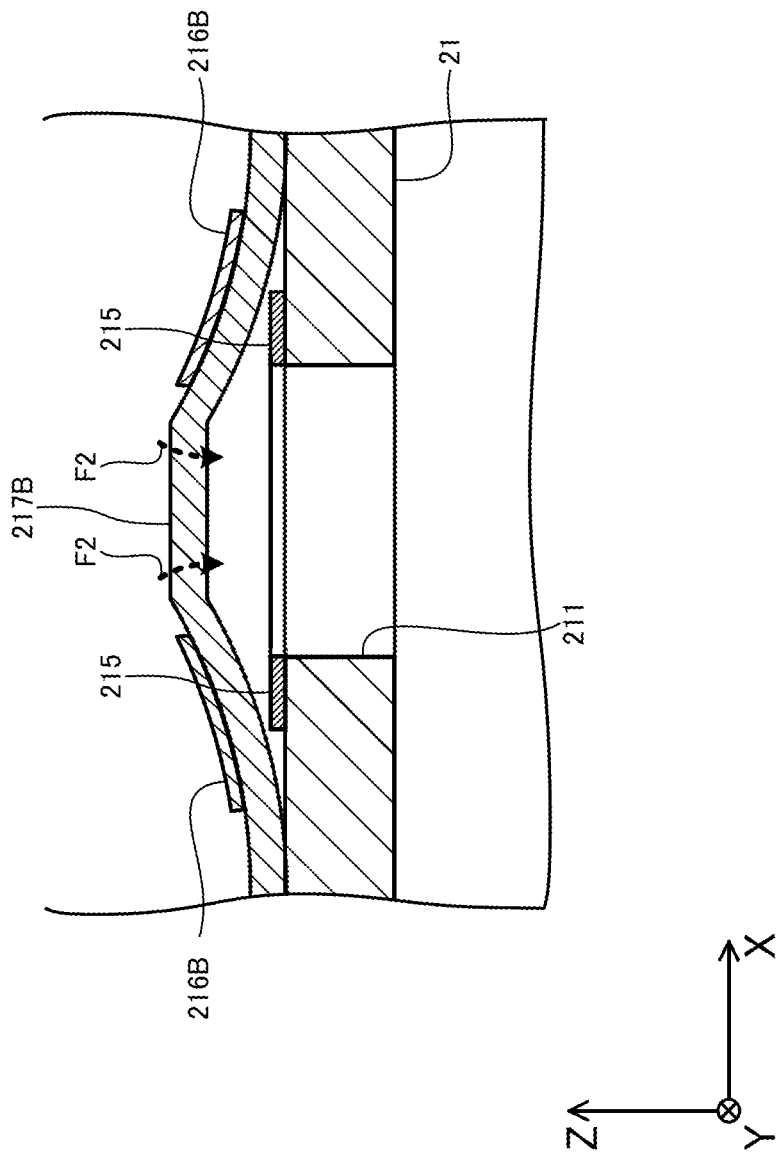
FIG. 7 is a partial cross-sectional view of an electronic device of a second embodiment, in an enlarged view of a valve member.
Figure 8:
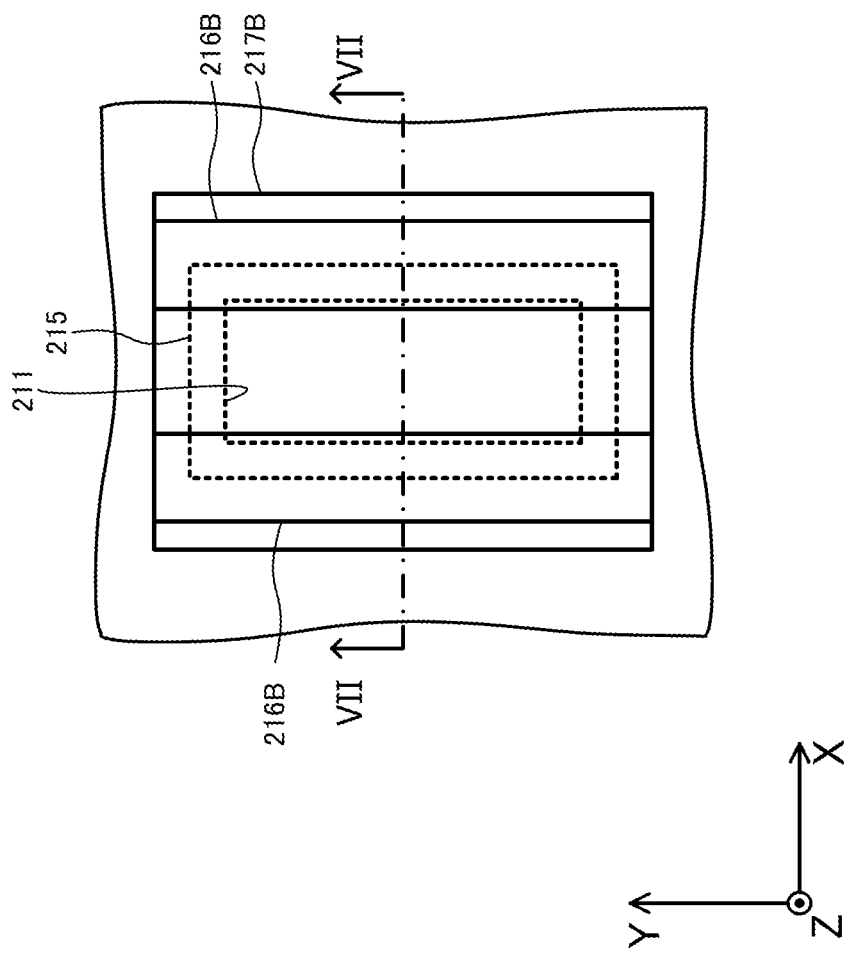
FIG. 8 is a partial top view of a main body of the second embodiment, in an enlarged view of the valve member.
Figure 9:
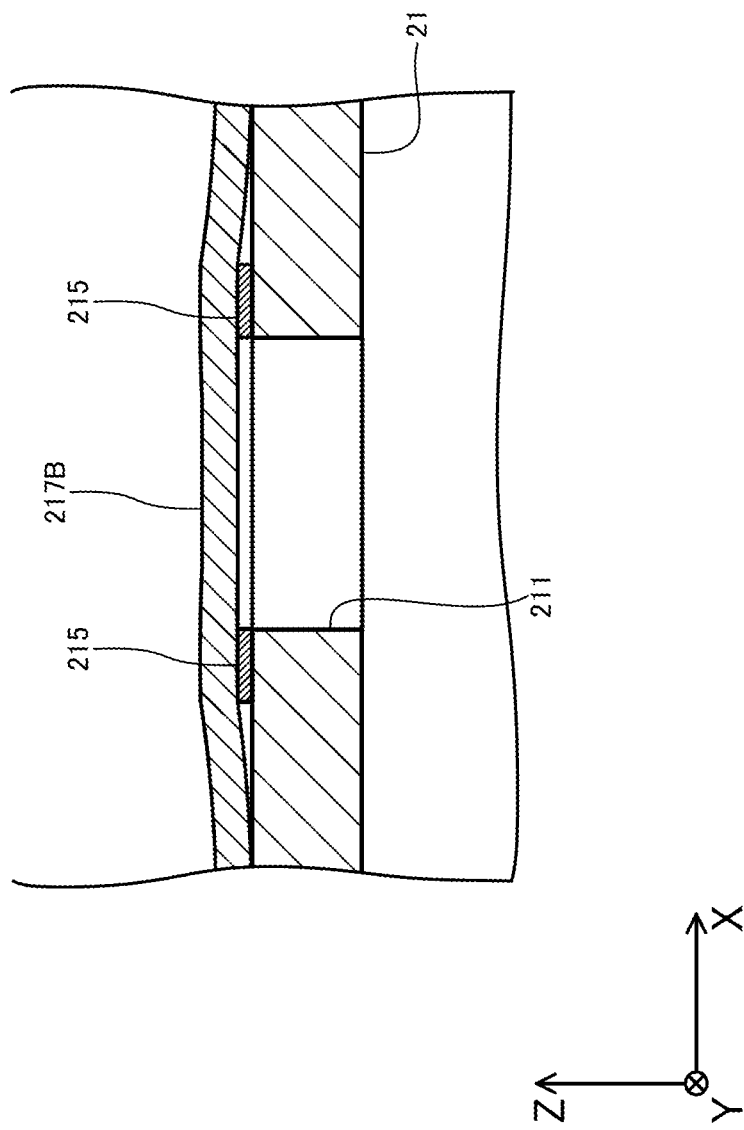
FIG. 9 is a partial cross-sectional view of the electronic device of the second embodiment once supports have been dissolved, in an enlarged view of the valve member.

Referring to FIGS. 7-9, an electronic device 1 of the second embodiment includes multiple (two in this example) supports 216B and a valve member 217B, in place of the multiple supports 216 and the valve member 217 of the first embodiment.

FIG. 7 is a partial cross-sectional view of the electronic device 1 on the plane passing Line VII-VII in FIG. 8, in an enlarged view of the valve member 217B. FIG. 8 is an enlarged view of the area in the vicinity of the valve member 217B, when the main body 2 is viewed toward the negative direction of the Z axis. FIG. 9 is a partial cross-sectional view of the electronic device 1 on the plane passing Line VII-VII in FIG. 8 once the supports 216B have been dissolved, in an enlarged view of the valve member 217B.

The valve member 217B is in a planer shape that is parallel to the XY plane while not being elastically deformed. The valve member 217B has a thickness between 100 nm and 200 µm, for example.

In this example, the valve member 217B is in a rectangular shape while not being elastically deformed. The valve member 217B may be in any shape other than the rectangular shape (e.g., circular, oval, square, polygonal, or other shape) while not being elastically deformed. In this example, the long sides and the short sides of the valve member 217B extend along the Y axis and the X axis, respectively, while the valve member 217B is not elastically deformed.

As illustrated in FIG. 8, in the X-axis direction, the valve member 217B extends from the negative direction side of the X axis relative to the valve seat 215, to the positive direction side of the X axis relative to the valve seat 215. In the Y-axis direction, the valve member 217B extends from the negative direction side of the Y axis relative to the valve seat 215, to the positive direction side of the Y axis relative to the valve seat 215.

In other words, when the main body 2 is viewed toward the negative direction of the Z axis, the valve member 217B covers the hole defined by the channel defining part 211, and the valve seat 215.

Both of the end parts in the X-axis direction of the valve member 217B contact the end face of the surfaces of the main body 2 on the positive direction side of the Z axis. In this example, both of the end parts in the X-axis direction of the valve member 217B are secured to end face of the surfaces of the main body 2 on the positive direction side of the Z axis.

Each support 216B is made from material that is to be dissolved responsive to pH. In this example, each support 216B is made from material that is to be dissolved upon contacting a fluid with a pH lower than a predetermined threshold (e.g., pH of 5). Each support 216B is made from gastrosoluble material, for example. Each support 216B may be made from material that is dissolved upon contacting a fluid with a pH higher than a predetermined threshold (e.g., pH of 4). In this case, each support 216B may be made from enteric material, for example.

Each support 216B is in a planer shape. Each support 216B has a thickness between 10 nm and 200 µm, for example.

As illustrated in FIG. 8, in the X-axis direction, each support 216B extends from the part of the valve member 217B secured to the surface of the main body 2, to the center part of the valve member 217B in the X-axis direction (in this example, in the vicinity of the channel defining part 211). In the Y-axis direction, each support 216B extends from the edge of the valve member 217B on the negative direction side of the Y axis, to the edge of the valve member 217B on the positive direction side of the Y axis.

Each support 216B is secured to the valve member 217B, while the entire end face of the surfaces of that support 216B on the negative direction side of the Z axis contacts the end face of the surfaces of the valve member 217B on the positive direction side of the Z axis.

As illustrated in FIG. 7, the support 216B of the two supports 216B on the negative direction side of the X axis is in a curved shape such that a portion of the support 216B is displaced further to the positive direction side of the Z axis as the portion approaches, in the X-axis direction, the end of the support 216B on the positive direction side of the X axis. The support 216B of the two supports 216B on the positive direction side of the X axis is in a curved shape such that a portion of the support 216B is displaced further to the positive direction side of the Z axis as the portion approaches, in the X-axis direction, the end of the support 216B on the negative direction side of the X axis.

In other words, each of the supports 216B is in the curved shape such that a portion of each support 216B is displaced further to the positive direction side of the Z axis as the portion approaches, in the X-axis direction, the center part of the valve member 217B in the X-axis direction.

As a result, the valve member 217B is supported by the supports 216B, with being curved by an elastic deformation, such that a portion of the valve member 217B is displaced further to the positive direction side of the Z axis as the portion approaches, in the X-axis direction, the center part of the valve member 217B in the X-axis direction.

In other words, as illustrated in FIG. 7, the valve member 217B undergoes the resiliency F2 generated against the elastic deformation. In this example, the resiliency F2 can be interpreted as the force to restore the valve member 217B to its unbent state (in other words, the valve member 217B to be parallel to the XY plane). In this example, the resiliency F2 can also be interpreted as the force to displace the center part of the valve member 217B to the negative direction of the Z axis.

In the manner as described above, the valve member 217B is biased toward the valve seat 215, and is supported by the supports 216B at the location distant from the valve seat 215.

As illustrated in FIG. 9, once the supports 216B have been dissolved, the valve member 217B is restored to be parallel to the XY plane by the resiliency F2. As a result, the valve member 217B contacts the valve seat 215. In this example, the valve member 217B is pressed against the valve seat 215. As a result, the valve member 217B closes the channel communicating between the first space SP1 and the outside of the main body 2.

The supports 216B may have positions and sizes different from the position and the size illustrated in FIG. 8. The number of the supports 216B may be any number other than two.

In this example, the supports 216B are configured such that the supports 216B are dissolved completely once a fluid has been introduced to the first space SP1 through the hole defined by the channel defining part 211, when the pH external to the first space SP1 is lower than the above-described threshold.

The electronic device 1 of the second embodiment operates in the similar manner to the electronic device 1 of the first embodiment. Accordingly, effects and advantages similar to those of the electronic device 1 of the first embodiment are also achieved by the electronic device 1 of the second embodiment.

Third Embodiment

Next, an electronic device of a third embodiment will be described. The electronic device of the third embodiment is different from the electronic device of the first embodiment in terms of the valve member and the supports. Descriptions will be given focusing on that difference. In the descriptions of the third embodiment, elements denoted by like reference symbols denote the same or substantially similar elements used in the first embodiment.

Figure 10:
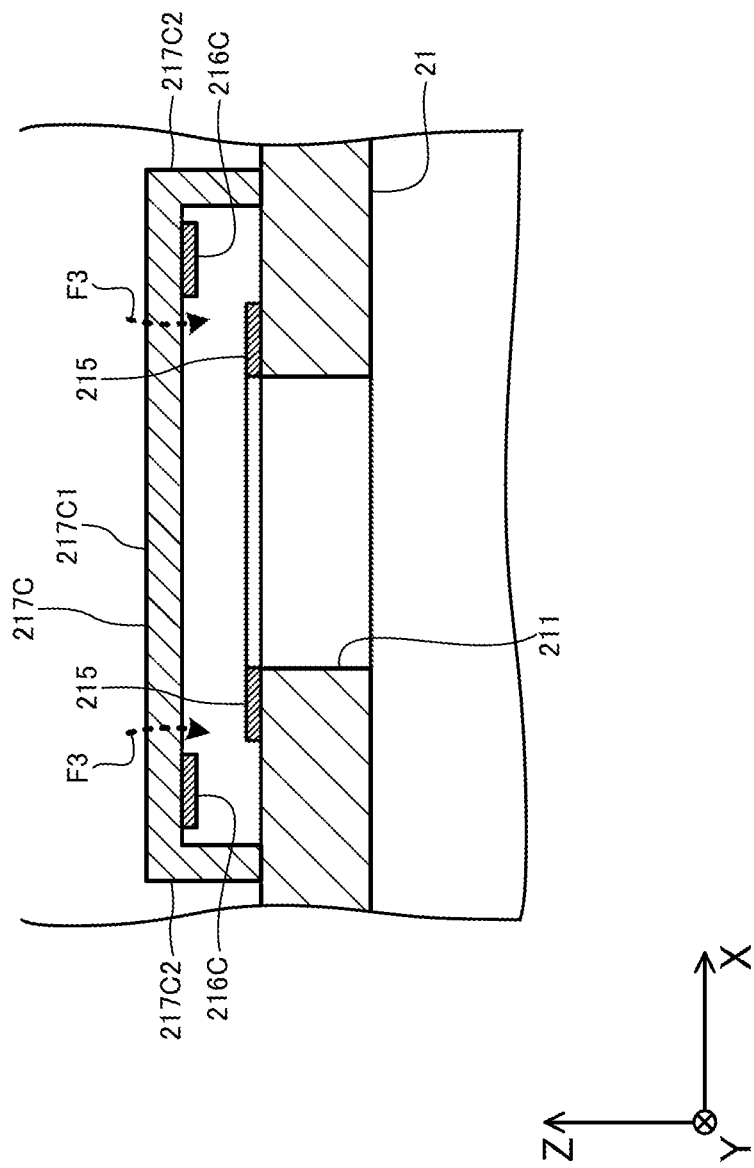
FIG. 10 is a partial cross-sectional view of an electronic device of a third embodiment, in an enlarged view of a valve member.
Figure 11:
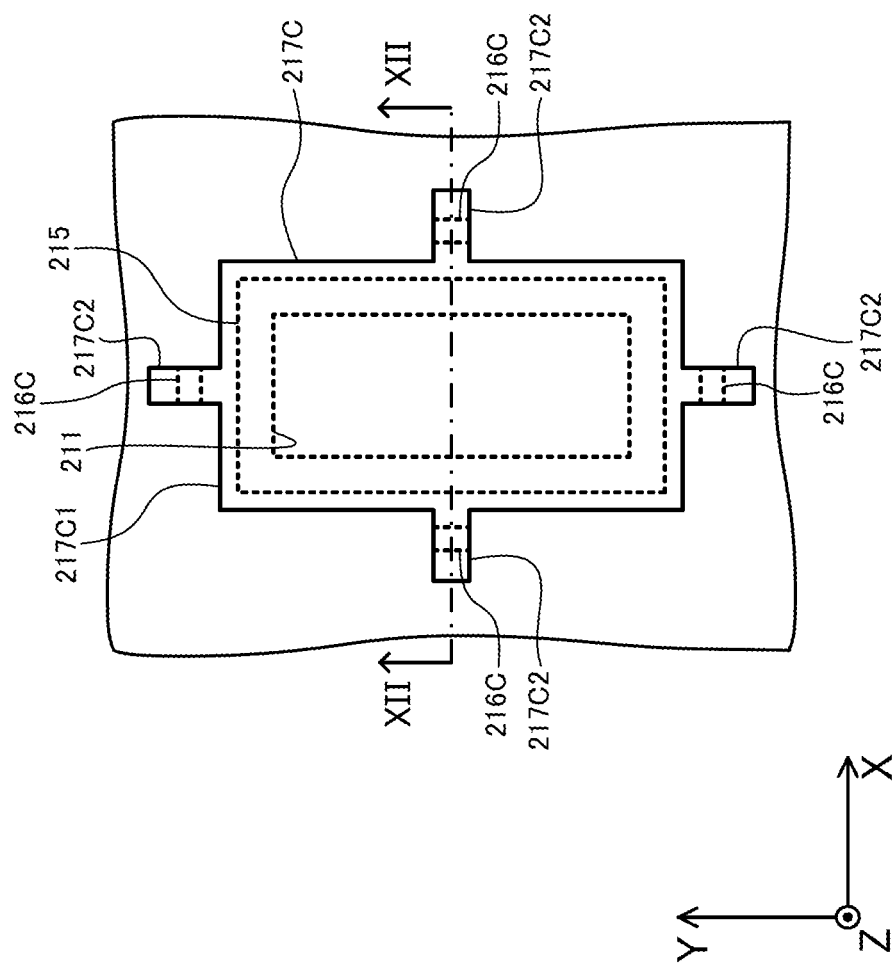
FIG. 11 is a partial top view of a main body of the third embodiment, in an enlarged view of the valve member.
Figure 12:
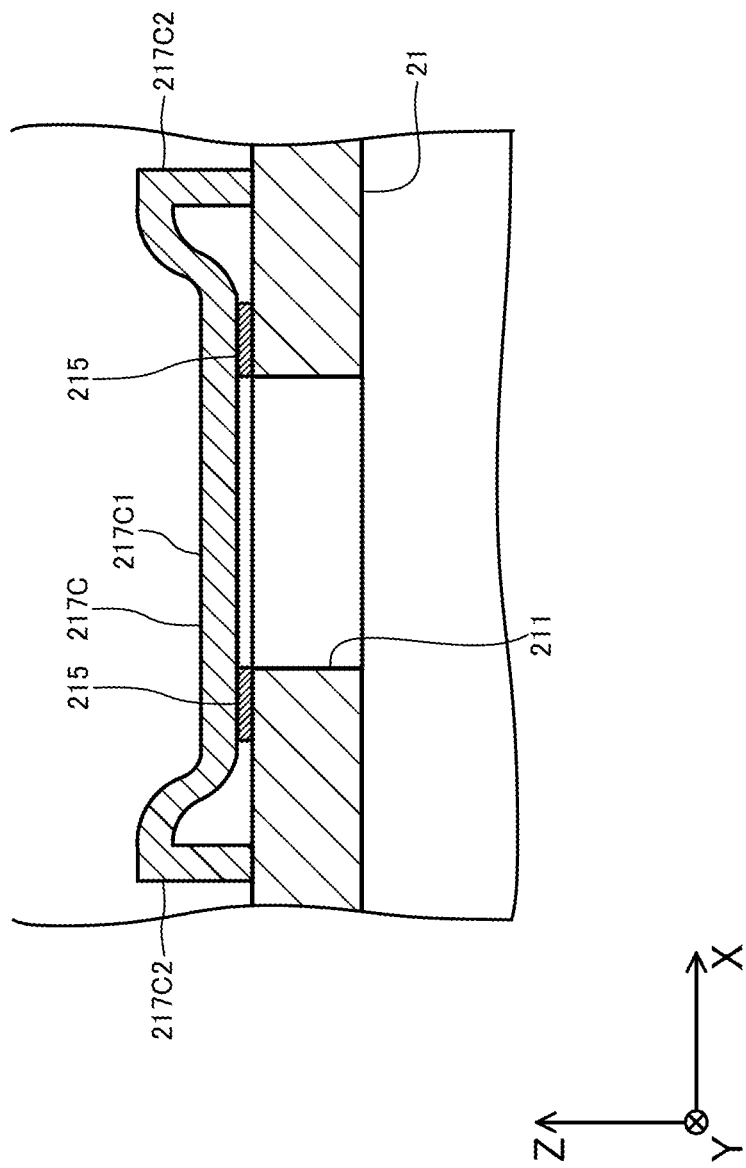
FIG. 12 is a partial cross-sectional view of the electronic device of the third embodiment once supports have been dissolved, in an enlarged view of the valve member.

Referring to FIGS. 10-12, an electronic device 1 of the third embodiment includes multiple (four in this example)

supports 216C and a valve member 217C, in place of the multiple supports 216 and the valve member 217 of the first embodiment.

FIG. 10 is a partial cross-sectional view of the electronic device 1 on the plane passing Line XII-XII in FIG. 11, in an enlarged view of the valve member 217C. FIG. 11 is an enlarged view of the area in the vicinity of the valve member 217C, when the main body 2 is viewed toward the negative direction of the Z axis. FIG. 12 is a partial cross-sectional view of the electronic device 1 once the supports 216C have been dissolved, on the plane passing Line XII-XII in FIG. 11, in an enlarged view of the valve member 217C.

The valve member 217C includes a base 217C1 and multiple (four in this example) legs 217C2.

The base 217C1 is in a planer shape that is parallel to the XY plane. The base 217C1 has a thickness between 2 μm and 200 μm, for example.

In this example, the base 217C1 is in a rectangular shape. The base 217C1 may be in any shape other than the rectangular shape (e.g., circular, oval, square, polygonal, or other shape). In this example, the long sides and the short sides of the base 217C1 extend along the Y axis and the X axis, respectively.

As illustrated in FIG. 11, in the X-axis direction, the base 217C1 extends from the negative direction side of the X axis relative to the valve seat 215, to the positive direction side of the X axis relative to the valve seat 215. In the Y-axis direction, the base 217C1 extends from the negative direction side of the Y axis relative to the valve seat 215, to the positive direction side of the Y axis relative to the valve seat 215.

In other words, when the main body 2 is viewed toward the negative direction of the Z axis, the base 217C1 covers the hole defined by the channel defining part 211, and the valve seat 215.

Each leg 217C2 is in a planer shape. In this example, each leg 217C2 has the same thickness as the thickness of the base 217C1. Each leg 217C2 may have a thickness different from the thickness of the base 217C1.

The four legs 217C2 extend from the respective sides of the base 217C1 in the four directions. In this example, the width of each leg 217C2 is smaller than the length of the side that adjoins the proximal end of the legs 217C2, of the sides of the base 217C1 in the four directions. In this example, the proximal end of each leg 217C2 is located at the center part of the side that adjoins that proximal end of the sides of the base 217C1 in the four directions.

Each leg 217C2 is bent. The distal end of each leg 217C2 contacts end face of the surfaces of the main body 2 on the positive direction side of the Z axis. In this example, the distal end of each leg 217C2 is secured to end face of the surfaces of the main body 2 on the positive direction side of the Z axis.

In the manner as described above, the multiple legs 217C2 support the base 217C1.

The part of each leg 217C2 between the bent portion of the leg 217C2 and the proximal end of the leg 217C2 is curved such that it is displaced further to the negative direction side of the Z axis as the part approaches the proximal end, in a state that the leg 217C2 is not elastically deformed. In this example, in a state that each leg 217C2 is not elastically deformed, the position of the proximal end of the leg 217C2 in the Z-axis direction is located at substantially the same position as that of the valve seat 215 (e.g., the position slightly on the negative direction side of the Z axis relative to the valve seat 215).

Each support 216C is made from material that is to be dissolved responsive to pH. In this example, each support 216C is made from material that is to be dissolved upon contacting a fluid with a pH lower than a predetermined threshold (e.g., pH of 5). Each support 216C is made from gastrosoluble material, for example. Each support 216C may be made from material that is dissolved upon contacting a fluid with a pH higher than a predetermined threshold (e.g., pH of 4). In this case, each support 216C may be made from enteric material, for example.

Each support 216C is in a planer shape that is parallel to the XY plane. Each support 216C has a thickness between 10 nm and 200 μm, for example.

As illustrated in FIG. 11, each support 216C has the same width as that of the legs 217C2. Each support 216C is disposed between the portion where the corresponding leg 217C2 bends and the proximal end of that leg 217C2.

Each support 216C is secured to the corresponding leg 217C2, with the entire end face of the surfaces of that support 216C on the positive direction side of the Z axis contacting the end face of the surface of the leg 217C2 on the negative direction side of the Z axis.

In the manner as described above, the proximal end of each leg 217C2 is located at substantially the same position as that of the bent portion of that leg 217C2, in the Z-axis direction. Therefore, in a state that the part of each leg 217C2 between the bent portion of the leg 217C2 and the proximal end of the leg 217C2 is not curved by being elastically deformed, the base 217C1 of the valve member 217C is supported by each support 216C.

In other words, as illustrated in FIG. 10, the part of each leg 217C2 between the bent portion of the leg 217C2 and the proximal end of the leg 217C2 undergoes the resiliency F3 generated against the elastic deformation. In this example, the resiliency F3 can be interpreted as the force to restore the part of each leg 217C2 between the bent portion of the leg 217C2 and the proximal end of the leg 217C2 to the curved state (in other words, the state where the position of the proximal end in the Z-axis direction is at substantially the same position as that of the valve seat 215). In this example, the resiliency F3 can also be interpreted as the force to displace the base 217C1 to the negative direction of the Z axis.

In the manner as described above, the base 217C1 of the valve member 217C is biased toward the valve seat 215, and is supported by the supports 216C at the location distant from the valve seat 215.

As illustrated in FIG. 12, once the supports 216C have been dissolved, the part of each leg 217C2 between the bent portion of the leg 217C2 and the proximal end of the leg 217C2 is restored to the curved state (in other words, the state where the position of the proximal end in the Z-axis direction is at substantially the same position as that of the valve seat 215) by the resiliency F3. As a result, the base 217C1 of the valve member 217C contacts the valve seat 215. In this example, the base 217C1 of the valve member 217C is pressed against the valve seat 215. As a result, the valve member 217C closes the channel communicating between the first space SP1 and the outside of the main body 2.

The supports 216C may have positions and sizes different from the positions and the sizes illustrated in FIG. 11. The number of the supports 216C may be any number other than four.

In this example, each support 216C is configured such that the supports 216C are dissolved completely once a fluid has been introduced to the first space SP1 through the hole defined by the channel defining part 211, when the pH external to the first space SP1 is lower than the above-described threshold.

The electronic device 1 of the third embodiment operates in the similar manner to the electronic device 1 of the first embodiment. Accordingly, effects and advantages similar to those of the electronic device 1 of the first embodiment are also achieved by the electronic device 1 of the third embodiment.

Fourth Embodiment

Next, an electronic device of a fourth embodiment will be described. The electronic device of the fourth embodiment is different from the electronic device of the first embodiment in that volume changing bodies that undergo volume changes responsive to pH are used, in place of the supports that are to be dissolved responsive to pH. Descriptions will be given focusing on that difference. In the descriptions of the fourth embodiment, elements denoted by like reference symbols denote the same or substantially similar elements used in the first embodiment.

Figure 13:
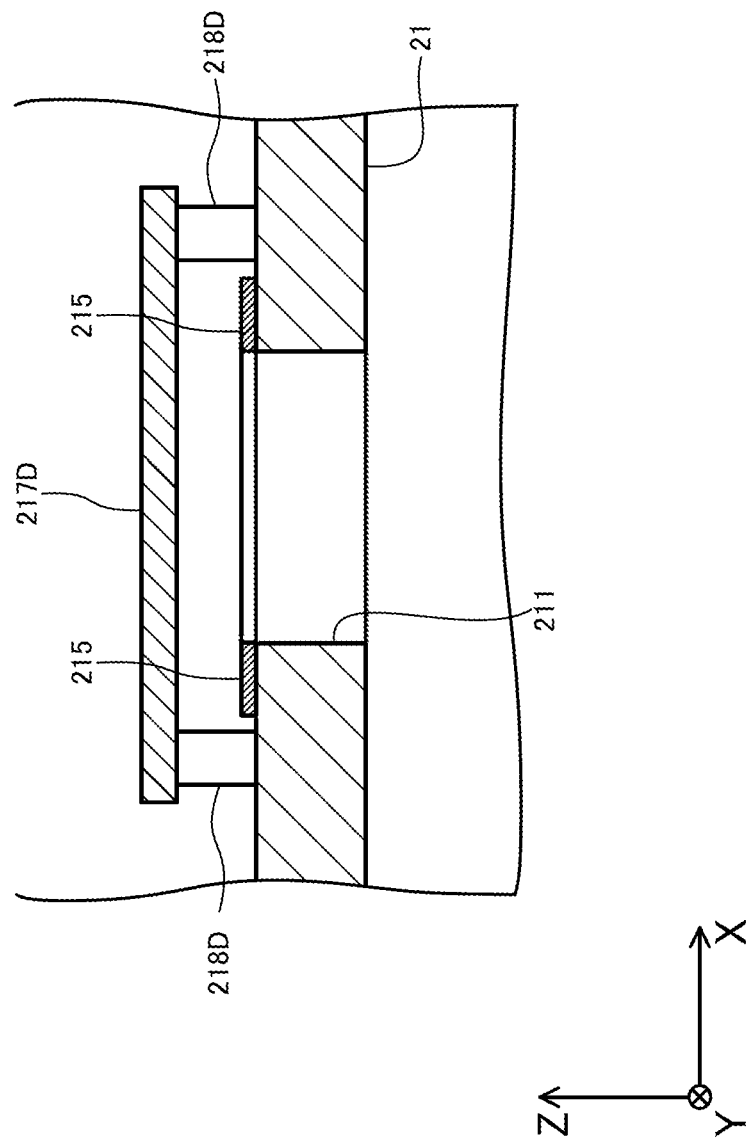
FIG. 13 is a partial cross-sectional view of an electronic device of the fourth embodiment, in an enlarged view of a valve member.
Figure 14:
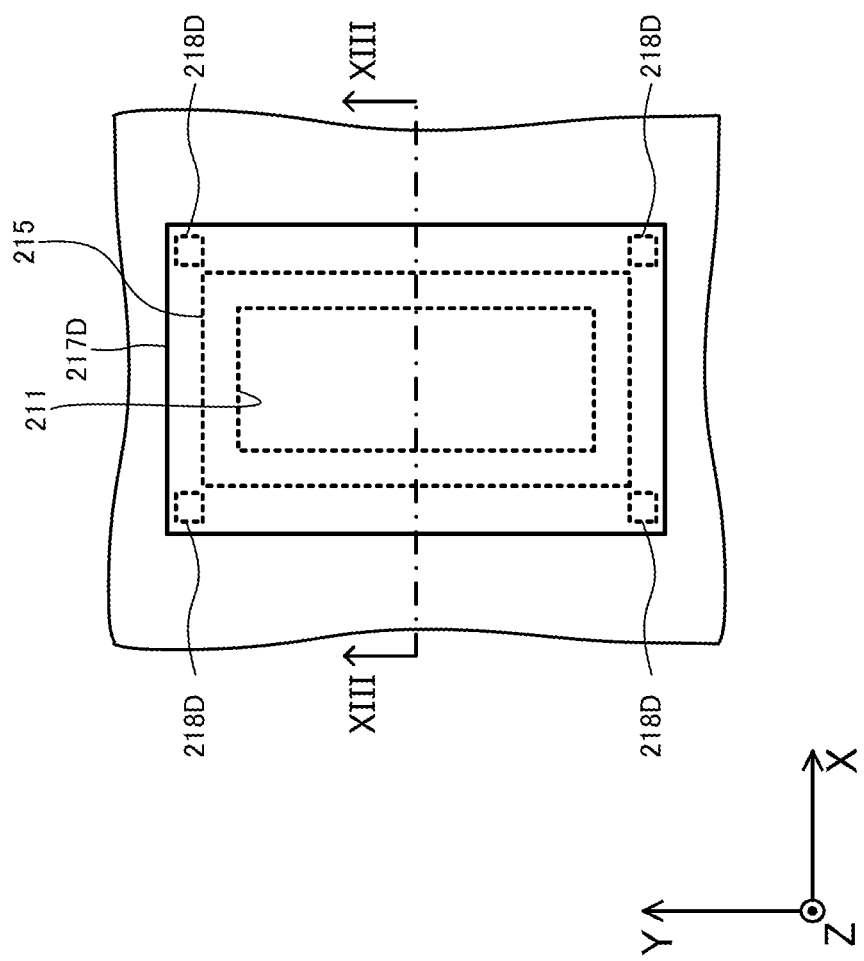
FIG. 14 is a partial top view of a main body of the fourth embodiment, in an enlarged view of the valve member.
Figure 15:
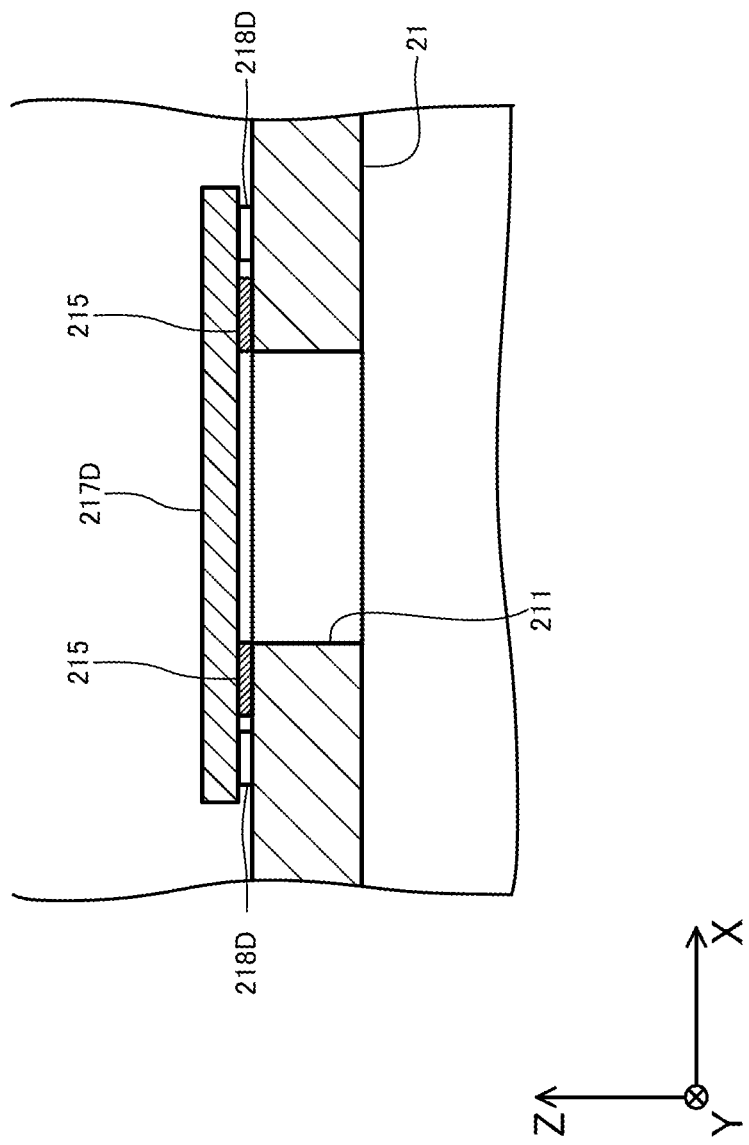
FIG. 15 is a partial cross-sectional view of the electronic device of the fourth embodiment once volume changing bodies have shrunk, in an enlarged view of the valve member.

Referring to FIGS. 13-15, an electronic device 1 of the fourth embodiment includes a valve member 217D and multiple (four in this example) volume changing bodies 218D, in place of the multiple supports 216 and the valve member 217 of the first embodiment.

FIG. 13 is a partial cross-sectional view of the electronic device 1 on the plane passing Line XIII-XIII in FIG. 14, in an enlarged view of the valve member 217D. FIG. 14 is an enlarged view of the area in the vicinity of the valve member 217D, when the main body 2 is viewed toward the negative direction of the Z axis. FIG. 15 is a partial cross-sectional view of the electronic device 1 when the volume changing bodies 218D shrink, on the plane passing Line XIII-XIII in FIG. 14, in an enlarged view of the valve member 217D.

The valve member 217D is in a planer shape that is parallel to the XY plane. The valve member 217D has a thickness between 2 μm and 200 μm, for example.

In this example, the valve member 217D is in a rectangular shape. The valve member 217D may be in any shape other than the rectangular shape (e.g., circular, oval, square, polygonal, or other shape). In this example, the long sides and the short sides of the valve member 217D extend along the Y axis and the X axis, respectively.

As illustrated in FIG. 14, in the X-axis direction, the valve member 217D extends from the negative direction side of the X axis relative to the valve seat 215, to the positive direction side of the X axis relative to the valve seat 215. In the Y-axis direction, the valve member 217D extends from the negative direction side of the Y axis relative to the valve seat 215, to the positive direction side of the Y axis relative to the valve seat 215.

In other words, when the main body 2 is viewed toward the negative direction of the Z axis, the valve member 217D covers the hole defined by the channel defining part 211, and the valve seat 215.

Each volume changing body 218D is made from material undergoes a volume change responsive to pH. In this example, each volume changing body 218D is made from material which undergoes a volume reduction (in other words, shrinks) upon contacting a fluid with a pH lower than a predetermined threshold (e.g., pH of 5). Each volume changing body 218D may be made from material that shrinks upon contacting a fluid with a pH higher than a predetermined threshold (e.g., pH of 4). In this example, each volume changing body 218D is made from pH-sensitive gel.

The pH-sensitive gel contains, as the main component, at least one of: anion gel having acidic functional group, such as carboxyl group, in macromolecule chain; cation gel having basic functional group in macromolecule chain; and amphoteric gel having both acidic functional group and basic functional group in macromolecule chain, for example. The pH-sensitive gel is an acrylamide-acrylic acid copolymer, for example.

Each volume changing body 218D is in a pillar shape extending along the Z axis. In this example, the bottom of each volume changing body 218D is in a rectangular shape. The bottom of each volume changing body 218D may be in any shape other than the rectangular shape (e.g., circular, oval, square, polygonal, or other shape).

Each volume changing body 218D has a length in the Z-axis direction (in other words, the height of the volume changing body 218D) between 10 μm and 1 mm, for example. In this example, the height of each volume changing body 218D is greater than the thickness of the valve seat 215.

In this example, the length of each volume changing body 218D in the Z-axis direction becomes equal to or smaller than the thickness of the valve seat 215 once it has been shrunken completely.

The end face of each volume changing body 218D on the negative direction side of the Z axis is secured to end face of the surfaces of the main body 2 on the positive direction side of the Z axis. The end face of each volume changing body 218D on the positive direction side of the Z axis is secured to the end face of the surfaces of the valve member 217D on the negative direction side of the Z axis.

As illustrated in FIG. 14, each volume changing body 218D is disposed between the outer edge of the valve seat 215 and the outer edge of the valve member 217D on the XY plane. In this example, the four volume changing bodies 218D are disposed at the respective four corners of the valve member 217D, in the outer periphery of the valve seat 215. In other words, the four volume changing bodies 218D are separated from each other.

In the manner as described above, the valve member 217D is supported by the main body 2, in a state that contacting the volume changing bodies 218D.

As illustrated in FIG. 15, when the volume changing bodies 218D shrink, the volume changing bodies 218D pull the valve member 217D in the negative direction of the Z axis, thereby causing the valve member 217D to contact the valve seat 215. In this example, the valve member 217D is pressed against the valve seat 215. As a result, the valve member 217D closes the channel communicating between the first space SP1 and the outside of the main body 2.

In this example, each volume changing body 218D is configured such that that volume changing body 218D completely shrinks once a fluid has been introduced to the first space SP1 through the hole defined by the channel defining part 211, when the pH external to the first space SP1 is lower than the above-described threshold.

In this example, the valve seat 215, the valve member 217D, and the volume changing bodies 218D correspond to a valve that closes the channel communicating between the first space SP1 and the outside of the main body 2 responsive to pH.

The volume changing bodies 218D may have positions and sizes different from the position and the size illustrated in FIG. 14. Each volume changing body 218D may be located in predetermined regions of the outer periphery of the valve seat 215, for example.

The number of the volume changing bodies 218D may be any number other than four.

In the electronic device 1 of the fourth embodiment, each volume changing body 218D completely shrinks once the gastric fluid has been introduced to the first space SP1. This causes the volume changing bodies 218D to pull the valve member 217D in the negative direction of the Z axis, and thus the valve member 217D is pressed against the valve seat 215. As a result, the valve member 217D closes the channel communicating between the first space SP1 and the outside of the main body 2.

This can prevent any matters other than the gastric fluid (e.g., fluid with pH different from that of gastric fluid, solid matter, or the like) from entering the first space SP1. As a result, a decline in the power output can be suppressed.

As set forth above, the electronic device 1 of the fourth embodiment operates similarly to the electronic device 1 of the first embodiment, except for the difference in the valve mechanisms. Accordingly, effects and advantages similar to those of the electronic device 1 of the first embodiment are also achieved by the electronic device 1 of the fourth embodiment.

Furthermore, in the electronic device 1 of the fourth embodiment, the valve includes the valve seat 215, the volume changing bodies 218D that undergo volume changes responsive to pH, and the valve member 217D that is supported by the main body 2 with contacting the volume changing bodies 218D, and closes the channel by contacting the valve seat 215 in response to the change in the volumes of the volume changing bodies 218D.

In accordance with the above configuration, the volume changing bodies 218D undergo volume changes in response to the change in pH. This causes the valve member 217D to contact the valve seat 215. As a result, the channel communicating between the first space SP1 and the outside of the main body 2 is closed.

At least a part of the main body 2 may be made from any of optically transmissive material such that the volume changing bodies 218D are irradiated with light through at least that part of the main body 2. The optically transmissive material is glass, for example. In this case, a member made from glass and a member made from silicon (Si) may be bonded with anodic bonding.

In accordance with the above configuration, the volume changing bodies 218D can be formed by irradiating with light through the part of the main body 2, which is made from the optically transmissive material. This facilitates manufacturing of the electronic device 1 having the volume changing bodies 218D disposed therein.

Fifth Embodiment

Next, an electronic device of a fifth embodiment will be described. The electronic device of the fifth embodiment is different from the electronic device of the first embodiment in terms of the main body and the valve member. Descriptions will be given focusing on that difference. In the descriptions of the fifth embodiment, elements denoted by like reference symbols denote the same or substantially similar elements used in the first embodiment.

Figure 16:
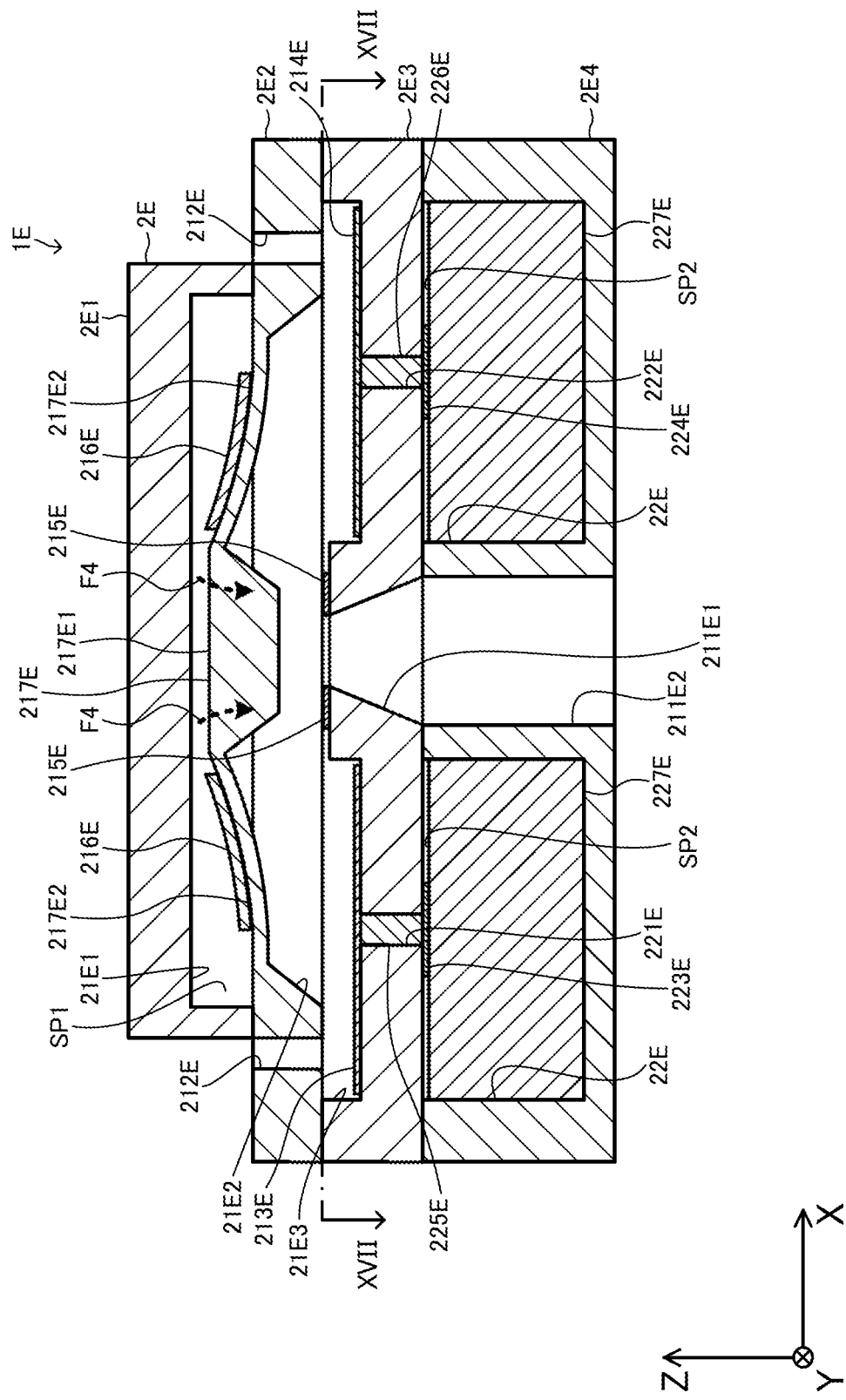
FIG. 16 is a cross-sectional view of an electronic device of a fifth embodiment.

Referring to FIG. 16, the electronic device 1E of the fifth embodiment includes a main body 2E in place of the main body 2 of the first embodiment. In FIG. 16 and FIGS. 17-19 described later, illustration of the film 3 is omitted.

In this example, the main body 2E is made from silicon (Si). At least a part of the main body 2E may be made from glass. In this example, the main body 2E includes a first structure 2E1, a second structure 2E2, a third structure 2E3, and a fourth structure 2E4.

Each structure 2E1-2E4 is in a pillar shape extending along the Z axis. In this example, the bottom of each structure 2E1-2E4 is in a square shape. The bottom of each structure 2E1-2E4 may be in any shape other than the square shape (e.g., circular, oval, rectangular, polygonal, or any other shape).

The bottoms of the second structure 2E2, the third structure 2E3, and the fourth structure 2E4 are in the same shape. The outer edge of the bottom of the first structure 2E1 is located inside the outer edge of the bottom of the second structure 2E2. The central axes of the four structures 2E1-2E4 coincide with each other.

The first structure 2E1, the second structure 2E2, the third structure 2E3, and the fourth structure 2E4 are stacked. The end face of the first structure 2E1 on the negative direction side of the Z axis contacts the end face of the second structure 2E2 on the positive direction side of the Z axis. The end face of the second structure 2E2 on the negative direction side of the Z axis contacts the end face of the third structure 2E3 on the positive direction side of the Z axis. The end face of the third structure 2E3 on the negative direction side of the Z axis contacts the end face of the fourth structure 2E4 on the positive direction side of the Z axis.

The first structure 2E1 includes a recess 21E1. The recess 21E1 defines a space adjoining the second structure 2E2 on the end face of the first structure 2E1 on the negative direction side of the Z axis. In other words, the recess 21E1 opens at the end face of the first structure 2E1 on the negative direction side of the Z axis.

The space defined by the recess 21E1 is in a pillar shape extending along the Z axis. In this example, the bottom of the space defined by the recess 21E1 is in a square shape. The bottom of the space defined by the recess 21E1 may be in any shape other than the square shape (e.g., circular, oval, rectangular, polygonal, or any other shape).

The second structure 2E2 includes a through-hole part 21E2. The through-hole part 21E2 defines a hole passing through the second structure 2E2 in the Z-axis direction.

The hole defined by the through-hole part 21E2 is in a pillar shape extending along the Z axis. In this example, the bottom of the hole defined by the through-hole part 21E2 is in a square shape. The bottom of the hole defined by the through-hole part 21E2 may be in any shape other than the square shape (e.g., circular, oval, rectangular, polygonal, or any other shape).

In this example, the bottom of the hole defined by the through-hole part 21E2 is in the same shape as that of the bottom of the space defined by the recess 21E1. In this example, the central axis of the hole defined by the through-hole part 21E2 coincides with the central axis of the space defined by the recess 21E1.

The third structure 2E3 includes a recess 21E3. The recess 21E3 defines a space adjoining the second structure 2E2 on the end face of the third structure 2E3 on the positive direction side of the Z axis. In other words, the recess 21E3 opens at the end face of the third structure 2E3 on the positive direction side of the Z axis. The recess 21E3 is located at the end part of the third structure 2E3 on the XY plane (in other words, the part other than the center part of the third structure 2E3 on the XY plane).

The space defined by the recess 21E3 is in a pillar shape extending along the Z axis. In this example, the bottom of the space defined by the recess 21E3 is in a square shape having an absence in a rectangular shape at the center part of the square shape. The bottom of the space defined by the recess 21E3 may be in any shape other than the square shape (e.g., circular, oval, rectangular, polygonal, or any other shape).

In this example, the central axis of the space defined by the recess 21E3 coincides with the central axis of the hole defined by the through-hole part 21E2.

The hole defined by the through-hole part 21E2 contacts each of the space defined by the recess 21E1 and the space defined by the recess 21E3. In this example, the space defined by the recess 21E1, the hole defined by the through-hole part 21E2, and the space defined by the recess 21E3 constitute the first space SP1 defined inside the main body 2E.

The fourth structure 2E4 includes a recess 22E. The recess 22E defines a space adjoining the third structure 2E3 on the end face of the fourth structure 2E4 on the positive direction side of the Z axis. In other words, the recess 22E opens at the end face of the fourth structure 2E4 on the positive direction side of the Z axis. The recess 22E is located at the end part of the fourth structure 2E4 on the XY plane (in other words, the part other than the center part of the fourth structure 2E4 on the XY plane).

The space defined by the recess 22E adjoins the end face of the third structure 2E3 on the negative direction side of the Z axis. In this example, the end face of the third structure 2E3 on the negative direction side of the Z axis, and the space defined by the recess 22E constitute the second space SP2 defined inside the main body 2E.

In this example, the first structure 2E1, the second structure 2E2, and the third structure 2E3 constitute a first layer. Additionally, in this example, the fourth structure 2E4 constitute a second layer different from the first layer.

The electronic device 1E may include a retaining member made from porous material in the first space SP1. In this case, the porous material is preferably hydrophilic.

Figure 17:
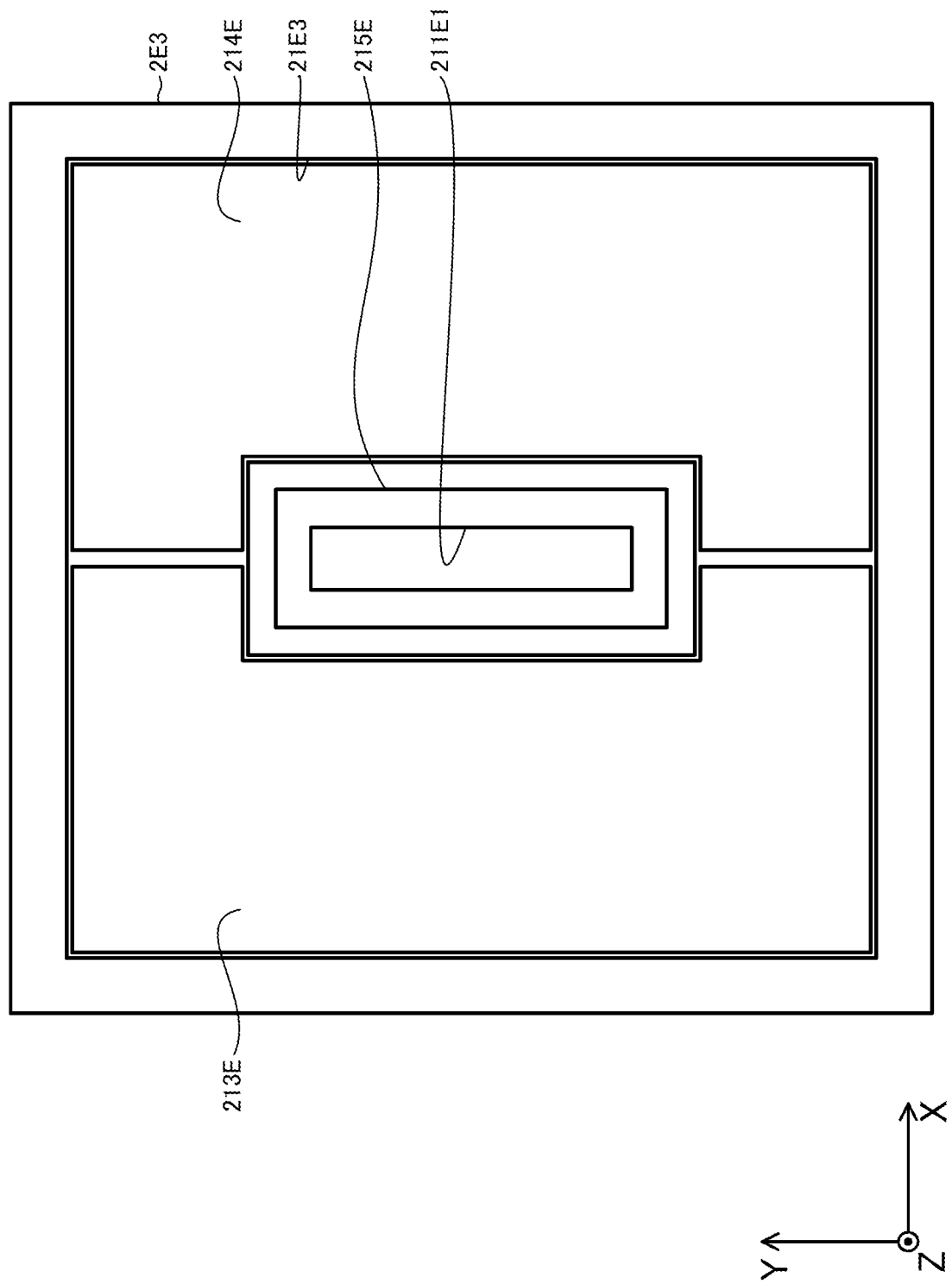
FIG. 17 is a cross-sectional view of the electronic device of the fifth embodiment.

As illustrated in FIGS. 16 and 17, the third structure 2E3 includes a first channel defining part 211E1. FIG. 17 illustrates the cross-section of the electronic device 1E on the plane passing Line XVII-XVII in FIG. 16. The fourth structure 2E4 includes a second channel defining part 211E2. The second structure 2E2 includes multiple (16 in this example) through-hole parts 212E.

The first channel defining part 211E1 defines a hole that passes through the center part of the third structure 2E3 on the XY plane in the Z-axis direction, and is shaped to be a part of a cone extending along the Z axis.

In this example, the bottom of the hole defined by the first channel defining part 211E1 is in a rectangular shape. The bottom of the hole defined by the first channel defining part 211E1 may be in any shape other than the rectangular shape (e.g., circular, oval, square, polygonal, or other shape). The hole defined by the first channel defining part 211E1 may be in a pillar shape.

The long sides of the bottom of the hole defined by the first channel defining part 211E1 have a length between 200 µm and 20 mm, for example. The short sides of the bottom of the hole defined by the first channel defining part 211E1 have a length between 100 µm and 10 mm, for example.

The long sides and the short sides of the bottom of the hole defined by the first channel defining part 211E1 extend along the Y axis and the X axis, respectively.

The second channel defining part 211E2 defines a hole that passes through the center part of the fourth structure 2E4 on the XY plane in the Z-axis direction, and is in a pillar shape extending along the Z axis.

In this example, the bottom of the hole defined by the second channel defining part 211E2 is in a rectangular shape. The bottom of the hole defined by the second channel defining part 211E2 may be in any shape other than the rectangular shape (e.g., circular, oval, square, polygonal, or other shape). The hole defined by the second channel defining part 211E2 may be shaped to be a part of a cone.

In this example, the bottom of the hole defined by the second channel defining part 211E2 is in the same shape as that of the bottom of the hole defined by the first channel defining part 211E1 on the negative direction side of the Z axis. The central axis of the hole defined by the second channel defining part 211E2 coincides with the central axis of the hole defined by the first channel defining part 211E1.

In this example, the hole defined by the first channel defining part 211E1 and the hole defined by the second channel defining part 211E2 communicate between the first space SP1 and the outside of the main body 2E. In this example, the hole defined by the first channel defining part 211E1 and the hole defined by the second channel defining part 211E2 correspond to a channel.

In this example, the first channel defining part 211E1, the second channel defining part 211E2, the recess 21E1, the through-hole part 21E2, and the recess 21E3 are coated with hydrophilic films. The hydrophilic films are made from silicon dioxide, for example.

Figure 18:
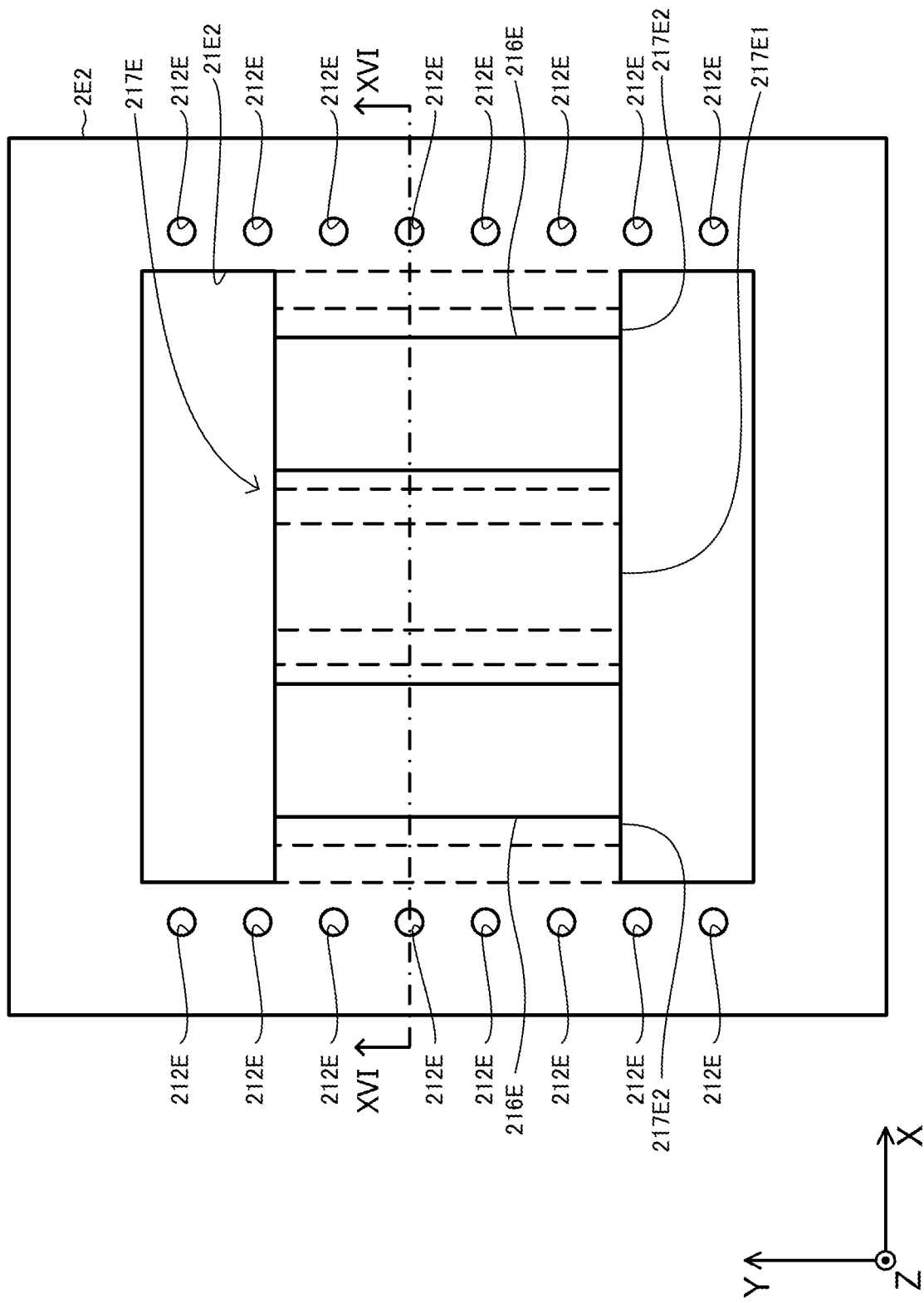
FIG. 18 is a top view of a second structure of the fifth embodiment.

As illustrated in FIGS. 16 and 18, each through-hole part 212E defines a hole that passes through the second structure 2E2 in the Z-axis direction, and is in a pillar shape extending along the Z axis. FIG. 18 is a diagram of the second structure 2E2 when viewed toward the negative direction of the Z axis.

In this example, the bottom of the hole defined by each through-hole part 212E is in a circular shape. The bottom of the hole defined by each through-hole part 212E may be in any shape other than the circular shape (e.g., oval, square, rectangular, polygonal, or other shape). The hole defined by each through-hole part 212E may be shaped to be a part of a cone.

In this example, the area of the bottom of the hole defined by each through-hole part 212E is smaller than the area of the bottom of the hole defined by the first channel defining part 211E1. The bottom of the hole defined by each through-hole part 212E has a diameter between 2 µm and 200 µm, for example.

As illustrated in FIG. 16, the through-hole parts 212E are located outside the outer edge of the first structure 2E1 on the XY plane. In this example, as illustrated in FIG. 18, the through-hole parts 212E are arranged in both ends of the second structure 2E2 in the X-axis direction. The multiple through-hole parts 212E are spaced apart at regular intervals along the Y axis.

In the manner described above, the hole defined by each through-hole part 212E communicates between the first space SP1 and the outside of the main body 2E.

The number of the through-hole parts 212E may be any number other than eight.

In this example, each through-hole part 212E is covered with a water-repellent film. The water-repellent film is made from fluorocarbon resin (e.g., resin containing polytetrafluoroethylene as the main component), for example.

Further, the electronic device 1E includes a first electrode 213E, a second electrode 214E, a valve seat 215E, multiple (two in this example) supports 216E, and a valve member 217E, in place of the first electrode 213, the second electrode 214, the valve seat 215, the multiple supports 216, and the valve member 217 of the first embodiment.

In this example, the main body 2E, the film 3, the first electrode 213E, the second electrode 214E, the valve seat 215E, the multiple supports 216E, and the valve member 217E of the electronic device 1E constitute a battery. In this example, the first electrode 213E and the second electrode 214E may also be referred to as the pair of electrodes.

In this example, the first electrode 213E is made from magnesium. The first electrode 213E may be made from any material other than magnesium (e.g., zinc, alloy, or the like). Alternatively, the first electrode 213E may be a film stack where multiple layers respectively made from different materials are stacked.

The first electrode 213E is in a planer shape that is parallel to the XY plane. The first electrode 213E has a thickness between 100 nm and 2 mm, for example. In this example, the first electrode 213E is in a rectangular shape of which the long sides and the short sides extend along the Y axis and the X axis, respectively. The first electrode 213E has a recess on the long side on the positive direction side of the X axis. The first electrode 213E may be in any shape other than the rectangular shape (e.g., circular, oval, square, polygonal, or other shape).

The first electrode 213E contacts the end face of the recess 21E3 on the negative direction side of the Z axis.

In this example, the area of the first electrode 213E is slightly smaller than the half of the area of the end face of the recess 21E3 on the negative direction side of the Z axis.

In this example, the second electrode 214E is made from platinum. The second electrode 214E may be made from any material other than platinum (e.g., copper chloride (CuCl), silver chloride (AgCl), alloy, or the like). Alternatively, the second electrode 214E may be a film stack where multiple layers respectively made from different materials are stacked.

The second electrode 214E is in a planer shape that is parallel to the XY plane. The second electrode 214E has a thickness between 10 nm and 2 mm, for example. In this example, the second electrode 214E is in a rectangular shape of which the long sides and the short sides extend along the Y axis and the X axis, respectively. The second electrode 214E has a recess on the long side on the negative direction side of the X axis. The second electrode 214E may be in any shape other than the rectangular shape (e.g., circular, oval, square, polygonal, or other shape).

The second electrode 214E contacts the end face of the recess 21E3 on the negative direction side of the Z axis.

In this example, the area of the second electrode 214E is slightly smaller than the half of the area of the end face of the recess 21E3 on the negative direction side of the Z axis.

In this example, the first electrode 213E is located on the negative direction side of the X axis relative to the center in the X-axis direction, in the end face of the recess 21E3 on the negative direction side of the Z axis. In this example, the second electrode 214E is located on the positive direction side of the X axis relative to the center in the X-axis direction, in the end face of the recess 21E3 on the negative direction side of the Z axis. In other words, the first electrode 213E and the second electrode 214E are separated from each other.

In this example, the materials for the first electrode 213E and the second electrode 214E are selected such that electric power is generated by a gastric fluid functioning as an electrolyte once the gastric fluid has been introduced to the first space SP1.

In this example, the valve seat 215E is made from metal. The valve seat 215E may be made from material other than metal (e.g., resin containing polyimide as a main component and the like).

The valve seat 215E is in a planer shape that is parallel to the XY plane. The valve seat 215E has a thickness between 10 nm and 10 μm, for example. The valve seat 215E contacts the end face of the surfaces of the third structure 2E3 on the positive direction side of the Z axis.

The valve seat 215E has a predetermined width, and extends along the edge of the first channel defining part 211E1 on the positive direction side of the Z axis. The edge part of the first channel defining part 211E1 on the positive direction side of the Z axis may also be referred to as the outer edge of the end face of the hole defined by the first channel defining part 211E1 on the positive direction side of the Z axis. The edge of the first channel defining part 211E1 on the positive direction side of the Z axis may also be referred to as the outer edge of the opening of the hole defined by the first channel defining part 211E1, in the end face of the surfaces of the third structure 2E3 on the positive direction side of the Z axis.

In other words, the shape of the valve seat 215E on the XY plane coincides with the shape of the end face of the hole defined by the first channel defining part 211E1 on the positive direction side of the Z axis, and has a hole passing through in the Z-axis direction.

As illustrated in FIG. 18, the valve member 217E extends from the end face of the through-hole part 21E2 on the negative direction side of the X axis, to the end face of the through-hole part 21E2 on the positive direction side of the X axis. The length of the valve member 217E in the Y-axis direction is smaller than the length in the Y-axis direction of the end face of the through-hole part 21E2 in the X-axis direction, and is longer than the length in the Y-axis direction of the end face of the hole defined by the first channel defining part 211E1 on the positive direction side of the Z axis.

Figure 19:
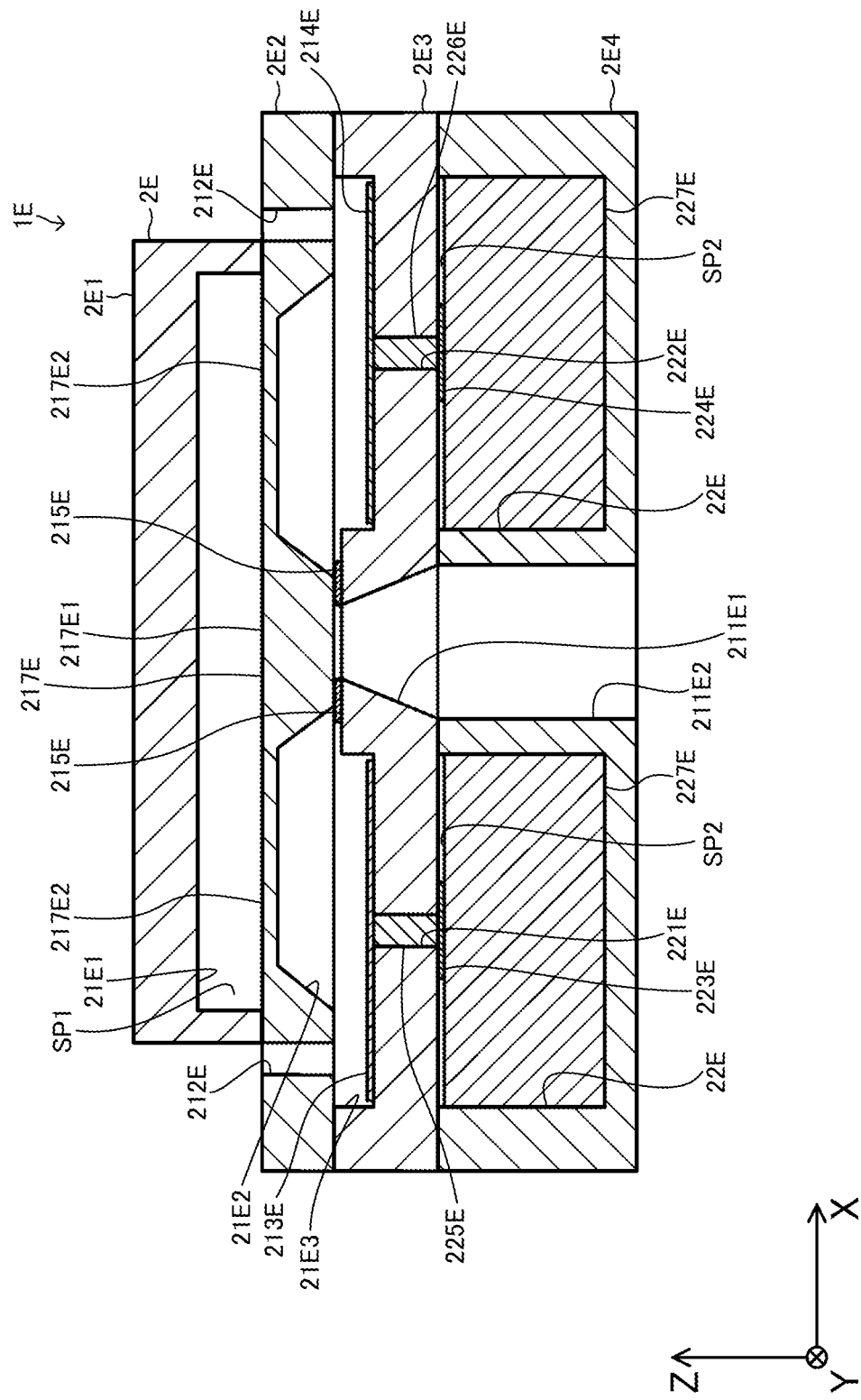
FIG. 19 is a cross-sectional view of the electronic device of the fifth embodiment, once supports have been dissolved.

As illustrated in FIGS. 16, 18, and 19, the valve member 217E includes a base 217E1 and multiple (two in this example) arms 217E2. FIG. 19 is a cross-sectional view of the electronic device 1E on the plane passing Line XVI-XVI in FIG. 18, once the supports 216E have been dissolved.

The base 217E1 constitutes the center part of the valve member 217E in the X-axis direction. The length of the base 217E1 in the Z-axis direction (in other words, thickness of the base 217E1) is equal to the length of the second structure 2E2 in the Z-axis direction (in other words, thickness of the second structure 2E2). The length of the base 217E1 in the X-axis direction is slightly longer than the length in the X-axis direction of the end face of the hole defined by the first channel defining part 211E1 on the positive direction side of the Z axis.

In other words, when the second structure 2E2 is viewed toward the negative direction of the Z axis, the base 217E1 of the valve member 217E covers the end face of the hole defined by the first channel defining part 211E1 on the positive direction side of the Z axis, and also covers at least a part of the valve seat 215E.

The two arms 217E2 constitute both of the end parts of the valve member 217E in the X-axis direction (in other words, the parts of the valve member 217E other than the base 217E1), respectively. In other words, the two arms 217E2 support the base 217E1.

The length of each arm 217E2 in the Z-axis direction (in other words, thickness of the arm 217E2) is smaller than the thickness of the second structure 2E2. Each arm 217E2 constitutes a part of the end face of the second structure 2E2 on the positive direction side of the Z axis.

As illustrated in FIG. 19, each arm 217E2 is in a planer shape that is parallel to the XY plane while not being elastically deformed.

Each support 216E is made from material that is to be dissolved responsive to pH. In this example, each support 216E is made from material that is to be dissolved upon contacting a fluid with a pH lower than a predetermined threshold (e.g., pH of 5). Each support 216E is made from gastrosoluble material, for example. Each support 216E may be made from material that is dissolved upon contacting a fluid with a pH higher than a predetermined threshold (e.g., pH of 4). In this case, each support 216E may be made from enteric material, for example.

Each support 216E is in a planer shape. Each support 216E has a thickness between 10 nm and 200 μm, for example.

As illustrated in FIGS. 16 and 18, each support 216E is secured to the valve member 217E, with the entire end face of the surfaces of that support 216E on the negative direction side of the Z axis contacting the end face of the surfaces of the valve member 217E on the positive direction side of the Z axis. In this example, the two supports 216E are secured to the respective two arms 217E2.

In the X-axis direction, each support 216E extends from the vicinity of the edge of the arms 217E2 on the negative direction side of the X axis, to the vicinity of the edge of the arms 217E2 on the positive direction side of the X axis. In the Y-axis direction, each support 216E extends from the edge of the valve member 217E on the negative direction side of the Y axis, to the edge of the valve member 217E on the positive direction side of the Y axis.

As illustrated in FIG. 16, the support 216E on the negative direction side of the X axis of the two supports 216E is in a curved state such that a portion of the support 216E is displaced further to the positive direction side of the Z axis as the portion approaches, in the X-axis direction, the end of the support 216E on the positive direction side of the X axis. The support 216E on the positive direction side of the X axis of the two supports 216E is in a curved state such that a portion of the support 216E is displaced further to the positive direction side of the Z axis as the portion approaches, in the X-axis direction, the end of the support 216E on the negative direction side of the X axis.

In other words, each support 216E is in a curved state such that a portion of the support 216E is displaced further to the positive direction side of the Z axis as the portion approaches, in the X-axis direction, the center part of the valve member 217E in the X-axis direction (in other words, the base 217E1).

As a result, the valve member 217E is supported by each support 216E, with being curved by an elastic deformation, such that a portion of the valve member 217E is displaced further to the positive direction side of the Z axis as the portion approaches, in the X-axis direction, the center part of the valve member 217E in the X-axis direction.

In other words, as illustrated in FIG. 16, the arms 217E2 undergo the resiliency F4 generated against the elastic deformation. In this example, the resiliency F4 can be interpreted as the force to restore the arms 217E2 to its unbent state (in other words, the arms 217E2 to be parallel to the XY plane). In this example, the resiliency F4 can also be interpreted as the force to displace the center part of the valve member 217E (in other words, the base 217E1) to the negative direction of the Z axis.

In the manner as described above, the base 217E1 of the valve member 217E is biased toward the valve seat 215E, and is supported by the supports 216E at the location distant from the valve seat 215E.

As illustrated in FIG. 19, once the supports 216E have been dissolved, the arms 217E2 is restored to be parallel to the XY plane by the resiliency F4. Thus causes the base 217E1 of the valve member 217E to contact the valve seat 215E. In this example, the base 217E1 of the valve member 217E is pressed against the valve seat 215E. As a result, the valve member 217E closes the channel communicating between the first space SP1 and the outside of the main body 2E.

The supports 216E may have positions and sizes different from the positions and the sizes illustrated in FIG. 18. The number of the supports 216E may be any number other than two.

In this example, each support 216E is configured such that each support 216E are dissolved completely, once a fluid has been introduced to the first space SP1 through the hole defined by the first channel defining part 211E1 and through the hole defined by the second channel defining part 211E2, when the pH external to the first space SP1 is lower than the above-described threshold.

Furthermore, the electronic device 1E includes the first through-hole part 221E, the second through-hole part 222E, the first terminal 223E, the second terminal 224E, the first conductor 225E, the second conductor 226E, and the circuit 227E that are configured similarly to the first through-hole part 221, the second through-hole part 222, the first terminal 223, the second terminal 224, the first conductor 225, the second conductor 226, and the circuit 227 of the first embodiment.

The electronic device 1E of the fifth embodiment operates in the similar manner to the electronic device 1 of the first embodiment. Accordingly, effects and advantages similar to those of the electronic device 1 of the first embodiment are also achieved by the electronic device 1E of the fifth embodiment.

Sixth Embodiment

Next, an electronic device of the sixth embodiment will be described. The electronic device of the sixth embodiment is different from the electronic device of the fifth embodiment in that volume changing bodies that undergo volume changes responsive to pH are used in place of the supports that are to be dissolved responsive to pH. Descriptions will be given focusing on that difference. In the descriptions of the sixth embodiment, elements denoted by like reference symbols denote the same or substantially similar elements used in the fifth embodiment.

Figure 20:
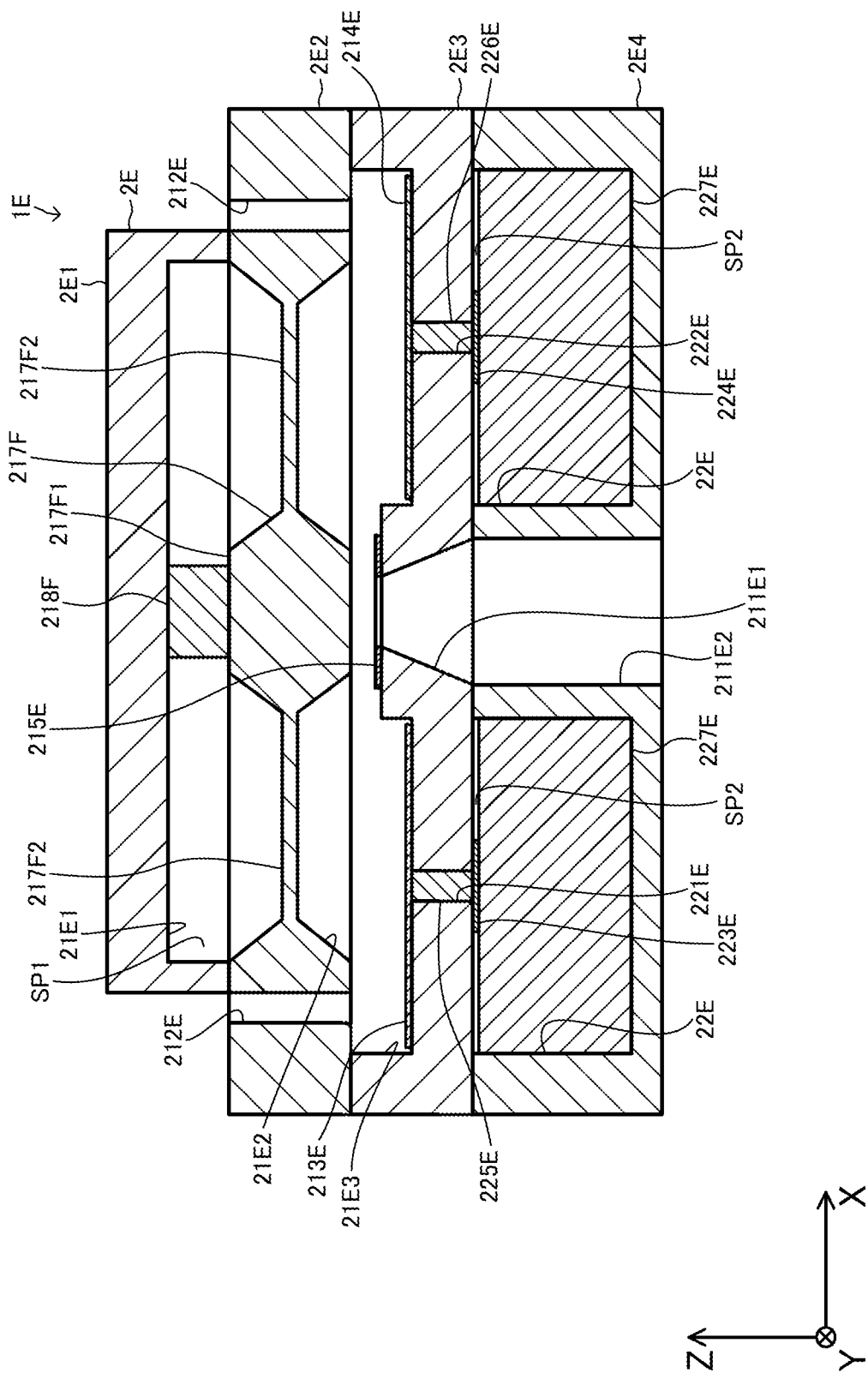
FIG. 20 is a cross-sectional view of an electronic device of a sixth embodiment.
Figure 21:
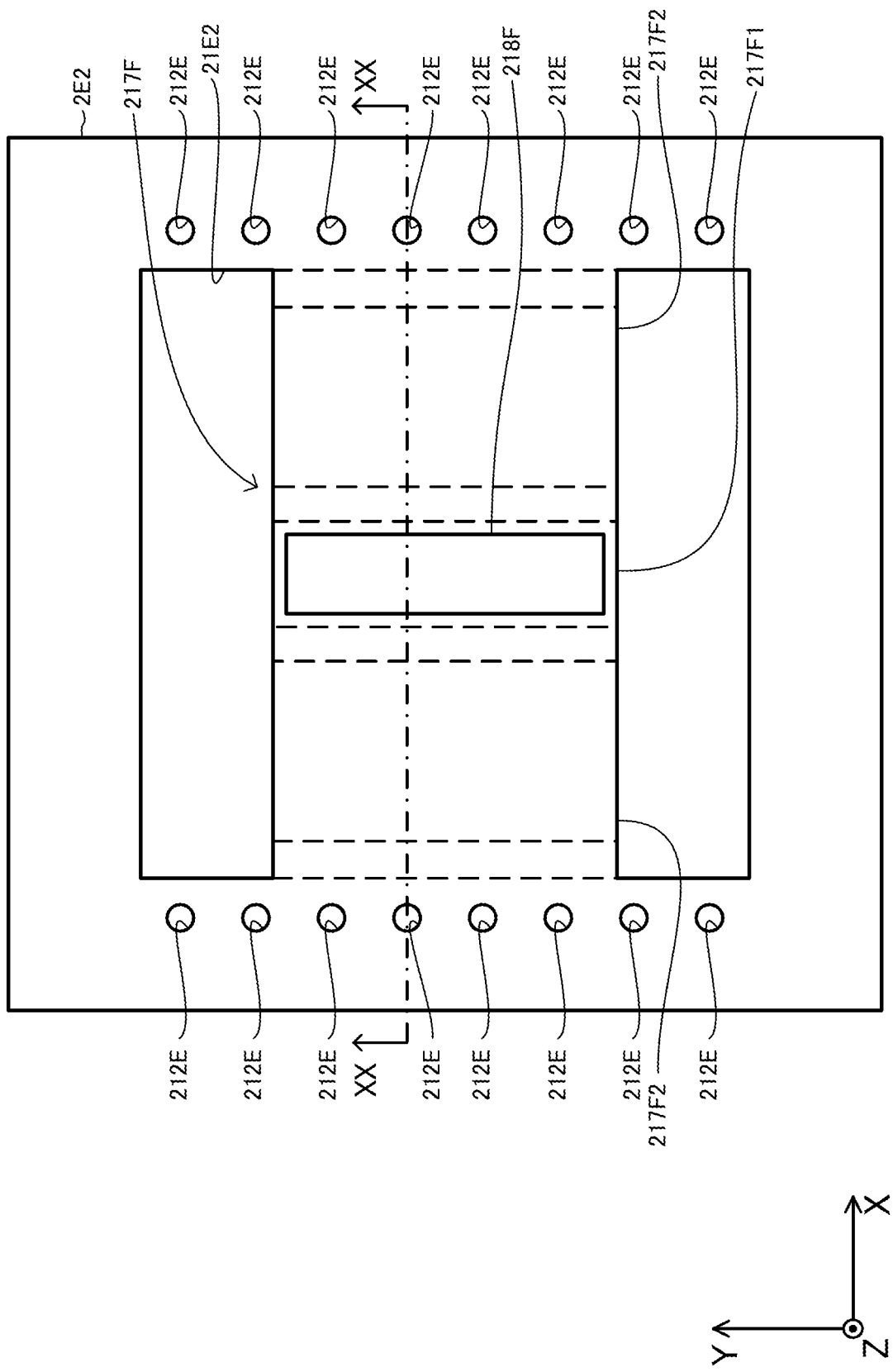
FIG. 21 is a top view of a second structure of the sixth embodiment.
Figure 22:
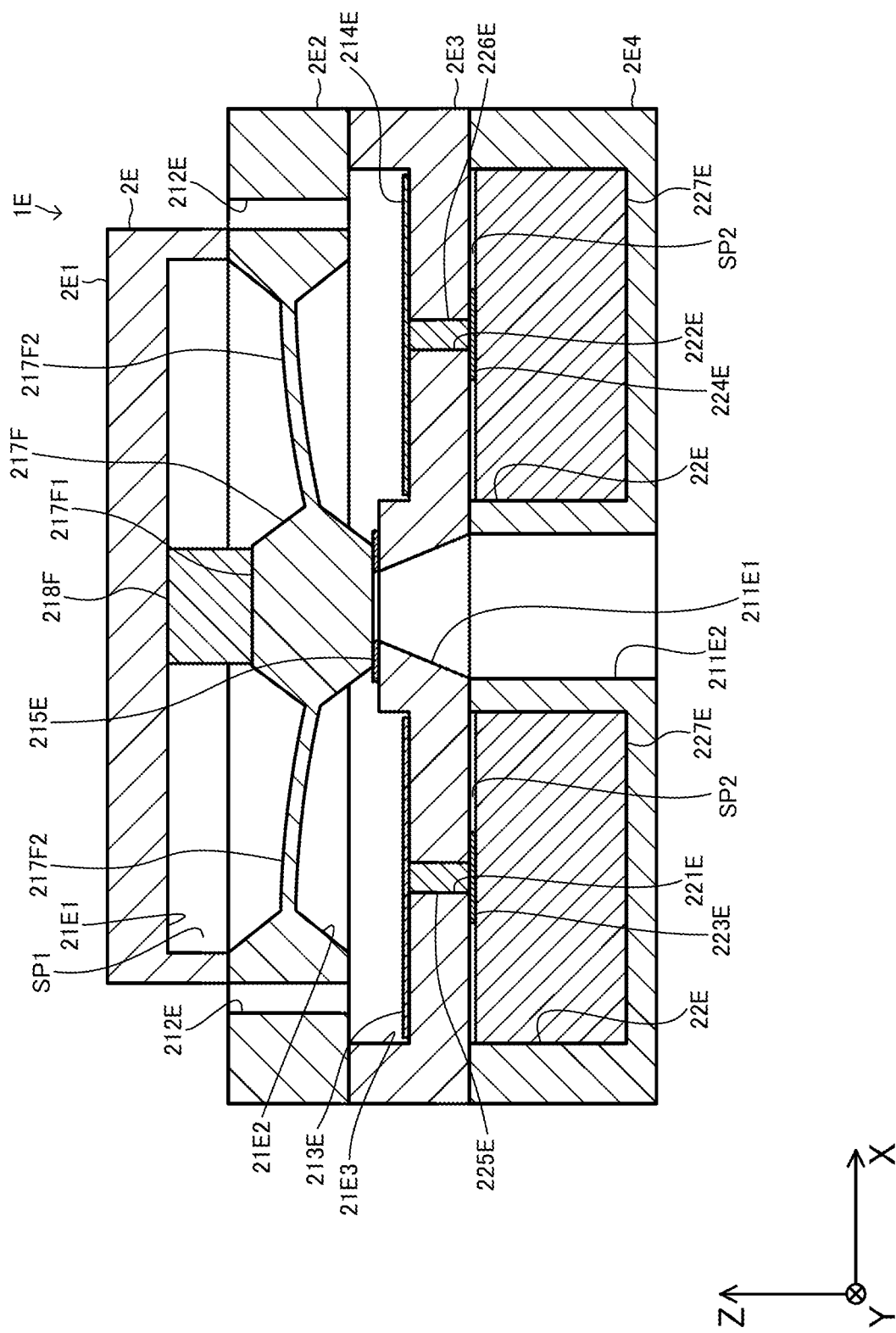
FIG. 22 is a cross-sectional view of the electronic device of the sixth embodiment, once volume changing bodies have expanded.

Referring to FIGS. 20-22, the electronic device 1E of the sixth embodiment includes a valve member 217F and a volume changing body 218F, in place of the multiple supports 216E and the valve member 217E of the fifth embodiment.

FIG. 20 is a cross-sectional view of the electronic device 1E on the plane passing Line XX-XX in FIG. 21. FIG. 21 is a diagram of the second structure 2E2 when viewed toward negative direction of the Z axis. FIG. 22 is a cross-sectional view of the electronic device 1E on the plane passing Line XX-XX in FIG. 21, once the volume changing body 218F has expanded.

In this example, the valve seat 215E is on the negative direction side of the Z axis, relative to the end face of the third structure 2E3 on the positive direction side of the Z axis (in other words, the end face of the second structure 2E2 on the negative direction side of the Z axis). Accordingly, in this example, the end face of the hole defined by the first channel defining part 211E1 on the positive direction side of the Z axis is also on the negative direction side of the Z axis, relative to the end face of the third structure 2E3 on the positive direction side of the Z axis.

As illustrated in FIG. 21, the valve member 217F extends from the end face of the through-hole part 21E2 on the negative direction side of the X axis, to the end face of the through-hole part 21E2 on the positive direction side of the X axis. The length of the valve member 217F in the Y-axis direction is smaller than the length in the Y-axis direction of the end face of the through-hole part 21E2 in the X-axis direction, and is longer than the length in the Y-axis direction of the end face of the hole defined by the first channel defining part 211E1 on the positive direction side of the Z axis.

As illustrated in FIGS. 20 and 21, the valve member 217F includes a base 217F1 and multiple (two in this example) arms 217F2.

The base 217F1 constitutes the center part in the X-axis direction of the valve member 217F. The length of the base 217F1 in the Z-axis direction (in other words, the thickness of the base 217F1) is equal to the length of the second structure 2E2 in the Z-axis direction (in other words, the thickness of the second structure 2E2). The length of the base 217F1 in the X-axis direction is slightly longer than the length in the X-axis direction of the end face of the hole defined by the first channel defining part 211E1 on the positive direction side of the Z axis.

In other words, when the second structure 2E2 is viewed toward the negative direction of the Z axis, the base 217F1 of the valve member 217F covers the end face of the hole defined by the first channel defining part 211E1 on the positive direction side of the Z axis, and also covers at least a part of the valve seat 215E.

The two arms 217F2 constitute both of the end parts of the valve member 217F in the X-axis direction (in other words, the parts of the valve member 217F other than the base 217F1), respectively. In other words, the two arms 217F2 support the base 217F1.

As illustrated in FIG. 20, the length of each arm 217F2 in the Z-axis direction (in other words, the thickness of the arm 217F2) is smaller than the thickness of the second structure 2E2. The position of each arm 217F2 in the Z-axis direction is at the center part in the Z-axis direction of the second structure 2E2.

Each arm 217F2 is in a planer shape that is parallel to the XY plane in a state that the volume changing body 218F does not expand.

The volume changing body 218F is made from material undergoes a volume change responsive to pH. In this example, the volume changing body 218F is made from material which undergoes a volume increase (in other words, expands) upon contacting a fluid with a pH lower than a predetermined threshold (e.g., pH of 5). The volume changing body 218F may be made from material that expands upon contacting a fluid with a pH higher than a predetermined threshold (e.g., pH of 4). In this example, the volume changing body 218F is made from pH-sensitive gel. In this example, expansion may also be referred to as swelling or inflation.

The pH-sensitive gel contains, as the main component, at least one of: anion gel having acidic functional group, such as carboxyl group, in macromolecule chain; cation gel having basic functional group in macromolecule chain; and amphoteric gel having both acidic functional group and basic functional group in macromolecule chain, for example. The pH-sensitive gel is an acrylamide-acrylic acid copolymer, for example.

The volume changing body 218F is in a pillar shape extending along the Z axis. In this example, the bottom of the volume changing body 218F is in a rectangular shape. The bottom of the volume changing body 218F may be in any shape other than the rectangular shape (e.g., circular, oval, square, polygonal, or other shape).

In this example, the length of the volume changing body 218F in the Z-axis direction (in other words, the height of the volume changing body 218F) is equal to the distance between the end face of the recess 21E1 on the positive direction side of the Z axis and the end face of the second structure 2E2 on the positive direction side of the Z axis (in other words, a first distance).

In this example, the length of the volume changing body 218F in the Z-axis direction after the volume changing body 218F has expanded completely is equal to or greater than the sum of the first distance and a second distance. The second distance is the distance between the end face of the second structure 2E2 on the negative direction side of the Z axis and the end face of the valve seat 215E on the positive direction side of the Z axis.

The end face of the volume changing body 218F on the negative direction side of the Z axis is secured to the end face of the surfaces of the base 217F1 on the positive direction side of the Z axis. The end face of the volume changing body 218F on the positive direction side of the Z axis is secured to the end face of the recess 21E1 on the positive direction side of the Z axis.

As illustrated in FIG. 21, the volume changing body 218F is located inside the outer edge of the base 217F1 on the XY plane.

In the manner as described above, the valve member 217F is supported by the main body 2E with contacting the volume changing body 218F.

As illustrated in FIG. 22, when the volume changing body 218F expands, the volume changing body 218F presses the base 217F1 toward the negative direction of the Z axis, thereby causing the base 217F1 of the valve member 217F to contact the valve seat 215E. In this example, the base 217F1 of the valve member 217F is pressed against the valve seat 215E. As a result, the valve member 217F closes the channel communicating between the first space SP1 and the outside of the main body 2E.

In this example, the volume changing body 218F is configured such that the volume changing body 218F expands completely once a fluid has been introduced to the first space SP1 through the hole defined by the first channel defining part 211E1 and through the hole defined by the second channel defining part 211E2, when the pH external to the first space SP1 is lower than the above-described threshold.

In this example, the valve seat 215E, the valve member 217F and the volume changing body 218F correspond to a valve that closes the channel communicating between the first space SP1 and the outside of the main body 2E, responsive to pH.

The volume changing body 218F may have a position and a size different from the position and the size illustrated in FIG. 21. The number of the volume changing body 218F may be two or greater.

In the electronic device 1E of the sixth embodiment, the volume changing body 218F expands completely once the gastric fluid has been introduced to the first space SP1.

Accordingly, the volume changing body 218F presses the base 217F1 toward the negative direction of the Z axis, thereby causing the base 217F1 of the valve member 217F to press the valve seat 215E. As a result, the valve member 217F closes the channel communicating between the first space SP1 and the outside of the main body 2E.

This can prevent any matter other than the gastric fluid (e.g., fluid with pH different from that of gastric fluid, solid matter, or the like) from entering the first space SP1. As a result, a decline in the power output can be suppressed.

As set forth above, the electronic device 1E of the sixth embodiment operates similarly to the electronic device 1E of the fifth embodiment, except for the difference in the valve mechanisms. Accordingly, effects and advantages similar to those of the electronic device 1E of the fifth embodiment are also achieved by the electronic device 1E of the sixth embodiment.

Furthermore, in the electronic device 1E of the sixth embodiment, the valve includes the valve seat 215E, the volume changing body 218F that undergoes a volume change responsive to pH, and the valve member 217F that is supported by the main body 2E with contacting the volume changing body 218F, and closes the channel by contacting the valve seat 215E upon a change in the volume of the volume changing body 218F.

In accordance with the above configuration, the volume changing body 218F undergoes a volume change in response to the change in pH. This causes the valve member 217F to contact the valve seat 215E. As a result, the channel communicating between the first space SP1 and the outside of the main body 2E is closed.

At least a part of the main body 2E may be made from any of optically transmissive materials such that the volume changing body 218F is irradiated with light through at least that part of the main body 2E. The first structure 2E1 may be made from optically transmissive material, for example. The optically transmissive material is glass, for example. In this case, a member made from glass and a member made from silicon (Si) may be bonded with anodic bonding.

In accordance with the above configuration, the volume changing body 218F can be formed by irradiating with light through the part of the main body 2E, which is made from the optically transmissive material. This facilitates manufacturing of the electronic device 1E having the volume changing body 218F disposed therein.

Seventh Embodiment

Next, an electronic device of a seventh embodiment will be described. The electronic device of the seventh embodiment is different from the electronic device of the fifth embodiment in that volume changing bodies that undergo volume changes responsive to pH are used, in place of the supports that are to be dissolved responsive to pH. Descriptions will be given focusing on that difference. In the descriptions of the seventh embodiment, elements denoted by like reference symbols denote the same or substantially similar elements used in the fifth embodiment.

Figure 23:
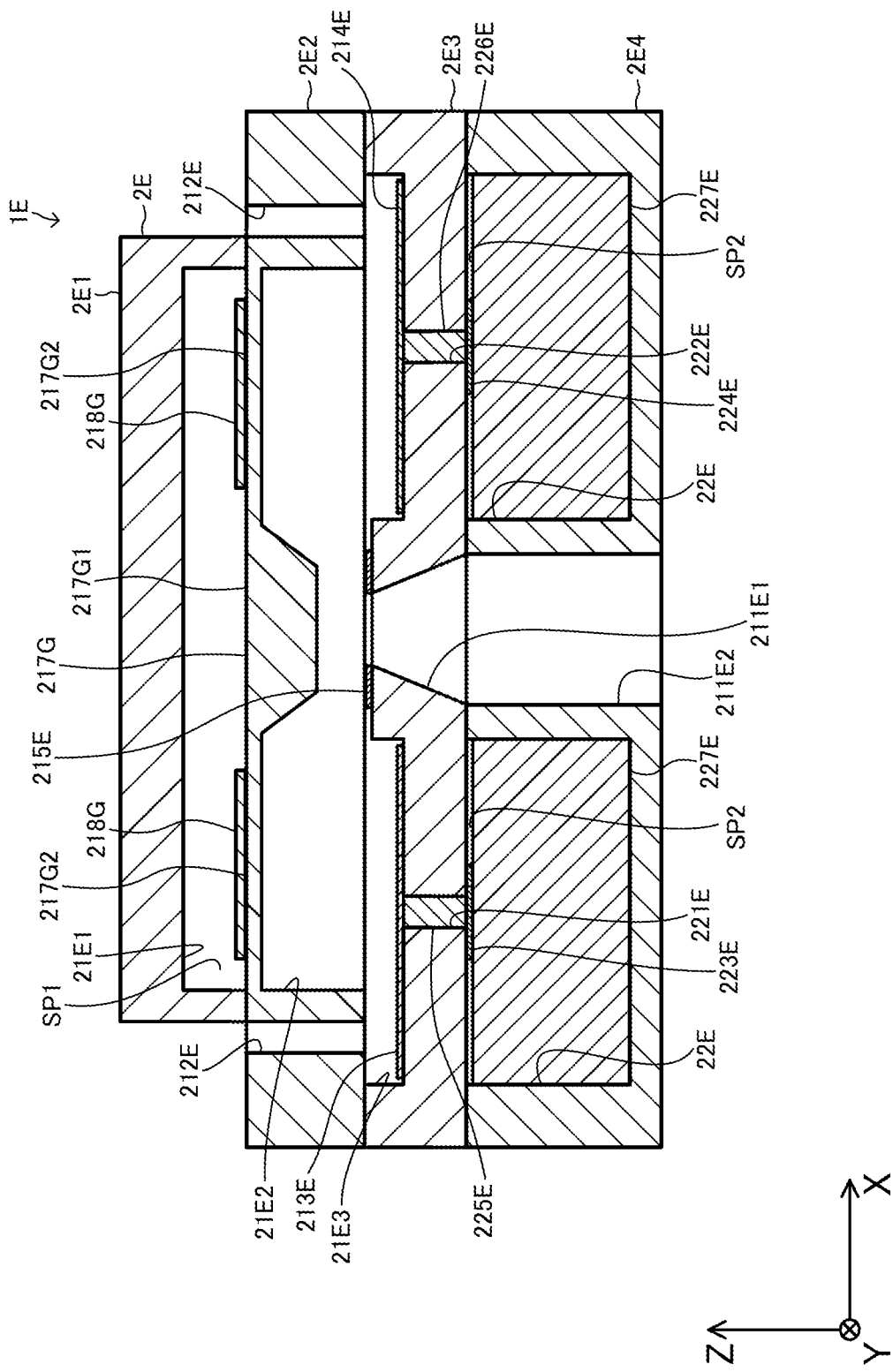
FIG. 23 is a cross-sectional view of an electronic device of a seventh embodiment.
Figure 24:
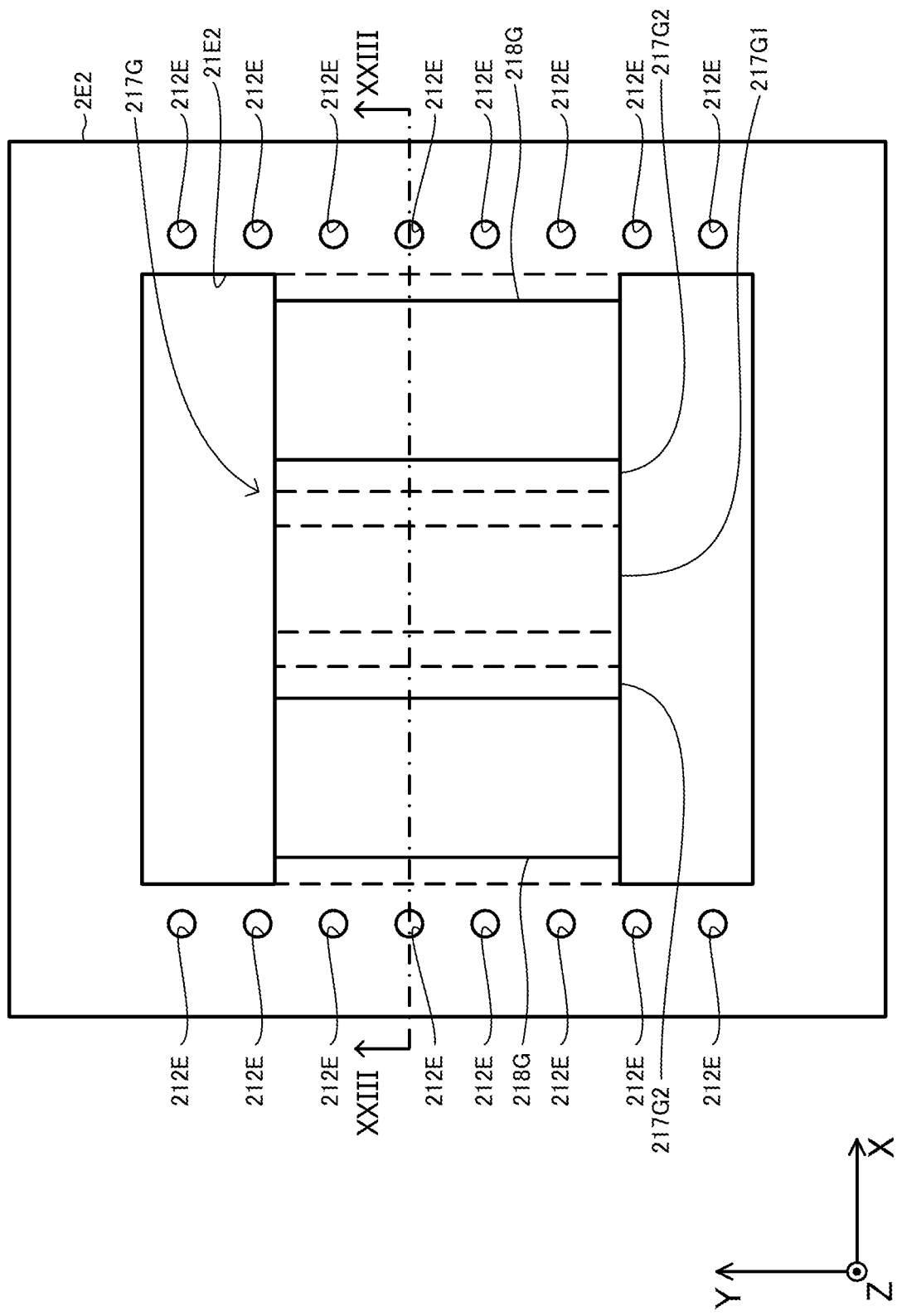
FIG. 24 is a top view of a second structure of the seventh embodiment.
Figure 25:
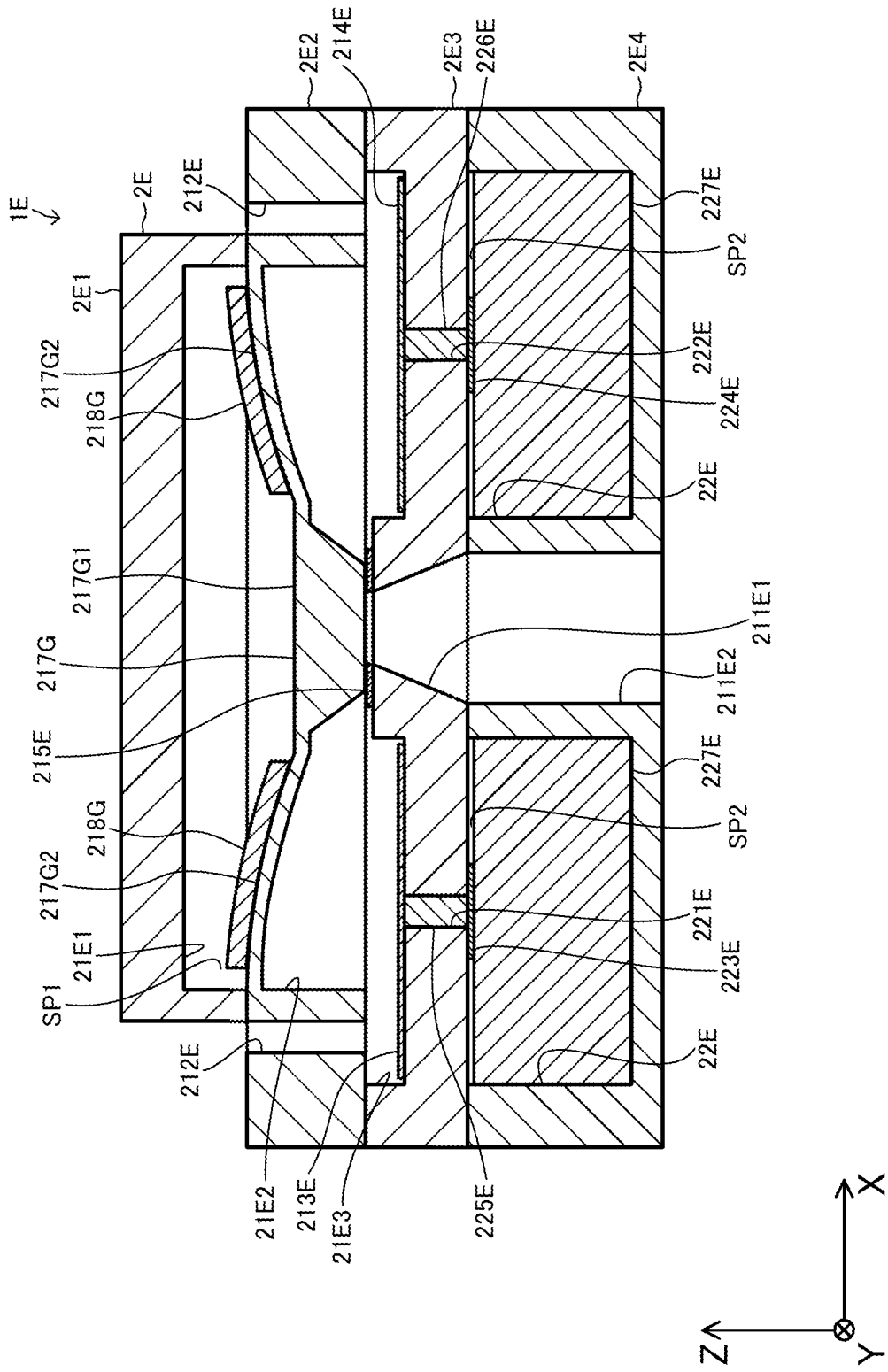
FIG. 25 is a cross-sectional view of the electronic device of the seventh embodiment, once volume changing bodies have expanded.

Referring to FIGS. 23-25, the electronic device 1E of the seventh embodiment includes a valve member 217G and multiple (two in this example) volume changing bodies 218G, in place of the multiple supports 216E and the valve member 217E of the fifth embodiment.

FIG. 23 is a cross-sectional view of the electronic device 1E on the plane passing Line XXIII-XXIII in FIG. 24. FIG. 24 is a diagram of the second structure 2E2 when viewed toward the negative direction of the Z axis. FIG. 25 is a cross-sectional view of the electronic device 1E once the volume changing bodies 218G have expanded, on the plane passing Line XXIII-XXIII in FIG. 24.

As illustrated in FIG. 24, the valve member 217G extends, from the end face of the through-hole part 21E2 on the negative direction side of the X axis, to the end face of the through-hole part 21E2 on the positive direction side of the X axis. The length in the Y-axis direction of the valve member 217G is smaller than the length in the Y-axis direction of the end face of the through-hole part 21E2 in the X-axis direction, and is longer than the length in the Y-axis direction of the end face of the hole defined by the first channel defining part 211E1 on the positive direction side of the Z axis.

As illustrated in FIGS. 23 and 24, the valve member 217G includes a base 217G1 and multiple (two in this example) arms 217G2.

The base 217G1 constitutes the center part in the X-axis direction of the valve member 217G. The length of the base 217G1 in the Z-axis direction (in other words, the thickness of the base 217G1) is smaller than the length of the second structure 2E2 in the Z-axis direction (in other words, the thickness of the second structure 2E2). In this example, the thickness of the base 217G1 is substantially the half of the thickness of the second structure 2E2.

The length of the base 217G1 in the X-axis direction is slightly longer than the length in the X-axis direction of the end face of the hole defined by the first channel defining part 211E1 on the positive direction side of the Z axis.

In other words, when the second structure 2E2 is viewed toward the negative direction of the Z axis, the base 217G1 of the valve member 217G covers the end face of the hole defined by the first channel defining part 211E1 on the positive direction side of the Z axis, and also covers at least a part of the valve seat 215E.

The base 217G1 constitutes a part of the end face of the second structure 2E2 on the positive direction side of the Z axis.

The two arms 217G2 constitute both of the end parts of the valve member 217G in the X-axis direction (in other words, the parts of the valve member 217G other than the base 217G1), respectively. In other words, the two arms 217G2 support the base 217G1.

As illustrated in FIG. 23, the length in the Z-axis direction of each arm 217G2 (in other words, the thickness of the arm 217G2) is smaller than the length of the base 217G1 in the Z-axis direction (in other words, the thickness of the base 217G1). Each arm 217G2 constitutes a part of the end face of the second structure 2E2 on the positive direction side of the Z axis.

Each arm 217G2 is in a planer shape that is parallel to the XY plane in a state that the volume changing bodies 218G do not expand. Accordingly, the end face of the base 217G1 on the negative direction side of the Z axis is away from the valve seat 215E, in a state that the volume changing bodies 218G do not expand.

Each volume changing body 218G is made from material undergoes a volume change responsive to pH. In this example, each volume changing body 218G is made from material which undergoes a volume increase (in other words, expands) upon contacting a fluid with a pH lower than a predetermined threshold (e.g., pH of 5). Each volume changing body 218G may be made from material that expands upon contacting a fluid with a pH higher than a predetermined threshold (e.g., pH of 4). In this example, each volume changing body 218G is made from pH-sensitive gel. In this example, expansion may also be referred to as swelling or inflation.

The pH-sensitive gel contains, as the main component, at least one of: anion gel having acidic functional group, such as carboxyl group, in macromolecule chain; cation gel having basic functional group in macromolecule chain; and amphoteric gel having both acidic functional group and basic functional group in macromolecule chain, for example. The pH-sensitive gel is an acrylamide-acrylic acid copolymer, for example.

As illustrated in FIGS. 23 and 24, each volume changing body 218G is in a planer shape that is parallel to the XY plane. Each volume changing body 218G is secured to the valve member 217G such that the entire end face of the surfaces of that volume changing body 218G on the negative direction side of the Z axis contacts the end face of the surfaces of the valve member 217G on the positive direction side of the Z axis. In this example, the two volume changing bodies 218G are secured to the respective two arms 217G2.

In the X-axis direction, each volume changing body 218G extends from the vicinity of the edge of the arm 217G2 on the negative direction side of the X axis, to the vicinity of the edge of the arm 217G2 on the positive direction side of the X axis. In the Y-axis direction, each volume changing body 218G extends from the edge of the valve member 217G on the negative direction side of the Y axis, to the edge of the valve member 217G on the positive direction side of the Y axis.

In the manner as described above, the valve member 217G is supported by the main body 2E with contacting the volume changing bodies 218G.

As illustrated in FIG. 25, volume changing bodies 218G stretch the respective arms 217G2 in the X-axis direction once the volume changing bodies 218G have expanded, and hence each arm 217G2 is curved such that a portion of the arm 217G2 is displaced further to the negative direction of the Z axis as the portion approaches, in the X-axis direction, the base 217G1. This causes the base 217G1 of the valve member 217G to contact the valve seat 215E. In this example, the base 217G1 of the valve member 217G is pressed against the valve seat 215E. As a result, the valve member 217G closes the channel communicating between the first space SP1 and the outside of the main body 2E.

In this example, the volume changing bodies 218G is configured such that the volume changing bodies 218G expand completely once a fluid has been introduced to the first space SP1 through the hole defined by the first channel defining part 211E1 and through the hole defined by the second channel defining part 211E2, when the pH external to the first space SP1 is lower than the above-described threshold.

In this example, the valve seat 215E, the valve member 217G, and the volume changing bodies 218G correspond to a valve that closes the channel communicating between the first space SP1 and the outside of the main body 2E, responsive to pH.

The volume changing bodies 218G may have positions and sizes different from the positions and the sizes illustrated in FIG. 24. The number of the volume changing bodies 218G may be two or greater.

In the electronic device 1E of the seventh embodiment, the volume changing bodies 218G expand completely once the gastric fluid has been introduced to the first space SP1. This causes the arms 217G2 to be curved. This causes the base 217G1 of the valve member 217G to be pressed against the valve seat 215E. As a result, the valve member 217G closes the channel communicating between the first space SP1 and the outside of the main body 2E.

This can prevent any matter other than the gastric fluid (e.g., fluid with pH different from that of gastric fluid, solid matter, or the like) from entering the first space SP1. As a result, a decline in the power output can be suppressed.

As set forth above, the electronic device 1E of the seventh embodiment operates similarly to the electronic device 1E of the fifth embodiment, except for the difference in the valve mechanisms. Accordingly, effects and advantages similar to those of the electronic device 1E of the fifth embodiment are also achieved by the electronic device 1E of the seventh embodiment.

Further, in the electronic device 1E of the seventh embodiment, the valve includes a valve seat 215E, volume changing bodies 218G that undergo volume changes responsive to pH, and a valve member 217G that is supported by the main body 2E with contacting the volume changing bodies 218G, and closes the channel by contacting the valve seat 215E upon a change in the volume of the volume changing bodies 218G.

In accordance with the above configuration, the volume changing bodies 218G undergo volume changes in response to the change in pH. This causes the valve member 217G to contact the valve seat 215E. As a result, the channel communicating between the first space SP1 and the outside of the main body 2E is closed.

At least a part of the main body 2E may be made from any of optically transmissive material such that the volume changing bodies 218G are irradiated with light through at least that part of the main body 2E. The first structure 2E1 may be made from optically transmissive material, for example. The optically transmissive material is glass, for example. In this case, a member made from glass and a member made from silicon (Si) may be bonded with anodic bonding.

In accordance with the above configuration, the volume changing bodies 218G can be formed by irradiating with light through the part of the main body 2E, which is made from the optically transmissive material. This facilitates manufacturing of the electronic device 1E having the volume changing bodies 218G disposed therein.

Eighth Embodiment

Next, an electronic device of an eighth embodiment will be described. The electronic device of the eighth embodiment is different from the electronic device of the first embodiment in terms of the valve. Descriptions will be given focusing on that difference. In the descriptions of the eighth embodiment, elements denoted by like reference symbols denote the same or substantially similar elements used in the first embodiment.

Figure 26:
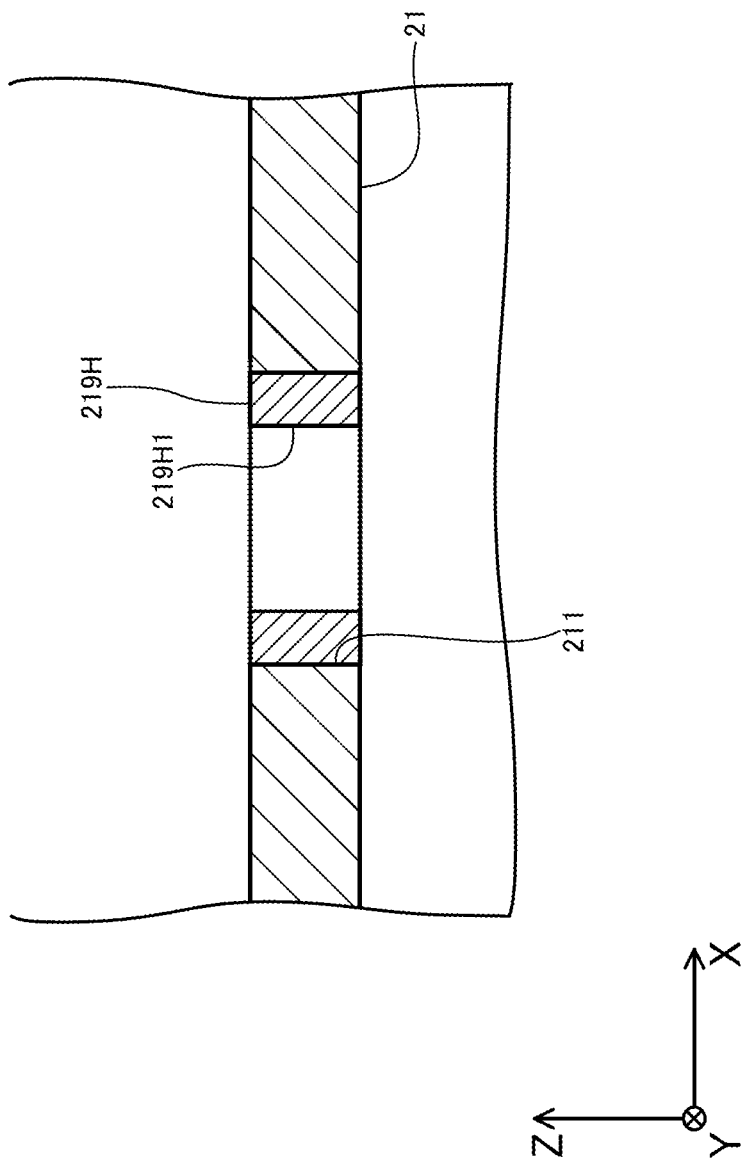
FIG. 26 is a partial cross-sectional view of an electronic device of an eighth embodiment, in an enlarged view of a volume changing body.
Figure 27:
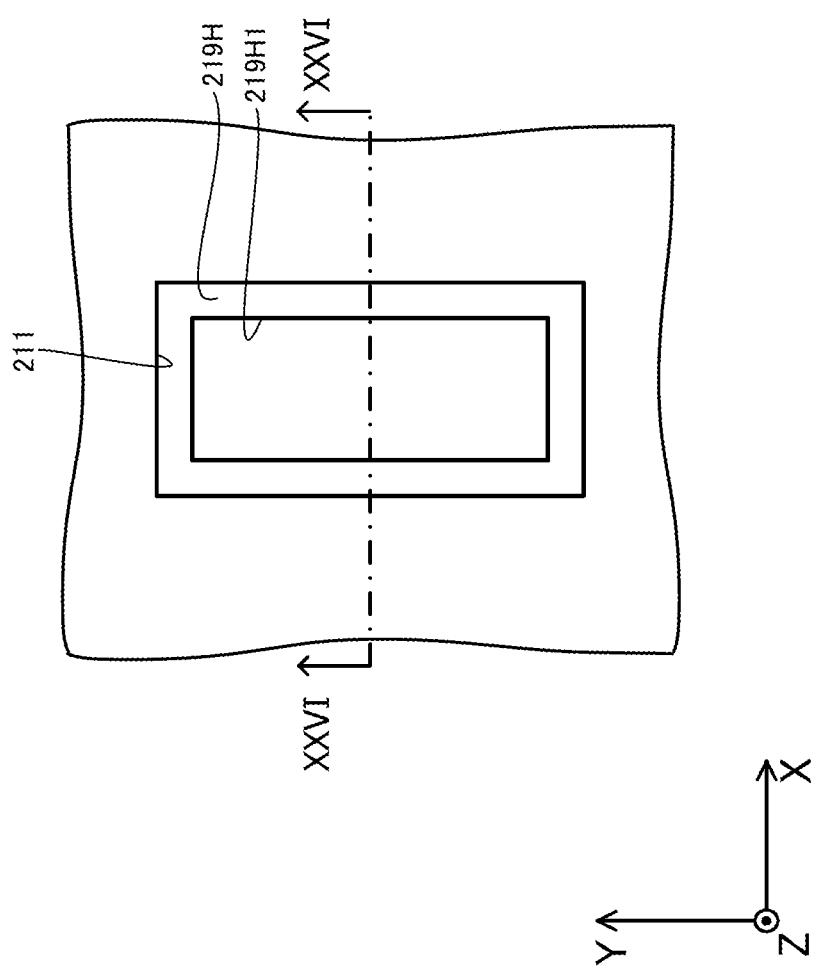
FIG. 27 is a partial top view of a main body of the eighth embodiment, in an enlarged view of the volume changing body.
Figure 28:
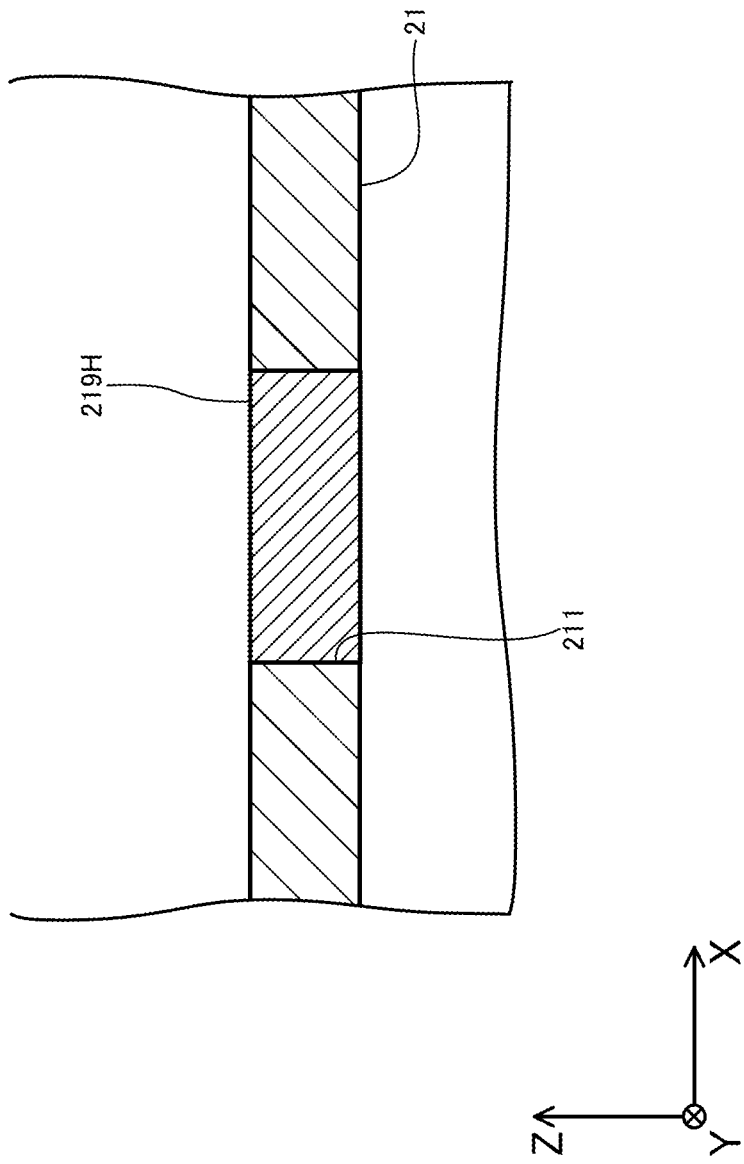
FIG. 28 is a partial cross-sectional view of the electronic device of the eighth embodiment once the volume changing bodies have expanded, in an enlarged view of the volume changing body.

Referring to FIGS. 26-28, the electronic device 1 of the eighth embodiment includes a volume changing body 219H, in place of the valve seat 215, the multiple supports 216 and the valve member 217 of the first embodiment.

FIG. 26 is a partial cross-sectional view of the electronic device 1 on the plane passing Line XXVI-XXVI in FIG. 27, in an enlarged view of the volume changing body 219H. FIG. 27 is an enlarged view of the area in the vicinity of the volume changing body 219H, when the main body 2 is viewed toward the negative direction of the Z axis. FIG. 28 is a partial cross-sectional view of the electronic device 1 on the plane passing Line XXVI-XXVI in FIG. 27, in an enlarged view of the volume changing body 219H when the volume changing body 219H expands.

The volume changing body 219H is made from material undergoes a volume change responsive to pH. In this example, the volume changing body 219H is made from material which undergoes a volume increase (in other words, expands) upon contacting a fluid with a pH lower than a predetermined threshold (e.g., pH of 5). The volume changing body 219H may be made from material that expands upon contacting a fluid with a pH higher than a predetermined threshold (e.g., pH of 4). In this example, the volume changing body 219H is made from pH-sensitive gel. In this example, expansion may also be referred to as swelling or inflation.

The pH-sensitive gel contains, as the main component, at least one of: anion gel having acidic functional group, such as carboxyl group, in macromolecule chain; cation gel having basic functional group in macromolecule chain; and amphoteric gel having both acidic functional group and basic functional group in macromolecule chain, for example. The pH-sensitive gel is an acrylamide-acrylic acid copolymer, for example.

The volume changing body 219H is in the same shape as that of the hole defined by the channel defining part 211. The volume changing body 219H contacts the channel defining part 211. In this example, the volume changing body 219H is secured to the channel defining part 211. As a result, in this example, the volume changing body 219H is disposed at the channel communicating between the first space SP1 and the outside of the main body 2.

The volume changing body 219H includes a through-hole part 219H1. The through-hole part 219H1 defines a hole that passes through the volume changing body 219H in the Z-axis direction, and is in a pillar shape extending along the Z axis. In other words, the hole defined by the through-hole part 219H1 communicates between the first space SP1 and the outside of the main body 2.

In this example, the bottom of the hole defined by the through-hole part 219H1 is in a rectangular shape. The bottom of the hole defined by the through-hole part 219H1 may be in any shape other than the rectangular shape (e.g., circular, oval, square, polygonal, or other shape).

The volume changing body 219H may be provided with multiple through-hole parts 219H1.

As illustrated in FIG. 28, once the volume changing body 218H has expanded, the hole defined by the through-hole part 219H1 is occluded. As a result, the volume changing body 219H closes the channel communicating between the first space SP1 and the outside of the main body 2.

In this example, the volume changing body 219H is configured such that the volume changing body 219H expands completely once a fluid has been introduced to the first space SP1 through the hole defined by the channel defining part 211, when the pH external to the first space SP1 is lower than the above-described threshold.

In this example, the volume changing body 219H corresponds to a valve that closes the channel communicating between the first space SP1 and the outside of the main body 2 responsive to pH.

In the electronic device 1 of the eighth embodiment, the volume changing body 219H expands completely once the gastric fluid has been introduced to the first space SP1. This causes the hole defined by the through-hole part 219H1 to be occluded. As a result, the volume changing body 219H closes the channel communicating between the first space SP1 and the outside of the main body 2.

This can prevent any matter other than the gastric fluid (e.g., fluid with pH different from that of gastric fluid, solid matter, or the like) from entering the first space SP1. As a result, a decline in the power output can be suppressed.

As set forth above, the electronic device 1 of the eighth embodiment operates similarly to the electronic device 1 of the first embodiment, except for the difference in the valve mechanisms. Accordingly, effects and advantages similar to those of the electronic device 1 of the first embodiment are also achieved by the electronic device 1 of the eighth embodiment.

Further, in the electronic device 1 of the eighth embodiment, the valve includes the volume changing body 219H that is disposed at the channel communicating between the first space SP1 and the outside of the main body 2, and closes the channel by undergoing a volume increase responsive to pH.

In accordance with the above configuration, the volume changing body 219H undergoes a volume change in response to a change in the pH in the channel. This causes the volume changing body 219H to occludes the channel. As a result, the channel communicating between the first space SP1 and the outside of the main body 2 is closed.

The volume changing body 219H may be made from material which undergoes a volume reduction (in other words, shrinks) upon contacting a fluid with a pH lower than a predetermined threshold (e.g., pH of 5). In this case, preferably, the volume changing body 219H occludes the channel when the volume changing body 219H does not shrink, and allows a communication between the first space SP1 and the outside of the main body 2 once the volume changing body 219H has shrunken.

At least a part of the main body 2 may be made from any of optically transmissive material such that the volume changing body 219H is irradiated with light through at least that part of the main body 2. The optically transmissive material is glass, for example. In this case, a member made from glass and a member made from silicon (Si) may be bonded with anodic bonding.

In accordance with the above configuration, the volume changing body 219H can be formed by irradiating with light through the part of the main body 2, which is made from the optically transmissive material. This facilitates manufacturing of the electronic device 1 having the volume changing body 219H disposed therein.

Ninth Embodiment

Next, an electronic device of a ninth embodiment will be described. The electronic device of the ninth embodiment is different from the electronic device of the first embodiment in terms of the main body and the valve. Descriptions will be given focusing on that difference. In the descriptions of the ninth embodiment, elements denoted by like reference symbols denote the same or substantially similar elements used in the first embodiment.

As illustrated in FIGS. 29-33, the electronic device 1J of the ninth embodiment includes a main body 2J, in place of the main body 2 of the first embodiment. In FIGS. 29-33, illustration of the film 3 is omitted.

Figure 29:
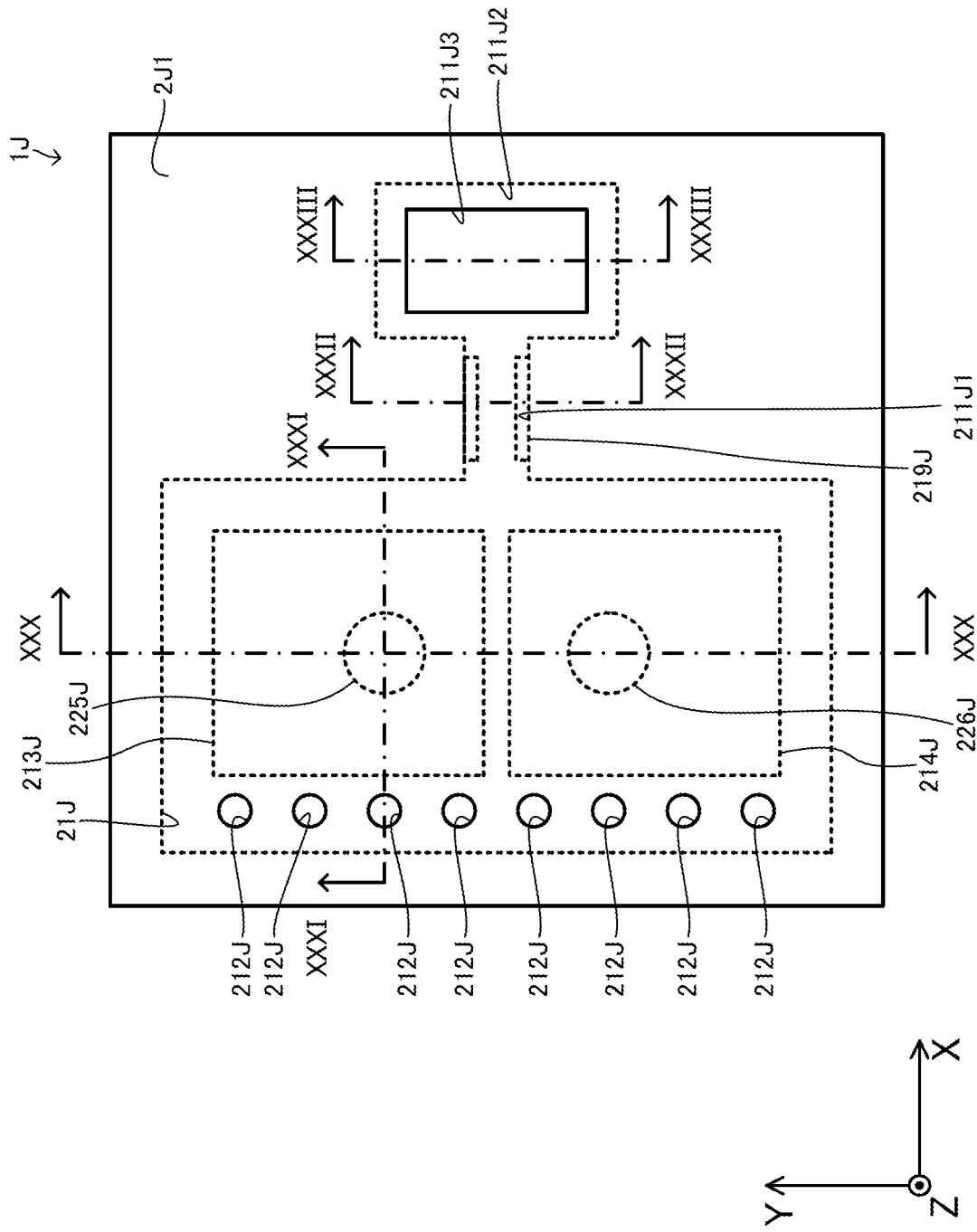
FIG. 29 is a top view of a main body of a ninth embodiment.
Figure 30:
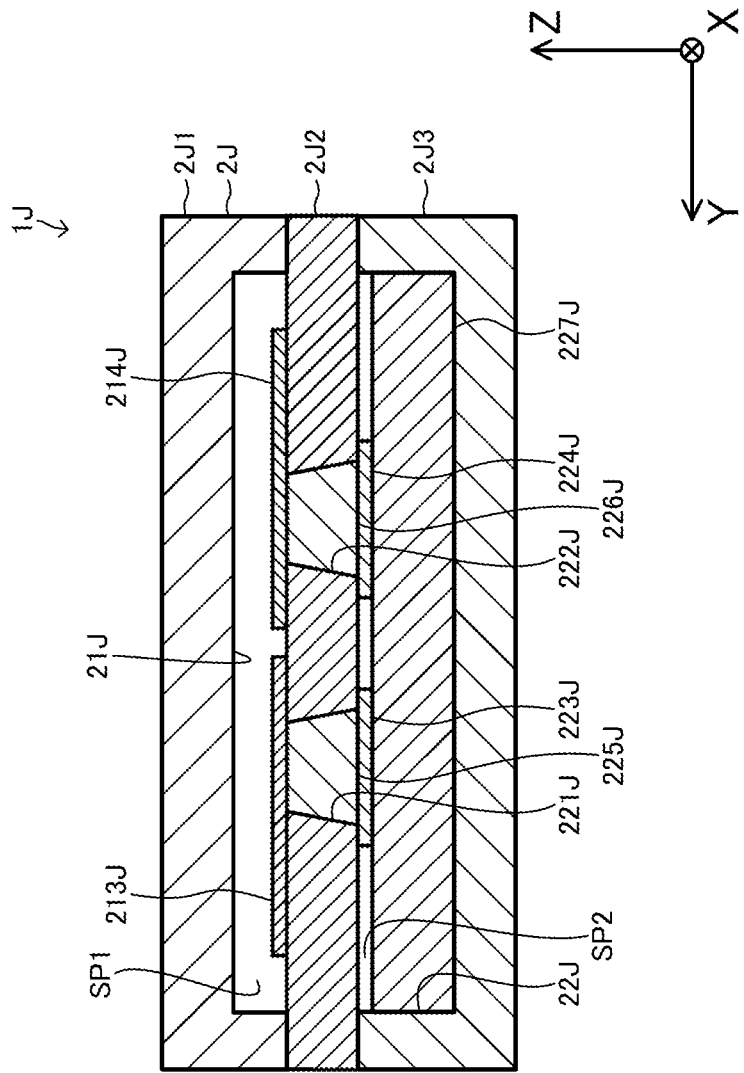
FIG. 30 is a cross-sectional view of an electronic device of the ninth embodiment.
Figure 31:
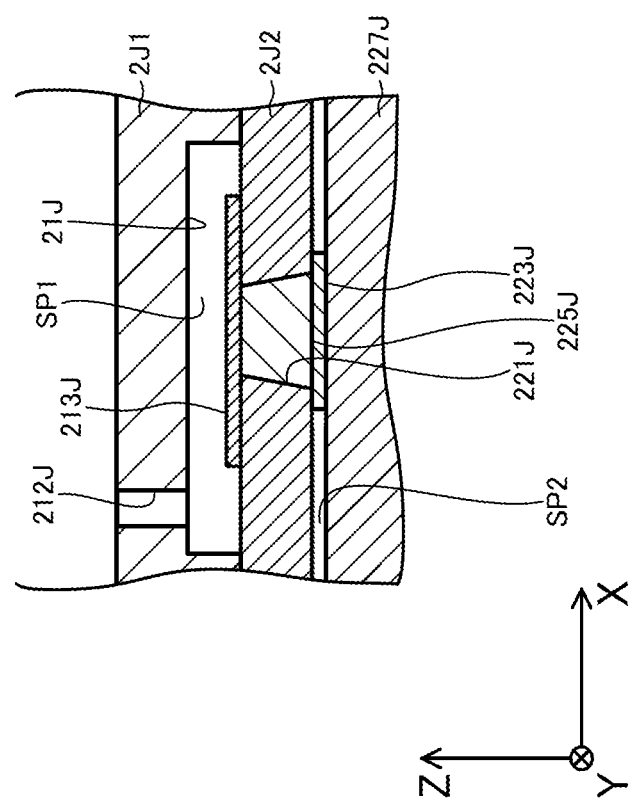
FIG. 31 is a partial cross-sectional view of the electronic device of the ninth embodiment, in an enlarged view of electrodes.
Figure 32:
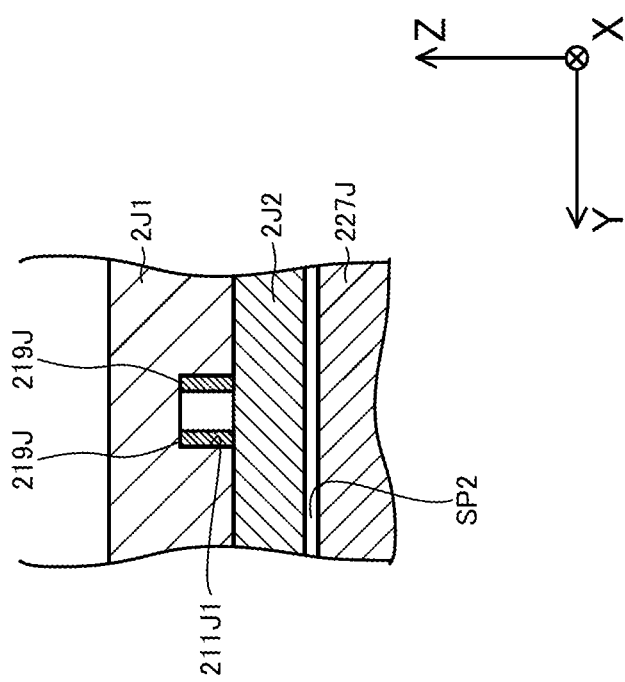
FIG. 32 is a partial cross-sectional view of the electronic device of the ninth embodiment, in an enlarged view of volume changing bodies.
Figure 33:
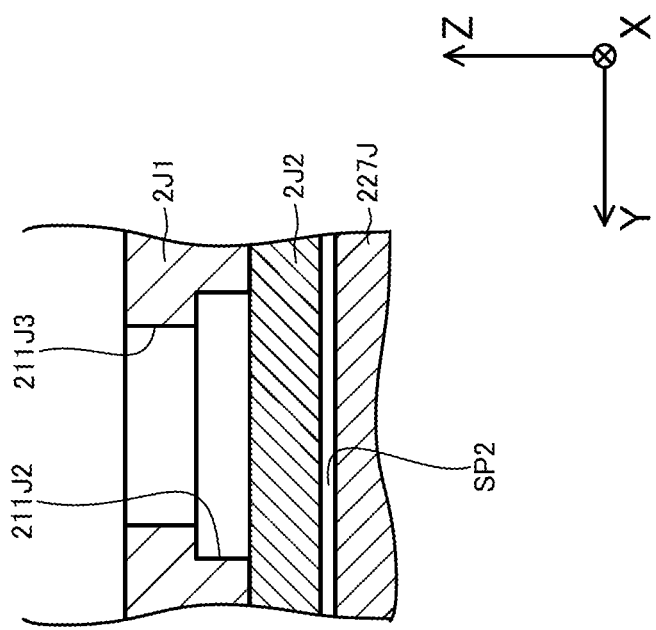
FIG. 33 is a partial cross-sectional view of the electronic device of the ninth embodiment, in an enlarged view of a through-hole.

FIG. 30 is a cross-sectional view of the electronic device 1J on the plane passing Line XXX-XXX in FIG. 29. FIG. 31 is a partial cross-sectional view of the electronic device 1J on the plane passing Line XXXI-XXXI in FIG. 29. FIG. 32 is a partial cross-sectional view of the electronic device 1J on the plane passing Line XXXII-XXXII in FIG. 29. FIG. 33 is a partial cross-sectional view of the electronic device 1J on the plane passing Line XXXIII-XXXIII in FIG. 29.

In this example, the main body 2J is made from silicon (Si). At least a part of the main body 2J may be made from glass. In this example, as illustrated in FIG. 30, the main body 2J includes a first structure 2J1, a second structure 2J2, and a third structure 2J3.

Each structures 2J1-2J3 is in a pillar shape extending along the Z axis. In this example, the bottom of each structures 2J1-2J3 is in a square shape. The bottom of each structures 2J1-2J3 may be in any shape other than the square shape (e.g., circular, oval, rectangular, polygonal, or any other shape).

The bottoms of the first structure 2J1, the second structure 2J2, and the third structure 2J3 are in the same shape. The central axes of the three structures 2J1-2J3 coincide with each other.

The first structure 2J1, the second structure 2J2, and the third structure 2J3 are stacked. The end face of the first structure 2J1 on the negative direction side of the Z axis contacts the end face of the second structure 2J2 on the positive direction side of the Z axis. The end face of the second structure 2J2 on the negative direction side of the Z axis contacts the end face of the third structure 2J3 on the positive direction side of the Z axis.

The first structure 2J1 includes a first recess 21J, a second recess 211J1, a third recess 211J2, and a through-hole part 211J3.

The first recess 21J, the second recess 211J1, and the third recess 211J2 defines respective spaces adjoining the second structure 2J2, on the end face of the first structure 2J1 on the negative direction side of the Z axis. In other words, the first recess 21J, the second recess 211J1, and the third recess 211J2 open at the end face of the first structure 2J1 on the negative direction side of the Z axis.

The respective spaces defined by the first recess 21J, the second recess 211J1, and the third recess 211J2 adjoin the end face of the second structure 2J2 on the positive direction side of the Z axis.

The space defined by the first recess 21J is in a pillar shape extending along the Z axis. In this example, the bottom of the space defined by the first recess 21J is in a rectangular shape of which the long sides and the short sides extend along the Y axis and the X axis, respectively. The bottom of the space defined by the first recess 21J may be in any shape other than the rectangular shape (e.g., circular, oval, square, polygonal, or other shape).

In this example, the space defined by the first recess 21J extends from the end part of the first structure 2J1 on the negative direction side of the X axis, to the center part in the X-axis direction of the first structure 2J1, in the X-axis direction. In this example, the space defined by the first recess 21J extends from the end part of the first structure 2J1 on the negative direction side of the Y axis, to the end part of the first structure 2J1 on the positive direction side of the Y axis, in the Y-axis direction.

The space defined by the second recess 211J1 is in a pillar shape extending along the Z axis. In this example, the bottom of the space defined by the second recess 211J1 is in a rectangular shape of which the long sides and the short sides extend along the X axis and the Y axis, respectively. The bottom of the space defined by the second recess 211J1 may be in any shape other than the rectangular shape (e.g., circular, oval, square, polygonal, or other shape).

The short sides of the bottom of the space defined by the second recess 211J1 are shorter than the long sides of the bottom of the space defined by the first recess 21J. In this example, the second recess 211J1 is located at center part of the first structure 2J1 in the Y-axis direction.

The end of the second recess 211J1 on the negative direction side of the X axis is connected to the end face of the first recess 21J on the positive direction side of the X axis. In other words, the space defined by the second recess 211J1 continuously communicates with the space defined by the first recess 21J.

The space defined by the third recess 211J2 is in a pillar shape extending along the Z axis. In this example, the bottom of the space defined by the third recess 211J2 is in a rectangular shape of which the long sides and the short sides extend along the Y axis and the X axis, respectively. The bottom of the space defined by the third recess 211J2 may be in any shape other than the rectangular shape (e.g., circular, oval, square, polygonal, or other shape).

The long sides of the bottom of the space defined by the third recess 211J2 are longer than the short sides of the bottom of the space defined by the second recess 211J1. In this example, the long sides of the bottom of the space defined by the third recess 211J2 are shorter than the long sides of the bottom of the space defined by the first recess 21J. In this example, the third recess 211J2 is located at a region which is the center part of the first structure 2J1 in the Y-axis direction, and is the end part of the first structure 2J1 on the positive direction side of the X axis.

The end of the second recess 211J1 on the positive direction side of the X axis is connected to the end face of the third recess 211J2 on the negative direction side of the X axis. In other words, the space defined by the second recess 211J1 continuously communicates with the space defined by the third recess 211J2.

As illustrated in FIGS. 29 and 33, the through-hole part 211J3 defines a hole that passes through the wall of the first structure 2J1 defining the end face of the third recess 211J2 on the positive direction side of the Z axis in the Z-axis direction, and is in a pillar shape extending along the Z axis.

In this example, the bottom of the hole defined by the through-hole part 211J3 is in a rectangular shape. The bottom of the hole defined by the through-hole part 211J3 may be in any shape other than the rectangular shape (e.g., circular, oval, square, polygonal, or other shape). The hole defined by the through-hole part 211J3 may be shaped to be a part of a cone.

In this example, the outer edge of the hole defined by the through-hole part 211J3 on the XY plane is located inside the outer edge of the space defined by the third recess 211J2 on the XY plane.

In this example, the space defined by the end face of the second structure 2J2 on the positive direction side of the Z axis and the first recess 21J constitutes the first space SP1 defined inside the main body 2J.

In this example, the spaces and the holes defined by the end face of the second structure 2J2 on the positive direction side of the Z axis, the second recess 211J1, the third recess 211J2, and the through-hole part 211J3 constitute the channel communicating between the first space SP1 and the outside of the main body 2J.

The third structure 2J3 includes a recess 22J. The recess 22J defines a space adjoining the second structure 2J2 on the end face of the third structure 2J3 on the positive direction side of the Z axis. In other words, the recess 22J opens at the end face of the third structure 2J3 on the positive direction side of the Z axis.

The space defined by the recess 22J adjoins the end face of the second structure 2J2 on the negative direction side of the Z axis. In this example, the space defined by the end face of the second structure 2J2 on the negative direction side of the Z axis and the recess 22J constitute the second space SP2 defined inside the main body 2J.

In this example, the first structure 2J1 constitutes a first layer. In this example, the third structure 2J3 constitutes a second layer different from the first layer.

The electronic device 1J may include a retaining member made from porous material in the first space SP1. In this case, the porous material is preferably hydrophilic.

In this example, the first recess 21J, the second recess 211J1, the third recess 211J2, and the through-hole part 211J3 are coated with hydrophilic films. The hydrophilic films are made from silicon dioxide, for example.

As illustrated in FIGS. 29 and 31, the first structure 2J1 includes multiple (eight in this example) through-hole parts 212J.

Each through-hole part 212J defines a hole that passes through the wall of the first structure 2J1 defining the end face of the first recess 21J on the positive direction side of the Z axis in the Z-axis direction, and is in a pillar shape extending along the Z axis.

In this example, the bottom of the hole defined by each through-hole part 212J is in a circular shape. The bottom of the hole defined by each through-hole part 212J may be in any shape other than the circular shape (e.g., oval, square, rectangular, polygonal, or other shape). The hole defined by each through-hole part 212J may be shaped to be a part of a cone.

In this example, the area of the bottom of the hole defined by each through-hole part 212J is smaller than the area of the bottom of the hole defined by the through-hole part 211J3. The bottom of the hole defined by each through-hole part 212J has a diameter between 2 μm and 200 μm, for example.

As illustrated in FIG. 29, the through-hole parts 212J are disposed along the end part of the first structure 2J1 on the negative direction side of the X axis. The multiple through-hole parts 212J are spaced apart at regular intervals along the Y axis.

In the manner as described above, the hole defined by each through-hole part 212J communicates between the first space SP1 and the outside of the main body 2J. The number of the through-hole parts 212J may be any number other than eight.

In this example, each through-hole part 212J is covered with a water-repellent film. The water-repellent film is made from fluorocarbon resin (e.g., resin containing polytetrafluoroethylene as the main component), for example.

Further, the electronic device 1J includes a first electrode 213J, a second electrode 214J, multiple (two in this example) volume changing bodies 219J, in place of the first electrode 213, the second electrode 214, the valve seat 215, the multiple supports 216, and the valve member 217 of the first embodiment.

In this example, the main body 2J, the film 3, the first electrode 213J, the second electrode 214J, and the volume changing bodies 219J of the electronic device 1J constitute a battery. In this example, the first electrode 213J and the second electrode 214J may also be referred to as the pair of electrodes.

In this example, the first electrode 213J is made from magnesium. The first electrode 213J may be made from any material other than magnesium (e.g., zinc, alloy, or the like). Alternatively, the first electrode 213J may be a film stack where multiple layers respectively made from different materials are stacked.

The first electrode 213J is in a planer shape that is parallel to the XY plane. The first electrode 213J has a thickness between 100 nm and 2 mm, for example. In this example, the first electrode 213J is in a square shape. The first electrode 213J may be in any shape other than the square shape (e.g., circular, oval, rectangular, polygonal, or any other shape).

The first electrode 213J contacts the end face of the second structure 2J2 on the positive direction side of the Z axis.

In this example, the area of the first electrode 213J is slightly smaller than the half of the area of the end face of the first recess 21J on the positive direction side of the Z axis.

In this example, the second electrode 214J is made from platinum. The second electrode 214J may be made from any material other than platinum (e.g., copper chloride (CuCl), silver chloride (AgCl), alloy, or the like). Alternatively, the second electrode 214J may be a film stack where multiple layers respectively made from different materials are stacked.

The second electrode 214J is in a planer shape that is parallel to the XY plane. The second electrode 214J has a thickness between 10 nm and 2 mm, for example. In this example, the second electrode 214J is in a square shape. The second electrode 214J may be in any shape other than the square shape (e.g., circular, oval, rectangular, polygonal, or any other shape).

The second electrode 214J contacts the end face of the second structure 2J2 on the positive direction side of the Z axis.

In this example, the area of the second electrode 214J is slightly smaller than the half of the area of the end face of the first recess 21J on the positive direction side of the Z axis.

In this example, the first electrode 213J is on the positive direction side of the Y axis relative to the center of the first structure 2J1 in the Y-axis direction. In this example, the second electrode 214J is on the negative direction side of the Y axis relative to the center of the first structure 2J1 in the Y-axis direction. In other words, the first electrode 213J and the second electrode 214J are separated from each other.

In this example, the materials of the first electrode 213J and the second electrode 214J are selected such that electric power is generated by a gastric fluid functioning as an electrolyte once a gastric fluid has been introduced to the first space SP1.

Each volume changing body 219J is made from material undergoes a volume change responsive to pH. In this example, each volume changing body 219J is made from material which undergoes a volume increase (in other words, expands) upon contacting a fluid with a pH lower than a predetermined threshold (e.g., pH of 5). Each volume changing body 219J may be made from material that expands upon contacting a fluid with a pH higher than a predetermined threshold (e.g., pH of 4). In this example, each volume changing body 219J is made from pH-sensitive gel. In this example, expansion may also be referred to as swelling or inflation.

The pH-sensitive gel contains, as the main component, at least one of: anion gel having acidic functional group, such as carboxyl group, in macromolecule chain; cation gel having basic functional group in macromolecule chain; and amphoteric gel having both acidic functional group and basic functional group in macromolecule chain, for example. The pH-sensitive gel is an acrylamide-acrylic acid copolymer, for example.

As illustrated in FIGS. 29 and 32, each volume changing body 219J is in a planer shape parallel to the ZX plane. In this example, each volume changing body 219J is in a rectangular shape. Each volume changing body 219J may be in any shape other than the rectangular shape (e.g., circular, oval, square, polygonal, or other shape).

In this example, the length of the short sides of each volume changing body 219J is equal to the length in the Z-axis direction of the end face of the second recess 211J1 in the Y-axis direction. In this example, the length of the long sides of each volume changing body 219J is slightly shorter than the length in the X-axis direction of the end face of the second recess 211J1 in the Y-axis direction. The thickness of each volume changing body 219J is shorter than the half of the distance between the end faces of the second recess 211J1 in the Y-axis direction.

The two volume changing bodies 219J contact both of the end faces of the second recess 211J1 in the Y-axis direction, respectively. In this example, the two volume changing bodies 219J are secured to both of the end faces of the second recess 211J1 in the Y-axis direction, respectively. Accordingly, in this example, the volume changing bodies 219J are disposed at the channel communicating between the first space SP1 and the outside of the main body 2J.

In the manner as described above, in this example, the two volume changing bodies 219J are separated from each other. In other words, the space between the two volume changing bodies 219J communicates between the first space SP1 and the outside of the main body 2J.

Once the volume changing bodies 219J have expanded, the two volume changing bodies 219J contact to each other and the space between the two volume changing bodies 219J is occluded. As a result, the two volume changing bodies 219J close the channel communicating between the first space SP1 and the outside of the main body 2J.

In this example, each volume changing body 219J is configured such that the volume changing body 219J expands completely once the fluid has been introduced to the first space SP1 through the channel defined by the second recess 211J1, the third recess 211J2, and the through-hole part 211J3, when the pH external to the first space SP1 is lower than the above-described threshold.

In this example, the volume changing bodies 219J correspond to a valve that closes the channel communicating between the first space SP1 and the outside of the main body 2J, responsive to pH.

The volume changing bodies 219J may have positions and sizes different from the positions and the sizes illustrated in FIG. 29. The number of the volume changing bodies 219J may be any number other than two.

Further, the electronic device 1J includes a first through-hole part 221J, a second through-hole part 222J, a first terminal 223J, a second terminal 224J, a first conductor 225J, a second conductor 226J, and a circuit 227J, which are configured similarly to the first through-hole part 221, the second through-hole part 222, the first terminal 223, the second terminal 224, the first conductor 225, the second conductor 226, and the circuit 227 of the first embodiment.

In the electronic device 1J of the ninth embodiment, the volume changing bodies 219J expand completely once the gastric fluid has been introduced to the first space SP1. This causes the space between the two volume changing bodies 219J to be occluded. As a result, the volume changing bodies 219J closes the channel communicating between the first space SP1 and the outside of the main body 2J.

This can prevent any matter other than the gastric fluid (e.g., fluid with pH different from that of gastric fluid, solid matter, or the like) from entering the first space SP1. As a result, a decline in the power output can be suppressed.

As set forth above, the electronic device 1J of the ninth embodiment operates similarly to the electronic device 1 of the first embodiment, except for the difference in the valve mechanisms. Accordingly, effects and advantages similar to those of the electronic device 1 of the first embodiment are also achieved by the electronic device 1J of the ninth embodiment.

Further, in the electronic device 1J of the ninth embodiment, the valve includes the volume changing bodies 219J that are disposed at the channel communicating between the first space SP1 and the outside of the main body 2J, and close the channel by undergoing volume increases responsive to pH.

In accordance with the above configuration, the volume changing bodies 219J undergo volume changes in response to a change in the pH in the channel. This causes the volume changing bodies 219J to occlude the channel. As a result, the channel communicating between the first space SP1 and the outside of the main body 2J is closed.

The volume changing bodies 219J may be made from material which undergoes a volume reduction (in other words, shrinks) upon contacting a fluid with a pH lower than a predetermined threshold (e.g., pH of 5). In this case, preferably, the volume changing bodies 219J occlude the channel when the volume changing bodies 219J do not shrink, and permit to communicate between the first space SP1 and the outside of the main body 2J once the volume changing bodies 219J have shrunken.

At least a part of the main body 2J may be made from any of optically transmissive material such that the volume changing bodies 219J are irradiated with light through the part of the main body 2J. The second structure 2J2 may be made from optically transmissive material, for example. The optically transmissive material is glass, for example. In this case, a member made from glass and a member made from silicon (Si) may be bonded with anodic bonding.

In accordance with the above configuration, the volume changing bodies 219J can be formed by irradiating with light through the part of the main body 2J, which is made from the optically transmissive material. This facilitates manufacturing of the electronic device 1J having the volume changing bodies 219J disposed therein.

First Modification to Ninth Embodiment

Next, an electronic device of a first modification to the ninth embodiment will be described. The electronic device of the first modification to the ninth embodiment is different from the electronic device of the ninth embodiment in terms of the main body and the number of valves. Descriptions will be given focusing on that difference. In the first modification to the ninth embodiment, elements denoted by like reference symbols denote the same or substantially similar elements used in the ninth embodiment.

Figure 34:
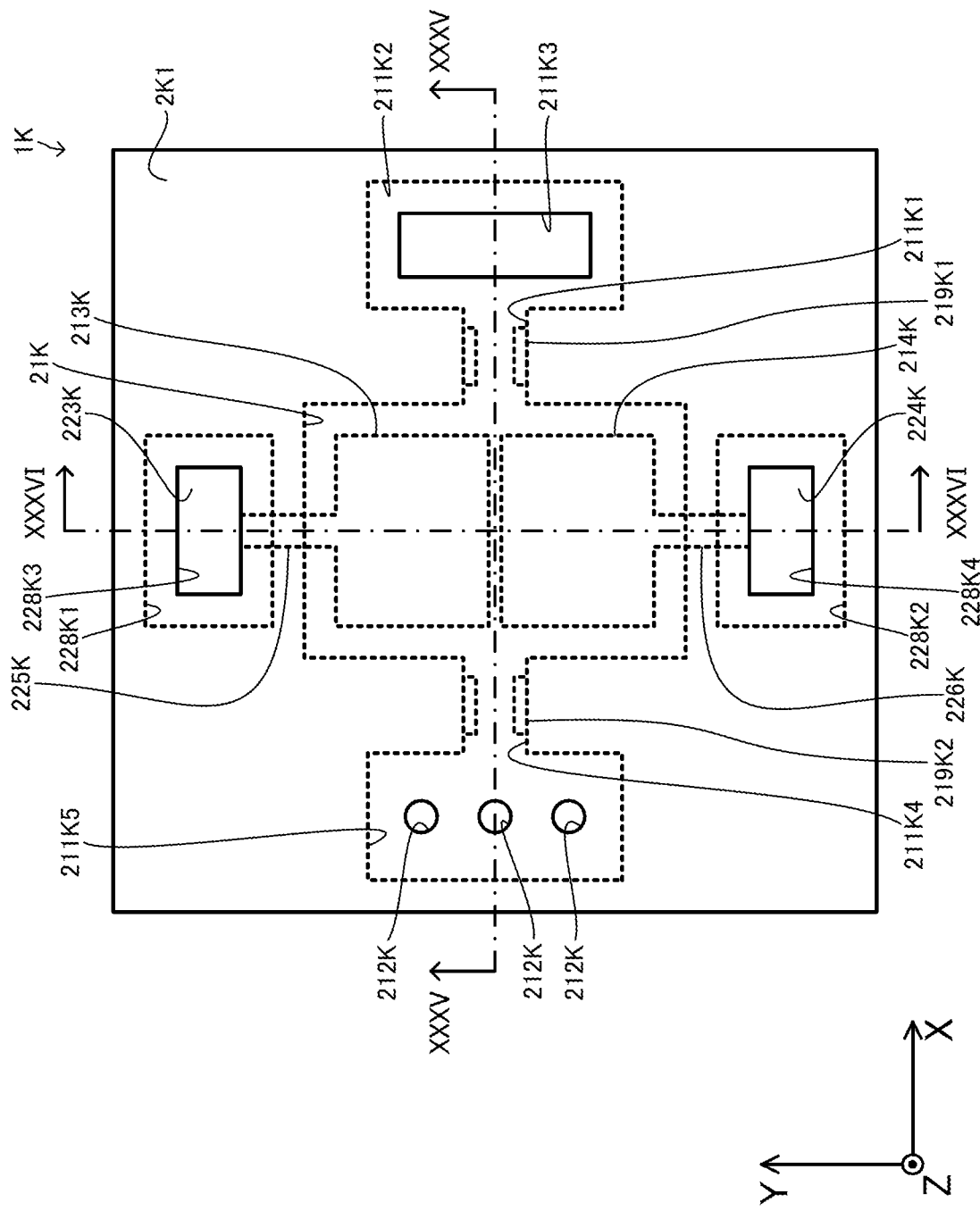
FIG. 34 is a top view of a main body of a first modification to the ninth embodiment.
Figure 35:
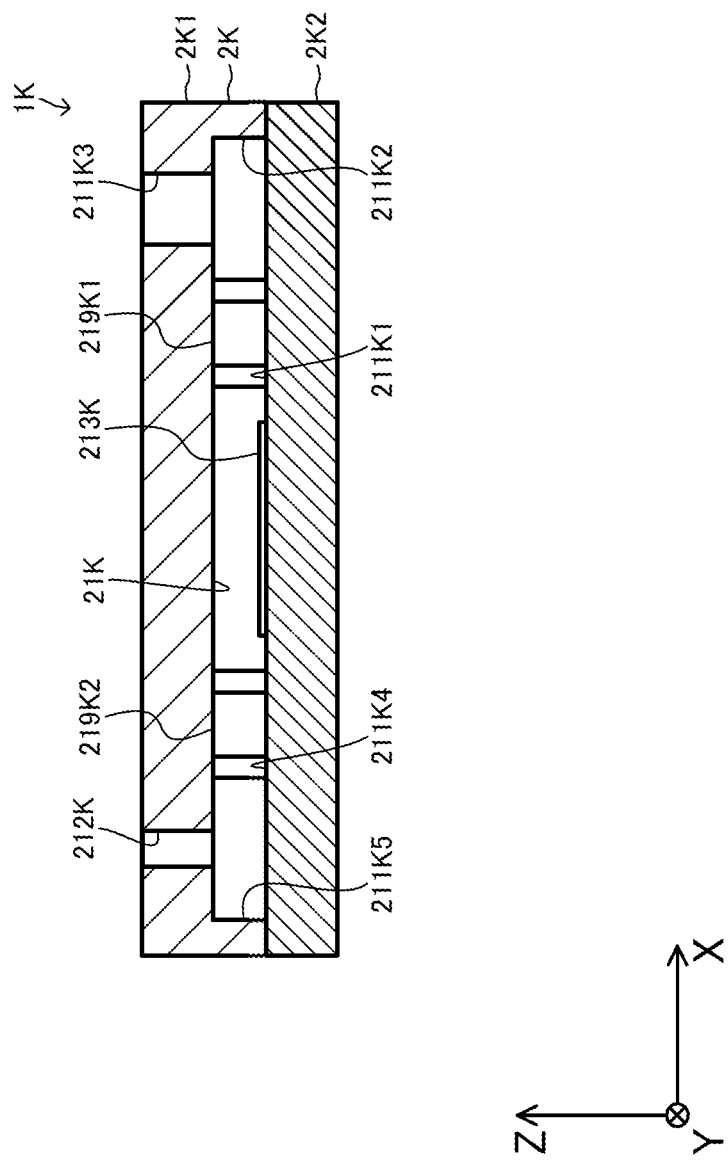
FIG. 35 is a cross-sectional view of an electronic device of the first modification to the ninth embodiment.
Figure 36:
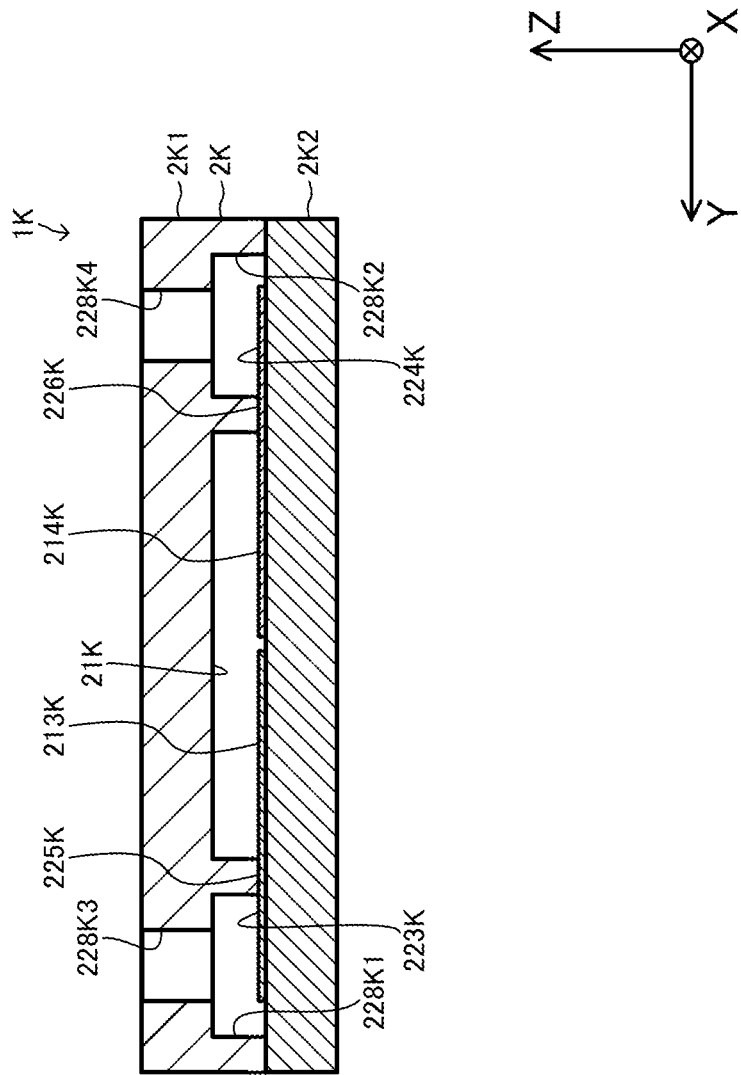
FIG. 36 is a cross-sectional view of the electronic device of the first modification to the ninth embodiment.

Referring to FIGS. 34-36, an electronic device 1K of the first modification to the ninth embodiment includes a main body 2K, in place of the main body 2J of the ninth embodiment. In FIGS. 34-36, illustration of the film 3 is omitted.

FIG. 35 is a cross-sectional view of the electronic device 1K on the plane passing Line XXXV-XXXV in FIG. 34. FIG. 36 is a partial cross-sectional view of the electronic device 1K on the plane passing Line XXXVI-XXXVI in FIG. 34.

In this example, the main body 2K is made from silicon (Si). At least a part of the main body 2K may be made from glass. In this example, as illustrated in FIGS. 35 and 36, the main body 2K includes a first structure 2K1 and a second structure 2K2.

Each structure 2K1-2K2 is in a pillar shape extending along the Z axis. In this example, the bottom of each structure 2K1-2K2 is in a square shape. The bottom of each structure 2K1-2K2 may be in any shape other than the square shape (e.g., circular, oval, rectangular, polygonal, or any other shape).

The bottoms of the first structure 2K1 and the second structure 2K2 are in the same shape. The central axes of the two structures 2K1-2K2 coincide with each other.

The first structure 2K1 and the second structure 2K2 are stacked. The end face of the first structure 2K1 on the negative direction side of the Z axis contacts the end face of the second structure 2K2 on the positive direction side of the Z axis.

The first structure 2K1 includes a first recess 21K, a second recess 211K1, a third recess 211K2, a first through-hole part 211K3, a fourth recess 211K4, a fifth recess 211K5, a sixth recess 228K1, a seventh recess 228K2, a second through-hole part 228K3, and a third through-hole part 228K4.

The recesses 21K, 211K1, 211K2, 211K4, 211K5, 228K1, 228K2 define a space adjoining the second structure 2K2 on the end face of the first structure 2K1 on the negative direction side of the Z axis. In other words, the recesses 21K, 211K1, 211K2, 211K4, 211K5, 228K1, 228K2 open at end face of the first structure 2K1 on the negative direction side of the Z axis.

The space defined by the recesses 21K, 211K1, 211K2, 211K4, 211K5, 228K1, 228K2 contacts the end face of the second structure 2K2 on the positive direction side of the Z axis.

The space defined by the first recess 21K is in a pillar shape extending along the Z axis. In this example, the bottom of the space defined by the first recess 21K is in a rectangular shape of which the long sides and the short sides extend along the Y axis and the X axis, respectively. The bottom of the space defined by the first recess 21K may be in any shape other than the rectangular shape (e.g., circular, oval, square, polygonal, or other shape).

In this example, the position of the space defined by the first recess 21K on the XY plane is the center part of the first structure 2K1 on the XY plane.

Each of the spaces defined by the second recess 211K1 and the fourth recess 211K4 is in a pillar shape extending along the Z axis. In this example, the bottom of each of the spaces respectively defined by the second recess 211K1 and the fourth recess 211K4 is in a rectangular shape of which the long sides and the short sides extend along the X axis and the Y axis, respectively. The bottom of each of the spaces respectively defined by the second recess 211K1 and the fourth recess 211K4 may be in any shape other than the rectangular shape (e.g., circular, oval, square, polygonal, or other shape).

The short sides of the bottom of each of the spaces respectively defined by the second recess 211K1 and the fourth recess 211K4 is shorter than the long sides of the bottom of the space defined by the first recess 21K. In this example, the second recess 211K1 and the fourth recess 211K4 are each located at the center part of the first structure 2K1 in the Y-axis direction.

The end of the second recess 211K1 on the negative direction side of the X axis is connected to the end face of the first recess 21K on the positive direction side of the X axis. In other words, the space defined by the second recess 211K1 continuously communicates with the space defined by the first recess 21K.

The end of the fourth recess 211K4 on the positive direction side of the X axis is connected to the end face of the first recess 21K on the negative direction side of the X axis. In other words, the space defined by the fourth recess 211K4 continuously communicates with the space defined by the first recess 21K.

Each of the spaces respectively defined by the third recess 211K2 and the fifth recess 211K5 is in a pillar shape extending along the Z axis. In this example, the bottom of each of the spaces respectively defined by the third recess 211K2 and the fifth recess 211K5 is in a rectangular shape of which the long sides and the short sides extend along the Y axis and the X axis, respectively. The bottom of each of the spaces respectively defined by the third recess 211K2 and the fifth recess 211K5 may be in any shape other than the rectangular shape (e.g., circular, oval, square, polygonal, or other shape).

The long sides of the bottom of each of the spaces respectively defined by the third recess 211K2 and the fifth recess 211K5 is longer than the short sides of the bottom of the space defined by the second recess 211K1 or the fourth recess 211K4. In this example, the long sides of the bottom of each of the spaces respectively defined by the third recess 211K2 and the fifth recess 211K5 is shorter than the long sides of the bottom of the space defined by the first recess 21K. In this example, the third recess 211K2 and the fifth recess 211K5 are each located at a region which is the center part of the first structure 2K1 in the Y-axis direction, and is the end part of the first structure 2K1 in the X-axis direction.

The end of the second recess 211K1 on the positive direction side of the X axis is connected to the end face of the third recess 211K2 on the negative direction side of the X axis. In other words, the space defined by the second recess 211K1 continuously communicates with the space defined by the third recess 211K2.

The end of the fourth recess 211K4 on the negative direction side of the X axis is connected to the end face of the fifth recess 211K5 on the positive direction side of the X axis. In other words, the space defined by the fourth recess 211K4 continuously communicates with the space defined by the fifth recess 211K5.

Each of the spaces respectively defined by the sixth recess 228K1 and the seventh recess 228K2 is in a pillar shape extending along the Z axis. In this example, the bottom of the spaces respectively defined by the sixth recess 228K1 and the seventh recess 228K2 is in a rectangular shape of which the long sides and the short sides extend along the X axis and the Y axis, respectively. The bottom of each of the spaces respectively defined by the sixth recess 228K1 and the seventh recess 228K2 may be in any shape other than the rectangular shape (e.g., circular, oval, square, polygonal, or other shape).

The long sides of the bottom of each of the spaces respectively defined by the sixth recess 228K1 and the seventh recess 228K2 is slightly shorter than the short sides of the bottom of the space defined by the first recess 21K. In this example, the sixth recess 228K1 and the seventh recess 228K2 are each located at a region which is the center part of the first structure 2K1 in the X-axis direction, and is the end part of the first structure 2K1 in the Y-axis direction.

As illustrated in FIGS. 34 and 35, the first through-hole part 211K3 defines a hole that passes through the wall of the first structure 2K1 defining the end face of the third recess 211K2 on the positive direction side of the Z axis in the Z-axis direction, and is in a pillar shape extending along the Z axis.

In this example, the bottom of the hole defined by the first through-hole part 211K3 is in a rectangular shape. The bottom of the hole defined by the first through-hole part 211K3 may be in any shape other than the rectangular shape (e.g., circular, oval, square, polygonal, or other shape). The hole defined by the first through-hole part 211K3 may be shaped to be a part of a cone.

In this example, the outer edge of the hole defined by the first through-hole part 211K3 on the XY plane is located inside the outer edge of the space defined by the third recess 211K2 on the XY plane.

As illustrated in FIGS. 34 and 36, the second through-hole part 228K3 defines a hole that passes through the wall of the first structure 2K1 defining the end face of the sixth recess 228K1 on the positive direction side of the Z axis in the Z-axis direction, and is in a pillar shape extending along the Z axis. The third through-hole part 228K4 defines a hole that passes through the wall of the first structure 2K1 defining the end face of the seventh recess 228K2 on the positive direction side of the Z axis in the Z-axis direction, and is in a pillar shape extending along the Z axis.

In this example, the bottom of each of the holes respectively defined by the second through-hole part 228K3 and the third through-hole part 228K4 is in a rectangular shape. The bottom of each of the holes respectively defined by the second through-hole part 228K3 and the third through-hole part 228K4 may be in any shape other than the rectangular shape (e.g., circular, oval, square, polygonal, or other shape). The respective holes defined by the second through-hole part 228K3 and the third through-hole part 228K4 may be shaped to be a part of a cone.

In this example, the outer edge of the hole defined by the second through-hole part 228K3 on the XY plane is located inside the outer edge of the space defined by the sixth recess 228K1 on the XY plane.

Further, in this example, the outer edge of the hole defined by the third through-hole part 228K4 on the XY plane is located inside the outer edge of the space defined by the seventh recess 228K2 on the XY plane.

In this example, the space defined by the end face of the second structure 2K2 on the positive direction side of the Z axis and the first recess 21K constitutes the first space SP1 defined inside the main body 2K.

In this example, the spaces and the holes defined by the end face of the second structure 2K2 on the positive direction side of the Z axis, the second recess 211K1, the third recess 211K2, and the first through-hole part 211K3 constitute the channel communicating between the first space SP1 and the outside of the main body 2K.

The electronic device 1K may include a retaining member made from porous material in the first space SP1. In this case, the porous material is preferably hydrophilic.

In this example, the first recess 21K, the second recess 211K1, the third recess 211K2, and the first through-hole part 211K3 are coated with hydrophilic films. The hydrophilic films are made from silicon dioxide, for example.

As illustrated in FIGS. 34 and 35, the first structure 2K1 includes multiple (three in this example) through-hole parts 212K.

Each through-hole part 212K defines a hole that passes through the wall of the first structure 2K1 defining the end face of the fifth recess 211K5 on the positive direction side of the Z axis in the Z-axis direction, and is in a pillar shape extending along the Z axis.

In this example, the bottom of the hole defined by each through-hole part 212K is in a circular shape. The bottom of the hole defined by each through-hole part 212K may be in any shape other than the circular shape (e.g., oval, square, rectangular, polygonal, or other shape). The hole defined by each through-hole part 212K may be shaped to be a part of a cone.

In this example, the area of the bottom of the hole defined by each through-hole part 212K is smaller than the area of the bottom of the hole defined by the first through-hole part 211K3. The bottom of the hole defined by each through-hole part 212K has a diameter between 2 μm and 200 μm, for example.

As illustrated in FIG. 34, the multiple through-hole parts 212K are spaced apart at regular intervals along the Y axis.

In the manner as described above, the hole defined by each through-hole part 212K communicates between the first space SP1 and the outside of the main body 2K. The number of the through-hole parts 212K may be any number other than three.

In this example, each through-hole part 212K is covered with a water-repellent film. The water-repellent film is made from fluorocarbon resin (e.g., resin containing polytetrafluoroethylene as the main component), for example.

Further, the electronic device 1K includes a first electrode 213K, a second electrode 214K, and multiple (four in this example) volume changing bodies 219K1, 219K2, in place of the first electrode 213J, the second electrode 214J, and the multiple volume changing bodies 219J of the ninth embodiment.

The first electrode 213K, and the second electrode 214K are configured similarly to the first electrode 213J and the second electrode 214J.

The volume changing bodies 219K1, 219K2 are configured similarly to the volume changing bodies 219J except for the fact that the volume changing bodies 219K1, 219K2 are also provided at the fourth recess 211K4.

The two volume changing bodies 219K1 are provided at the second recess 211K1, similarly to the volume changing bodies 219J. The two volume changing bodies 219K2 are further provided at the fourth recess 211K4.

As a result, in this example, in addition to the channel communicating between the first space SP1 and the outside of the main body 2K through the hole defined by the first through-hole part 211K3, the channel communicating between the first space SP1 and the outside of the main body 2K through the hole defined by the through-hole parts 212K, is also closed responsive to pH. This can increase the possibility of preventing any matter other than the gastric fluid (e.g., fluid with pH different from that of gastric fluid, solid matter, or the like) from entering the first space SP1.

In this example, the volume changing bodies 219K1, 219K2 correspond to a valve that closes the channel communicating between the first space SP1 and the outside of the main body 2K, responsive to pH.

Further, the electronic device 1K includes a first terminal 223K, a second terminal 224K, a first conductor 225K, and a second conductor 226K, in place of the first through-hole part 221J, the second through-hole part 222J, the first terminal 223J, the second terminal 224J, the first conductor 225J, the second conductor 226J, and the circuit 227J of the ninth embodiment.

As illustrated in FIGS. 34 and 36, the first terminal 223K contacts the end face of the second structure 2K2 on the positive direction side of the Z axis in the space defined by the sixth recess 228K1. The outer edge of the first terminal 223K on the XY plane coincides with the outer edge of the second through-hole part 228K3 on the XY plane. The first conductor 225K connects the first electrode 213K and the first terminal 223K.

The second terminal 224K contacts the end face of the second structure 2K2 on the positive direction side of the Z axis in the space defined by the seventh recess 228K2. The outer edge of second terminal 224K on the XY plane coincides with the outer edge of the third through-hole part 228K4 on the XY plane. The second conductor 226K connects the second electrode 214K and the second terminal 224K.

The electronic device 1K further includes a circuit that is not illustrated, which is connected to the first terminal 223K through the second through-hole part 228K3, and is also connected to the second terminal 224K through the third through-hole part 228K4.

As set forth above, the electronic device 1K of the first modification to the ninth embodiment operates similarly to the electronic device 1J of the ninth embodiment. Accordingly, effects and advantages similar to those of the electronic device 1J of the ninth embodiment are also achieved by the electronic device 1K of the first modification to the ninth embodiment.

Further, in accordance with the electronic device 1K of the first modification to the ninth embodiment, in addition to the channel communicating between the first space SP1 and the outside of the main body 2K through the hole defined by the first through-hole part 211K3, the channel communicating between the first space SP1 and the outside of the main body 2K through the hole defined by the through-hole parts 212K, is also closed responsive to pH. This can increase the possibility of preventing any matter other than the gastric fluid (e.g., fluid with pH different from that of gastric fluid, solid matter, or the like) from entering the first space SP1.

According to the above-described technologies, it is possible to prevent a reduction in the power output.

The present invention is not limited to the embodiments described above. Various changes that can be conceived by those skilled in the art may be made to the above-described embodiments, in without departing from the spirit of the present invention, for example. Any combinations of the above-described embodiments and modifications may be adopted as another modification to the above-described embodiments, in without departing from the spirit of the present invention, for example.

All examples and conditional language provided herein are intended for pedagogical purposes to aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiment(s) of the present invention have been described in detail, it should be understood that the various changes, substitutions, and alterations could be made hereto without departing from the spirit and scope of the invention.)

What is claimed is:

1. A battery comprising:
   a main body having a space therein, and having a channel communicating between an outside of the main body and the space;
   a pair of electrodes adjoining the space; and
   a valve that closes the channel in response to a predetermined range of the pH external to the space.

2. The battery according to claim 1, wherein the valve comprises:
   a valve seat;
   a support that is dissolved in response to the predetermined range of the pH external to the space; and
   a valve member that is biased toward the valve seat and supported by the support at a location distant from the valve seat, and closes the channel by contacting the valve seat upon the dissolution of the support.

3. The battery according to claim 1, wherein the valve comprises:
   a valve seat;
   a volume changing body that undergoes a volume change in response to the predetermined range of the pH external to the space; and
   a valve member that is supported by the main body with contacting the volume changing body, and closes the channel by contacting the valve seat upon the volume change of the volume changing body.

4. The battery according to claim 1, wherein the valve is disposed at the channel, and comprises a volume changing body that closes the channel by undergoing a volume increase in response to the predetermined range of the pH external to the space.

5. The battery according to claim 4, wherein at least a part of the main body is made from optically transmissive material such that the volume changing body is irradiated with light through at least the part of the main body.

6. The battery according to claim 1, wherein the valve closes the channel when the pH external to the space is higher than a predetermined threshold.

7. The battery according to claim 1, wherein the valve closes the channel once a fluid has been introduced to the space through the channel, when the pH external to the space is lower than a predetermined threshold.

8. The battery according to claim 1, further comprising a film that coats at least a part of the main body, and is dissolved in response to the predetermined range of the pH external to the space.

9. An electronic device comprising:
   a battery that generates electric power; and
   a circuit that is energized by the generated electric power,
   the battery comprising:
      a main body having a space therein, and having a channel communicating between an outside of the main body and the space;
      a pair of electrodes adjoining the space; and
      a valve that closes the channel in response to a predetermined range of the pH external to the space.

10. The electronic device according to claim 9, wherein the battery is disposed at a first layer, and
    the circuit is disposed at a second layer adjacent to the first layer.

11. The electronic device according to claim 10, further comprising a second battery different from the battery as a first battery,
    the second battery being disposed at a third layer that is disposed opposite to the first layer relative to the second layer, the second layer being disposed between the first layer and the third layer.

* * * * *